(12) United States Patent
Hacohen et al.

(10) Patent No.: US 10,531,872 B2
(45) Date of Patent: Jan. 14, 2020

(54) VALVE PROSTHESIS CONFIGURED FOR DEPLOYMENT IN ANNULAR SPACER

(71) Applicant: CARDIOVALVE LTD., Or Yehuda (IL)

(72) Inventors: Gil Hacohen, Ramat Gan (IL); Yossi Gross, Moshav Mazor (IL); Tal Reich, Moshav Moledet (IL)

(73) Assignee: CARDIOVALVE LTD., Or Yehuda (IL)

( * ) Notice: Subject to any disclaimer, the term of this patent is extended or adjusted under 35 U.S.C. 154(b) by 0 days.

(21) Appl. No.: 16/040,831

(22) Filed: Jul. 20, 2018

(65) Prior Publication Data

US 2019/0015093 A1 Jan. 17, 2019

Related U.S. Application Data

(63) Continuation of application No. 15/691,032, filed on Aug. 30, 2017, which is a continuation of application
(Continued)

(51) Int. Cl.
*A61F 2/24* (2006.01)
*A61B 17/04* (2006.01)
*A61B 17/00* (2006.01)

(52) U.S. Cl.
CPC ........ *A61B 17/0401* (2013.01); *A61F 2/2409* (2013.01); *A61F 2/2418* (2013.01);
(Continued)

(58) Field of Classification Search
CPC .... A61F 2/2409; A61F 2/2418; A61F 2/2427; A61F 2/2436
See application file for complete search history.

(56) References Cited

U.S. PATENT DOCUMENTS

| 4,261,342 A | 4/1981 | Aranguren Guo |
| 4,423,525 A | 1/1984 | Vallana et al. |

(Continued)

FOREIGN PATENT DOCUMENTS

| EP | 1264582 A2 | 11/2002 |
| EP | 1768630 B1 | 1/2015 |

(Continued)

OTHER PUBLICATIONS

An Office Action dated Jun. 6, 2018, which issued during the prosecution of UK Patent Application No. 1720803.4.
(Continued)

*Primary Examiner* — Robert A Lynch
(74) *Attorney, Agent, or Firm* — Finnegan, Henderson, Farabow, Garrett & Dunner, L.L.P.

(57) ABSTRACT

Embodiments of the present disclosure are directed to prosthetic heart valves and methods of use thereof. In one implementation, a prosthetic heart valve may include an annular spacer having a spacer opening therein and a disc-shaped wall configured to obstruct blood flow. The annular spacer may be configured for engaging with a native heart valve opening, such as the orifice of a mitral valve. The spacer opening may be sized to be smaller than the native heart valve opening. The prosthetic heart valve may also include a central valve section configured for disposal within the spacer opening. The central valve section may be separate from the annular spacer and may include one or more prosthetic valve leaflets.

19 Claims, 43 Drawing Sheets

Related U.S. Application Data

No. 14/689,608, filed on Apr. 17, 2015, now Pat. No. 9,763,657, which is a continuation of application No. 13/811,308, filed as application No. PCT/IL2011/000582 on Jul. 21, 2011, now Pat. No. 9,017,399, which is a continuation-in-part of application No. 12/840,463, filed on Jul. 21, 2010, now Pat. No. 9,132,009, and a continuation-in-part of application No. 13/033,852, filed on Feb. 24, 2011, now Pat. No. 8,992,604, which is a continuation-in-part of application No. 12/840,463, filed on Jul. 21, 2010, now Pat. No. 9,132,009.

(60) Provisional application No. 61/492,449, filed on Jun. 2, 2011.

(52) U.S. Cl.
CPC .......... *A61F 2/2436* (2013.01); *A61F 2/2457* (2013.01); *A61B 2017/00243* (2013.01); *A61B 2017/0441* (2013.01); *A61B 2017/0464* (2013.01); *A61F 2/243* (2013.01); *A61F 2/2412* (2013.01); *A61F 2/2427* (2013.01); *A61F 2/2466* (2013.01); *A61F 2220/0016* (2013.01); *A61F 2230/005* (2013.01); *A61F 2230/0041* (2013.01)

(56) References Cited

U.S. PATENT DOCUMENTS

| | | |
|---|---|---|
| 4,853,986 A | 8/1989 | Allen |
| 4,892,541 A | 1/1990 | Alonso |
| 5,103,420 A | 4/1992 | Marks |
| 5,314,473 A | 5/1994 | Godin |
| 5,405,378 A | 4/1995 | Strecker |
| 5,443,500 A | 8/1995 | Sigwari |
| 5,607,444 A | 3/1997 | Lam |
| 5,607,470 A | 3/1997 | Milo |
| 5,647,857 A | 7/1997 | Anderson et al. |
| 5,765,682 A | 6/1998 | Bley et al. |
| 5,868,777 A | 2/1999 | Lam |
| 5,873,906 A | 2/1999 | Lau et al. |
| 5,954,766 A | 9/1999 | Zadno-Azizi et al. |
| 5,980,565 A | 11/1999 | Jayaraman |
| 6,019,787 A | 2/2000 | Richard et al. |
| 6,042,607 A | 3/2000 | Williamson, IV et al. |
| 6,074,417 A | 6/2000 | Peredo |
| 6,113,612 A | 9/2000 | Swanson et al. |
| 6,120,534 A | 9/2000 | Ruiz |
| 6,152,937 A | 11/2000 | Peterson et al. |
| 6,165,210 A | 12/2000 | Lau et al. |
| 6,187,020 B1 | 2/2001 | Zegdi et al. |
| 6,193,745 B1 | 2/2001 | Fogarty et al. |
| 6,264,700 B1 | 7/2001 | Kilcoyne et al. |
| 6,287,339 B1 | 9/2001 | Vazquez et al. |
| 6,332,893 B1 | 12/2001 | Mortier et al. |
| 6,334,873 B1 | 1/2002 | Lane et al. |
| 6,350,278 B1 | 2/2002 | Lenker et al. |
| 6,352,561 B1 | 3/2002 | Leopold et al. |
| 6,391,036 B1 | 5/2002 | Berg et al. |
| 6,402,780 B2 | 6/2002 | Williamson, IV et al. |
| 6,409,755 B1 | 6/2002 | Vrba |
| 6,419,696 B1 | 7/2002 | Ortiz et al. |
| 6,428,550 B1 | 8/2002 | Vargas et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,511,491 B2 | 1/2003 | Grudem et al. |
| 6,530,952 B2 | 3/2003 | Vesely |
| 6,540,782 B1 | 4/2003 | Snyders |
| 6,551,350 B1 | 4/2003 | Thornton et al. |
| 6,558,396 B1 | 5/2003 | Inoue |
| 6,558,418 B2 | 5/2003 | Carpentier et al. |
| 6,569,196 B1 | 5/2003 | Vesely |
| 6,602,263 B1 | 8/2003 | Swanson et al. |
| 6,616,675 B1 | 9/2003 | Evard et al. |
| 6,652,556 B1 | 11/2003 | VanTassel et al. |
| 6,669,724 B2 | 12/2003 | Park et al. |
| 6,682,558 B2 | 1/2004 | Tu et al. |
| 6,699,256 B1 | 3/2004 | Logan et al. |
| 6,716,244 B2 | 4/2004 | Klaco |
| 6,719,781 B1 | 4/2004 | Kim |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,764,518 B2 | 7/2004 | Godin |
| 6,767,362 B2 | 7/2004 | Schreck |
| 6,797,002 B2 | 9/2004 | Spence et al. |
| 6,821,297 B2 | 11/2004 | Snyders |
| 6,830,585 B1 | 12/2004 | Arlof et al. |
| 6,830,638 B2 | 12/2004 | Boylan et al. |
| 6,893,460 B2 | 5/2005 | Spenser et al. |
| 6,960,217 B2 | 11/2005 | Bolduc |
| 6,964,684 B2 | 11/2005 | Ortiz et al. |
| 6,974,476 B2 | 12/2005 | McGuckin, Jr. et al. |
| 7,011,681 B2 | 3/2006 | Vesely |
| 7,018,406 B2 | 3/2006 | Seguin et al. |
| 7,041,132 B2 | 5/2006 | Quijano et al. |
| 7,077,861 B2 | 7/2006 | Spence |
| 7,101,395 B2 | 9/2006 | Tremulis et al. |
| 7,101,396 B2 | 9/2006 | Artof et al. |
| 7,137,184 B2 | 11/2006 | Schreck |
| 7,172,625 B2 | 2/2007 | Shu et al. |
| 7,198,646 B2 | 4/2007 | Figulla |
| 7,201,772 B2 | 4/2007 | Schwammenthal et al. |
| 7,226,477 B2 | 6/2007 | Cox |
| 7,288,111 B1 | 10/2007 | Holloway et al. |
| 7,316,716 B2 | 1/2008 | Egan |
| 7,329,279 B2 | 2/2008 | Haug et al. |
| 7,335,213 B1 | 2/2008 | Hyde et al. |
| 7,351,256 B2 | 4/2008 | Hojeibane et al. |
| 7,374,573 B2 | 5/2008 | Gabbay |
| 7,377,938 B2 | 5/2008 | Sarac et al. |
| 7,381,218 B2 | 6/2008 | Schreck |
| 7,381,219 B2 | 6/2008 | Salahieh et al. |
| 7,404,824 B1 | 7/2008 | Webler et al. |
| 7,422,603 B2 | 9/2008 | Lane |
| 7,429,269 B2 | 9/2008 | Schwammenthal et al. |
| 7,442,204 B2 | 10/2008 | Schwammenthal et al. |
| 7,445,530 B2 | 11/2008 | Lashinski et al. |
| 7,455,677 B2 | 11/2008 | Vargas et al. |
| 7,455,688 B2 | 11/2008 | Furst et al. |
| 7,462,162 B2 | 12/2008 | Phan et al. |
| 7,481,838 B2 | 1/2009 | Carpentier et al. |
| 7,510,575 B2 | 3/2009 | Spenser et al. |
| 7,513,909 B2 | 4/2009 | Lane et al. |
| 7,524,331 B2 | 4/2009 | Birdsall |
| 7,527,646 B2 | 5/2009 | Rahdert et al. |
| 7,556,646 B2 | 7/2009 | Yang et al. |
| 7,582,111 B2 | 9/2009 | Krolik et al. |
| 7,585,321 B2 | 9/2009 | Cribier et al. |
| 7,597,711 B2 | 10/2009 | Drews et al. |
| 7,611,534 B2 | 11/2009 | Kapadia et al. |
| 7,621,948 B2 | 11/2009 | Herrmann et al. |
| 7,625,403 B2 | 12/2009 | Krivoruchko et al. |
| 7,632,302 B2 | 12/2009 | Vreeman et al. |
| 7,648,528 B2 | 1/2010 | Styrc |
| 7,682,380 B2 | 3/2010 | Thornton et al. |
| 7,708,775 B2 | 5/2010 | Rowe et al. |
| 7,717,952 B2 | 5/2010 | Case et al. |
| 7,717,955 B2 | 5/2010 | Lane et al. |
| 7,731,741 B2 | 6/2010 | Eidenschink |
| 7,748,389 B2 | 7/2010 | Salahieh et al. |
| 7,753,922 B2 | 7/2010 | Starksen |
| 7,758,595 B2 | 7/2010 | Allen et al. |
| 7,758,632 B2 | 7/2010 | Hojeibane et al. |
| 7,758,640 B2 | 7/2010 | Vesely |
| 7,771,467 B2 | 8/2010 | Svensson |
| 7,771,469 B2 | 8/2010 | Liddicoat |
| 7,776,083 B2 | 8/2010 | Vesely |
| 7,780,726 B2 | 8/2010 | Seguin |
| 7,799,069 B2 | 9/2010 | Bailey et al. |

(56) References Cited

U.S. PATENT DOCUMENTS

| | | |
|---|---|---|
| 7,803,181 B2 | 9/2010 | Furst et al. |
| 7,811,316 B2 | 10/2010 | Kalmann et al. |
| 7,824,442 B2 | 11/2010 | Salahieh et al. |
| 7,837,645 B2 | 11/2010 | Bessler et al. |
| 7,837,727 B2 | 11/2010 | Goetz et al. |
| 7,842,081 B2 | 11/2010 | Yadin |
| 7,850,725 B2 | 12/2010 | Vardi et al. |
| 7,871,432 B2 | 1/2011 | Bergin |
| 7,871,436 B2 | 1/2011 | Ryan et al. |
| 7,887,583 B2 | 2/2011 | Macoviak |
| 7,892,281 B2 | 2/2011 | Seguin et al. |
| 7,896,915 B2 | 3/2011 | Guyenot et al. |
| 7,914,544 B2 | 3/2011 | Nguyen et al. |
| 7,914,569 B2 | 3/2011 | Nguyen et al. |
| 7,927,370 B2 | 4/2011 | Webler et al. |
| 7,942,927 B2 | 5/2011 | Kaye et al. |
| 7,947,072 B2 | 5/2011 | Yang et al. |
| 7,947,075 B2 | 5/2011 | Goetz et al. |
| 7,951,195 B2 | 5/2011 | Antonssen et al. |
| 7,955,375 B2 | 6/2011 | Agnew |
| 7,955,377 B2 | 6/2011 | Melsheimer |
| 7,955,384 B2 | 6/2011 | Rafiee et al. |
| 7,959,666 B2 | 6/2011 | Salahieh et al. |
| 7,959,672 B2 | 6/2011 | Salahieh et al. |
| 7,967,833 B2 | 6/2011 | Sterman et al. |
| 7,967,857 B2 | 6/2011 | Lane |
| 7,981,151 B2 | 7/2011 | Rowe |
| 7,981,153 B2 | 7/2011 | Fogarty et al. |
| 7,992,567 B2 | 8/2011 | Hirotsuka et al. |
| 7,993,393 B2 | 8/2011 | Carpentier et al. |
| 8,002,820 B2 | 8/2011 | Seguin |
| 8,002,825 B2 | 8/2011 | Letac et al. |
| 8,016,877 B2 | 9/2011 | Seguin et al. |
| 8,016,882 B2 | 9/2011 | Macoviak et al. |
| 8,021,420 B2 | 9/2011 | Dolan |
| 8,021,421 B2 | 9/2011 | Fogarty et al. |
| 8,025,695 B2 | 9/2011 | Fogarty et al. |
| 8,029,518 B2 | 10/2011 | Goldfarb et al. |
| 8,029,557 B2 | 10/2011 | Sobrino-Serrano et al. |
| 8,029,564 B2 | 10/2011 | Johnson et al. |
| 8,034,104 B2 | 10/2011 | Carpentier et al. |
| 8,038,720 B2 | 10/2011 | Wallace et al. |
| 8,043,360 B2 | 10/2011 | McNamara et al. |
| 8,048,138 B2 | 11/2011 | Sullivan et al. |
| 8,048,140 B2 | 11/2011 | Purdy |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,057,493 B2 | 11/2011 | Goldfarb et al. |
| 8,057,532 B2 | 11/2011 | Hoffman |
| 8,057,540 B2 | 11/2011 | Letec et al. |
| 8,062,355 B2 | 11/2011 | Figulla et al. |
| 8,062,359 B2 | 11/2011 | Marquez et al. |
| 8,070,708 B2 | 12/2011 | Rottenberg et al. |
| 8,070,800 B2 | 12/2011 | Lock et al. |
| 8,070,802 B2 | 12/2011 | Lamphere et al. |
| 8,070,804 B2 | 12/2011 | Hyde et al. |
| 8,075,611 B2 | 12/2011 | Millwee et al. |
| 8,080,054 B2 | 12/2011 | Rowe |
| 8,083,793 B2 | 12/2011 | Lane et al. |
| D652,927 S | 1/2012 | Braido et al. |
| D653,341 S | 1/2012 | Braido et al. |
| 8,092,518 B2 | 1/2012 | Schreck |
| 8,092,520 B2 | 1/2012 | Quadri |
| 8,092,521 B2 | 1/2012 | Figulla et al. |
| 8,105,377 B2 | 1/2012 | Liddicoat |
| 8,109,996 B2 | 2/2012 | Stacchino et al. |
| 8,118,866 B2 | 2/2012 | Herrmann et al. |
| 8,133,270 B2 | 3/2012 | Kheradvar et al. |
| 8,136,218 B2 | 3/2012 | Millwee et al. |
| 8,137,398 B2 | 3/2012 | Tuval et al. |
| 8,142,492 B2 | 3/2012 | Forster et al. |
| 8,142,494 B2 | 3/2012 | Rahdert et al. |
| 8,142,496 B2 | 3/2012 | Berreklouw |
| 8,142,497 B2 | 3/2012 | Friedman |
| 8,147,504 B2 | 4/2012 | Ino et al. |
| 8,157,852 B2 | 4/2012 | Bloom et al. |
| 8,157,860 B2 | 4/2012 | McNamara et al. |
| 8,163,008 B2 | 4/2012 | Wilson et al. |
| 8,163,014 B2 | 4/2012 | Lane et al. |
| D660,433 S | 5/2012 | Braido et al. |
| D660,967 S | 5/2012 | Braido et al. |
| 8,167,894 B2 | 5/2012 | Miles et al. |
| 8,167,932 B2 | 5/2012 | Bourang et al. |
| 8,167,935 B2 | 5/2012 | McGuckin, Jr. et al. |
| 8,172,896 B2 | 5/2012 | McNamara et al. |
| 8,172,898 B2 | 5/2012 | Alferness et al. |
| 8,177,836 B2 | 5/2012 | Lee et al. |
| 8,182,528 B2 | 5/2012 | Salahieh et al. |
| 8,211,169 B2 | 7/2012 | Lane et al. |
| 8,216,301 B2 | 7/2012 | Bonhoeffer et al. |
| 8,221,492 B2 | 7/2012 | Case et al. |
| 8,221,493 B2 | 7/2012 | Boyle et al. |
| 8,226,710 B2 | 7/2012 | Nguyen et al. |
| 8,231,670 B2 | 7/2012 | Salahieh et al. |
| 8,236,045 B2 | 8/2012 | Benichou et al. |
| 8,236,049 B2 | 8/2012 | Rowe et al. |
| 8,252,042 B2 | 8/2012 | McNamara et al. |
| 8,252,051 B2 | 8/2012 | Chau et al. |
| 8,252,052 B2 | 8/2012 | Salahieh et al. |
| 8,257,390 B2 | 9/2012 | Carley et al. |
| 8,267,988 B2 | 9/2012 | Hamer et al. |
| 8,277,501 B2 | 10/2012 | Chalekian et al. |
| 8,287,591 B2 | 10/2012 | Keidar et al. |
| 8,298,280 B2 | 10/2012 | Yadin et al. |
| 8,303,653 B2 | 11/2012 | Bonhoeffer et al. |
| 8,308,798 B2 | 11/2012 | Pintor et al. |
| 8,313,525 B2 | 11/2012 | Tuval et al. |
| 8,317,853 B2 | 11/2012 | Agnew |
| 8,317,855 B2 | 11/2012 | Gregorich et al. |
| 8,323,335 B2 | 12/2012 | Rowe et al. |
| 8,328,868 B2 | 12/2012 | Paul et al. |
| 8,337,541 B2 | 12/2012 | Quadri et al. |
| 8,343,174 B2 | 1/2013 | Goldfarb et al. |
| 8,343,213 B2 | 1/2013 | Salahieh et al. |
| 8,348,999 B2 | 1/2013 | Kheradvar et al. |
| 8,366,767 B2 | 2/2013 | Zhang |
| 8,372,140 B2 | 2/2013 | Hoffman |
| 8,377,119 B2 | 2/2013 | Drews et al. |
| 8,398,708 B2 | 3/2013 | Meiri et al. |
| 8,403,981 B2 | 3/2013 | Forster et al. |
| 8,403,983 B2 | 3/2013 | Quadri et al. |
| 8,408,214 B2 | 4/2013 | Spenser et al. |
| 8,414,644 B2 | 4/2013 | Quadri et al. |
| 8,425,593 B2 | 4/2013 | Braido et al. |
| 8,430,934 B2 | 4/2013 | Das |
| 8,444,689 B2 | 5/2013 | Zhang |
| 8,449,599 B2 | 5/2013 | Chau et al. |
| 8,449,625 B2 | 5/2013 | Campbell et al. |
| 8,454,686 B2 | 6/2013 | Alkhatib |
| 8,460,365 B2 | 6/2013 | Haverkost et al. |
| 8,474,460 B2 | 7/2013 | Barrett et al. |
| 8,500,821 B2 | 8/2013 | Sobrino-Serrano et al. |
| 8,512,400 B2 | 8/2013 | Tran et al. |
| 8,539,662 B2 | 9/2013 | Stacchino et al. |
| 8,545,544 B2 | 10/2013 | Spenser et al. |
| 8,551,160 B2 | 10/2013 | Figulla et al. |
| 8,551,161 B2 | 10/2013 | Dolan |
| 8,562,672 B2 | 10/2013 | Bonhoeffer et al. |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,460 B2 | 11/2013 | Wilson et al. |
| 8,591,570 B2 | 11/2013 | Revuelta et al. |
| 8,623,075 B2 | 1/2014 | Murray, III et al. |
| 8,623,080 B2 | 1/2014 | Fogarty et al. |
| 8,628,569 B2 | 1/2014 | Benichou et al. |
| 8,628,570 B2 | 1/2014 | Seguin |
| 8,628,571 B1 | 1/2014 | Hacohen et al. |
| 8,652,203 B2 | 2/2014 | Quadri et al. |
| 8,652,204 B2 | 2/2014 | Quill et al. |
| 8,657,872 B2 | 2/2014 | Seguin |
| 8,663,322 B2 | 3/2014 | Keranen |

(56) References Cited

U.S. PATENT DOCUMENTS

| | | |
|---|---|---|
| 8,673,020 B2 | 3/2014 | Sobrino-Serrano et al. |
| 8,679,174 B2 | 3/2014 | Ottma et al. |
| 8,685,086 B2 | 4/2014 | Navia et al. |
| 8,696,742 B2 | 4/2014 | Pintor et al. |
| 8,728,155 B2 | 5/2014 | Montorfano et al. |
| 8,734,507 B2 | 5/2014 | Keranen |
| 8,747,460 B2 | 6/2014 | Tuval et al. |
| 8,771,345 B2 | 7/2014 | Tuval et al. |
| 8,784,472 B2 | 7/2014 | Eidenschink |
| 8,784,479 B2 | 7/2014 | Antonsson et al. |
| 8,784,481 B2 | 7/2014 | Alkhatib et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,801,776 B2 | 8/2014 | House et al. |
| 8,808,366 B2 | 8/2014 | Braido et al. |
| 8,840,663 B2 | 9/2014 | Salahieh et al. |
| 8,840,664 B2 | 9/2014 | Karapetian et al. |
| 8,845,722 B2 | 9/2014 | Gabbay |
| 8,852,261 B2 | 10/2014 | White |
| 8,852,272 B2 | 10/2014 | Gross et al. |
| 8,870,948 B1 | 10/2014 | Erzberger et al. |
| 8,870,949 B2 | 10/2014 | Rowe |
| 8,870,950 B2 | 10/2014 | Hacohen |
| 8,876,600 B2 | 11/2014 | Behan |
| 8,894,702 B2 | 11/2014 | Quadri et al. |
| 8,900,294 B2 | 12/2014 | Paniagua et al. |
| 8,900,295 B2 | 12/2014 | Migliazza et al. |
| 8,906,083 B2 | 12/2014 | Obermiller et al. |
| 8,911,455 B2 | 12/2014 | Quadri et al. |
| 8,911,489 B2 | 12/2014 | Ben-Muvhar |
| 8,911,493 B2 | 12/2014 | Rowe et al. |
| 8,932,343 B2 | 1/2015 | Alkhatib et al. |
| 8,961,595 B2 | 2/2015 | Akhatib |
| 8,979,922 B2 | 3/2015 | Jayasinhe et al. |
| 8,986,370 B2 | 3/2015 | Annest |
| 8,986,373 B2 | 3/2015 | Chau et al. |
| 8,986,375 B2 | 3/2015 | Garde et al. |
| 8,992,599 B2 | 3/2015 | Thubrikar et al. |
| 8,992,604 B2 | 3/2015 | Gross et al. |
| 8,998,982 B2 | 4/2015 | Richter et al. |
| 9,005,273 B2 | 4/2015 | Salahieh et al. |
| 9,011,527 B2 | 4/2015 | Li et al. |
| 9,017,399 B2 | 4/2015 | Gross et al. |
| D730,520 S | 5/2015 | Braido et al. |
| D730,521 S | 5/2015 | Braido et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| D732,666 S | 6/2015 | Nguyen et al. |
| 9,050,188 B2 | 6/2015 | Schweich, Jr. et al. |
| 9,072,603 B2 | 7/2015 | Tuval et al. |
| 9,084,676 B2 | 7/2015 | Chau et al. |
| 9,125,738 B2 | 9/2015 | Figulla et al. |
| 9,125,740 B2 | 9/2015 | Morriss et al. |
| 9,132,006 B2 | 9/2015 | Spenser et al. |
| 9,132,009 B2 | 9/2015 | Hacohen et al. |
| 9,138,312 B2 | 9/2015 | Tuval et al. |
| 9,155,619 B2 | 10/2015 | Liu et al. |
| 9,173,738 B2 | 11/2015 | Murray, III et al. |
| 9,220,594 B2 | 12/2015 | Braido et al. |
| 9,226,820 B2 | 1/2016 | Braido et al. |
| 9,226,839 B1 | 1/2016 | Kariniemi et al. |
| 9,232,995 B2 | 1/2016 | Kovalsky et al. |
| 9,241,790 B2 | 1/2016 | Lane et al. |
| 9,241,791 B2 | 1/2016 | Braido et al. |
| 9,241,794 B2 | 1/2016 | Braido et al. |
| 9,248,014 B2 | 2/2016 | Lane et al. |
| 9,289,290 B2 | 3/2016 | Alkhatib et al. |
| 9,289,291 B2 | 3/2016 | Gorman, III et al. |
| 9,295,550 B2 | 3/2016 | Nguyen et al. |
| 9,295,552 B2 | 3/2016 | McLean et al. |
| 9,301,836 B2 | 4/2016 | Buchbinder et al. |
| D755,384 S | 5/2016 | Pesce et al. |
| 9,326,652 B2 | 5/2016 | Spenser |
| 9,326,876 B2 | 5/2016 | Acosta et al. |
| 9,345,573 B2 | 5/2016 | Nyuli et al. |
| 9,387,078 B2 | 7/2016 | Gross et al. |
| 9,421,098 B2 | 8/2016 | Gifford, III et al. |
| 9,427,303 B2 | 8/2016 | Liddy et al. |
| 9,427,316 B2 | 8/2016 | Schweich, Jr. et al. |
| 9,445,893 B2 | 9/2016 | Vaturi |
| 9,474,599 B2 | 10/2016 | Keranen |
| 9,474,638 B2 | 10/2016 | Robinson et al. |
| 9,480,559 B2 | 11/2016 | Vidlund et al. |
| 9,498,314 B2 | 11/2016 | Behan |
| 9,532,870 B2 | 1/2017 | Cooper et al. |
| 9,554,897 B2 | 1/2017 | Lane et al. |
| 9,566,152 B2 | 2/2017 | Schweich, Jr. et al. |
| 9,572,665 B2 | 2/2017 | Lane et al. |
| 9,629,716 B2 | 4/2017 | Seguin |
| 9,662,203 B2 | 5/2017 | Sheahan et al. |
| 9,681,952 B2 | 6/2017 | Hacohen |
| 9,717,591 B2 | 8/2017 | Chau et al. |
| 9,743,932 B2 | 8/2017 | Amplatz et al. |
| 9,763,657 B2 | 9/2017 | Hacohen et al. |
| 9,763,817 B2 | 9/2017 | Roeder |
| 9,974,651 B2 | 5/2018 | Hariton et al. |
| 2001/0021872 A1 | 9/2001 | Bailey et al. |
| 2001/0056295 A1 | 12/2001 | Solem |
| 2002/0032481 A1 | 3/2002 | Gabbay |
| 2002/0099436 A1 | 7/2002 | Thornton et al. |
| 2002/0151970 A1 | 10/2002 | Garrison et al. |
| 2002/0177894 A1 | 11/2002 | Acosta et al. |
| 2003/0036791 A1 | 2/2003 | Philipp et al. |
| 2003/0060875 A1 | 3/2003 | Wittens |
| 2003/0069635 A1 | 4/2003 | Cartledge et al. |
| 2003/0074052 A1 | 4/2003 | Besselink |
| 2003/0083742 A1 | 5/2003 | Spence et al. |
| 2003/0105519 A1 | 6/2003 | Fasol et al. |
| 2003/0158578 A1 | 8/2003 | Pantages et al. |
| 2004/0010272 A1 | 1/2004 | Manetakis et al. |
| 2004/0039414 A1 | 2/2004 | Carley et al. |
| 2004/0093060 A1 | 5/2004 | Seguin et al. |
| 2004/0122503 A1 | 6/2004 | Campbell et al. |
| 2004/0122514 A1 | 6/2004 | Fogarty et al. |
| 2004/0133267 A1 | 7/2004 | Lane |
| 2004/0143315 A1 | 7/2004 | Braun et al. |
| 2004/0176839 A1 | 9/2004 | Huynh et al. |
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0210304 A1 | 10/2004 | Seguin et al. |
| 2004/0220593 A1 | 11/2004 | Greenhalgh |
| 2004/0225354 A1 | 11/2004 | Allen et al. |
| 2004/0245433 A1 | 12/2004 | Freitag |
| 2004/0260389 A1 | 12/2004 | Case et al. |
| 2004/0260394 A1 | 12/2004 | Douk et al. |
| 2005/0004668 A1 | 1/2005 | Aklog et al. |
| 2005/0021056 A1 | 1/2005 | St. Goar et al. |
| 2005/0027305 A1 | 2/2005 | Shiu et al. |
| 2005/0038494 A1 | 2/2005 | Eidenschink |
| 2005/0055086 A1 | 3/2005 | Stobie |
| 2005/0075731 A1 | 4/2005 | Artof et al. |
| 2005/0080430 A1 | 4/2005 | Wright, Jr. et al. |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137695 A1 | 6/2005 | Salahieh et al. |
| 2005/0137697 A1 | 6/2005 | Salahieh et al. |
| 2005/0143809 A1 | 6/2005 | Salahieh et al. |
| 2005/0149160 A1 | 7/2005 | McFerran |
| 2005/0154443 A1 | 7/2005 | Linder et al. |
| 2005/0182486 A1 | 8/2005 | Gabbay |
| 2005/0197695 A1 | 9/2005 | Stacchino et al. |
| 2005/0203549 A1 | 9/2005 | Realyvasquez |
| 2005/0216079 A1 | 9/2005 | MaCoviak |
| 2005/0234508 A1 | 10/2005 | Cummins et al. |
| 2005/0240200 A1 | 10/2005 | Bergheim |
| 2005/0251251 A1 | 11/2005 | Cribier |
| 2005/0267573 A9 | 12/2005 | Macoviak et al. |
| 2006/0004439 A1 | 1/2006 | Spenser et al. |

(56) References Cited

U.S. PATENT DOCUMENTS

| | | |
|---|---|---|
| 2006/0015171 A1 | 1/2006 | Armstrong |
| 2006/0020327 A1 | 1/2006 | Lashinski et al. |
| 2006/0020333 A1 | 1/2006 | Lashinski |
| 2006/0041189 A1 | 2/2006 | Vancaillie |
| 2006/0047297 A1 | 3/2006 | Case |
| 2006/0052867 A1* | 3/2006 | Revuelta ............... A61F 2/2418 623/2.18 |
| 2006/0089627 A1 | 4/2006 | Burnett et al. |
| 2006/0111773 A1 | 5/2006 | Rittgers et al. |
| 2006/0116750 A1 | 6/2006 | Hebert et al. |
| 2006/0135964 A1 | 6/2006 | Vesely |
| 2006/0155357 A1 | 7/2006 | Melsheimer |
| 2006/0178700 A1 | 8/2006 | Quinn |
| 2006/0178740 A1 | 8/2006 | Stacchino et al. |
| 2006/0190036 A1 | 8/2006 | Wendel et al. |
| 2006/0190038 A1 | 8/2006 | Carley et al. |
| 2006/0195183 A1 | 8/2006 | Navia et al. |
| 2006/0195184 A1 | 8/2006 | Lane et al. |
| 2006/0201519 A1 | 9/2006 | Frazier et al. |
| 2006/0212111 A1 | 9/2006 | Case et al. |
| 2006/0241656 A1 | 10/2006 | Starksen et al. |
| 2006/0241748 A1 | 10/2006 | Lee et al. |
| 2006/0247680 A1 | 11/2006 | Amplatz et al. |
| 2006/0253191 A1 | 11/2006 | Salahieh et al. |
| 2006/0259136 A1 | 11/2006 | Nguyen et al. |
| 2006/0259137 A1 | 11/2006 | Artof et al. |
| 2006/0271166 A1 | 11/2006 | Thill et al. |
| 2006/0271171 A1 | 11/2006 | McQuinn et al. |
| 2006/0287719 A1 | 12/2006 | Rowe et al. |
| 2007/0016288 A1 | 1/2007 | Gurskis et al. |
| 2007/0027528 A1 | 2/2007 | Agnew |
| 2007/0027549 A1 | 2/2007 | Godin |
| 2007/0038295 A1 | 2/2007 | Case et al. |
| 2007/0043435 A1 | 2/2007 | Seguin |
| 2007/0055340 A1 | 3/2007 | Pryor |
| 2007/0112422 A1 | 5/2007 | Dehdashtian |
| 2007/0118151 A1 | 5/2007 | Davidson |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0173932 A1 | 7/2007 | Cali et al. |
| 2007/0198077 A1 | 8/2007 | Cully et al. |
| 2007/0198097 A1 | 8/2007 | Zegdi |
| 2007/0213813 A1 | 9/2007 | Von Segesser et al. |
| 2007/0225759 A1 | 9/2007 | Thommen et al. |
| 2007/0225760 A1 | 9/2007 | Moszner et al. |
| 2007/0233186 A1 | 10/2007 | Meng |
| 2007/0233237 A1 | 10/2007 | Krivoruchko |
| 2007/0239272 A1 | 10/2007 | Navia et al. |
| 2007/0255400 A1 | 11/2007 | Parravicini et al. |
| 2008/0004688 A1 | 1/2008 | Spenser et al. |
| 2008/0004697 A1 | 1/2008 | Lichtenstein et al. |
| 2008/0051703 A1 | 2/2008 | Thornton et al. |
| 2008/0071361 A1 | 3/2008 | Tuval et al. |
| 2008/0071363 A1 | 3/2008 | Tuval et al. |
| 2008/0071368 A1 | 3/2008 | Tuval et al. |
| 2008/0071369 A1 | 3/2008 | Tuval et al. |
| 2008/0077235 A1 | 3/2008 | Kirson |
| 2008/0082083 A1 | 4/2008 | Forde et al. |
| 2008/0082159 A1 | 4/2008 | Tseng et al. |
| 2008/0082166 A1 | 4/2008 | Styrc et al. |
| 2008/0086164 A1 | 4/2008 | Rowe |
| 2008/0086204 A1 | 4/2008 | Rankin |
| 2008/0091261 A1 | 4/2008 | Long et al. |
| 2008/0097595 A1 | 4/2008 | Gabbay |
| 2008/0132989 A1 | 6/2008 | Snow |
| 2008/0140003 A1 | 6/2008 | Bei et al. |
| 2008/0161910 A1 | 7/2008 | Revuelta et al. |
| 2008/0167705 A1 | 7/2008 | Agnew |
| 2008/0167714 A1 | 7/2008 | St. Goar et al. |
| 2008/0188929 A1 | 8/2008 | Schreck |
| 2008/0195200 A1 | 8/2008 | Vidlund et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0243245 A1 | 10/2008 | Thambar et al. |
| 2008/0255580 A1 | 10/2008 | Hoffman et al. |
| 2008/0262609 A1 | 10/2008 | Gross et al. |
| 2008/0269879 A1 | 10/2008 | Sathe et al. |
| 2008/0281411 A1 | 11/2008 | Berreklouw |
| 2008/0294234 A1 | 11/2008 | Hartley et al. |
| 2009/0005863 A1 | 1/2009 | Goetz et al. |
| 2009/0036966 A1 | 2/2009 | O'Connor et al. |
| 2009/0054969 A1 | 2/2009 | Salahieh et al. |
| 2009/0088836 A1 | 4/2009 | Bishop et al. |
| 2009/0099554 A1 | 4/2009 | Forster et al. |
| 2009/0099650 A1 | 4/2009 | Bolduc et al. |
| 2009/0112159 A1 | 4/2009 | Slattery et al. |
| 2009/0171363 A1 | 7/2009 | Choeron |
| 2009/0177278 A1 | 7/2009 | Spence |
| 2009/0210052 A1 | 8/2009 | Forster et al. |
| 2009/0222081 A1 | 9/2009 | Linder et al. |
| 2009/0240320 A1 | 9/2009 | Tuval et al. |
| 2009/0241656 A1 | 10/2009 | Jacquemin |
| 2009/0264859 A1 | 10/2009 | Mas |
| 2009/0264994 A1 | 10/2009 | Saadat |
| 2009/0276040 A1 | 11/2009 | Rowe et al. |
| 2009/0281619 A1 | 11/2009 | Le et al. |
| 2009/0287304 A1 | 11/2009 | Dahlgren et al. |
| 2009/0299449 A1 | 12/2009 | Styrc |
| 2009/0306768 A1 | 12/2009 | Quadri et al. |
| 2009/0319037 A1 | 12/2009 | Rowe et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0069852 A1 | 3/2010 | Kelley |
| 2010/0076548 A1 | 3/2010 | Konno |
| 2010/0114299 A1 | 5/2010 | Ben Muvhar et al. |
| 2010/0131054 A1 | 5/2010 | Tuval et al. |
| 2010/0137979 A1 | 6/2010 | Tuval et al. |
| 2010/0160958 A1 | 6/2010 | Clark |
| 2010/0161036 A1 | 6/2010 | Pinter et al. |
| 2010/0161042 A1 | 6/2010 | Maisano et al. |
| 2010/0174363 A1 | 7/2010 | Castro |
| 2010/0179643 A1 | 7/2010 | Shalev |
| 2010/0179648 A1 | 7/2010 | Richter et al. |
| 2010/0179649 A1 | 7/2010 | Richter et al. |
| 2010/0217382 A1 | 8/2010 | Chau et al. |
| 2010/0222810 A1 | 9/2010 | DeBeer et al. |
| 2010/0228285 A1 | 9/2010 | Miles et al. |
| 2010/0234940 A1 | 9/2010 | Dolan |
| 2010/0249908 A1 | 9/2010 | Chau et al. |
| 2010/0249917 A1 | 9/2010 | Zhang |
| 2010/0256737 A1 | 10/2010 | Pollock et al. |
| 2010/0262232 A1 | 10/2010 | Annest |
| 2010/0280603 A1 | 11/2010 | Maisano et al. |
| 2010/0280606 A1 | 11/2010 | Naor |
| 2010/0312333 A1 | 12/2010 | Navia et al. |
| 2010/0324595 A1 | 12/2010 | Linder et al. |
| 2010/0331971 A1 | 12/2010 | Keranen et al. |
| 2011/0004296 A1 | 1/2011 | Lutter et al. |
| 2011/0015729 A1 | 1/2011 | Jimenez et al. |
| 2011/0015731 A1 | 1/2011 | Carpentier et al. |
| 2011/0022165 A1 | 1/2011 | Oba et al. |
| 2011/0040374 A1 | 2/2011 | Goetz et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0071626 A1 | 3/2011 | Wright et al. |
| 2011/0077730 A1 | 3/2011 | Fenster |
| 2011/0082538 A1 | 4/2011 | Dahlgren et al. |
| 2011/0087322 A1 | 4/2011 | Letac et al. |
| 2011/0093063 A1 | 4/2011 | Schreck |
| 2011/0098525 A1 | 4/2011 | Kermode et al. |
| 2011/0106247 A1 | 5/2011 | Miller et al. |
| 2011/0112625 A1 | 5/2011 | Ben-Muvhar et al. |
| 2011/0112632 A1 | 5/2011 | Chau et al. |
| 2011/0118830 A1 | 5/2011 | Liddicoat et al. |
| 2011/0125257 A1 | 5/2011 | Seguin et al. |
| 2011/0125258 A1 | 5/2011 | Centola |
| 2011/0137326 A1 | 6/2011 | Bachman |
| 2011/0137397 A1 | 6/2011 | Chau et al. |

(56) References Cited

U.S. PATENT DOCUMENTS

| | | |
|---|---|---|
| 2011/0137409 A1 | 6/2011 | Yang et al. |
| 2011/0137410 A1 | 6/2011 | Hacohen |
| 2011/0144742 A1 | 6/2011 | Madrid et al. |
| 2011/0166636 A1 | 7/2011 | Rowe |
| 2011/0172784 A1 | 7/2011 | Richter et al. |
| 2011/0178597 A9 | 7/2011 | Navia et al. |
| 2011/0184510 A1 | 7/2011 | Maisano et al. |
| 2011/0190877 A1 | 8/2011 | Lane et al. |
| 2011/0190879 A1 | 8/2011 | Bobo et al. |
| 2011/0202076 A1 | 8/2011 | Richter |
| 2011/0208283 A1 | 8/2011 | Rust |
| 2011/0208293 A1 | 8/2011 | Tabor |
| 2011/0208298 A1 | 8/2011 | Tuval et al. |
| 2011/0213459 A1 | 9/2011 | Garrison et al. |
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1 | 9/2011 | Hacohen |
| 2011/0238159 A1 | 9/2011 | Guyenot et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251678 A1 | 10/2011 | Eidenschink et al. |
| 2011/0251679 A1 | 10/2011 | Wiemeyer et al. |
| 2011/0251680 A1 | 10/2011 | Tran et al. |
| 2011/0251682 A1 | 10/2011 | Murray, III et al. |
| 2011/0251683 A1 | 10/2011 | Tabor |
| 2011/0257721 A1 | 10/2011 | Tabor |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung et al. |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy et al. |
| 2011/0270276 A1 | 11/2011 | Rothstein et al. |
| 2011/0271967 A1 | 11/2011 | Mortier et al. |
| 2011/0282438 A1 | 11/2011 | Drews et al. |
| 2011/0282439 A1 | 11/2011 | Thill et al. |
| 2011/0282440 A1 | 11/2011 | Cao et al. |
| 2011/0283514 A1 | 11/2011 | Fogarty et al. |
| 2011/0288634 A1 | 11/2011 | Tuval et al. |
| 2011/0295354 A1 | 12/2011 | Bueche et al. |
| 2011/0295363 A1 | 12/2011 | Girard et al. |
| 2011/0301688 A1 | 12/2011 | Dolan |
| 2011/0301701 A1 | 12/2011 | Padala et al. |
| 2011/0301702 A1 | 12/2011 | Rust et al. |
| 2011/0313452 A1 | 12/2011 | Carley et al. |
| 2011/0313515 A1 | 12/2011 | Quadri et al. |
| 2011/0319989 A1 | 12/2011 | Lane et al. |
| 2011/0319991 A1 | 12/2011 | Hariton et al. |
| 2012/0010694 A1 | 1/2012 | Litter et al. |
| 2012/0022633 A1 | 1/2012 | Olson et al. |
| 2012/0022637 A1 | 1/2012 | Ben-Muvhar |
| 2012/0022639 A1 | 1/2012 | Hacohen et al. |
| 2012/0022640 A1 | 1/2012 | Gross et al. |
| 2012/0035703 A1 | 2/2012 | Lutter et al. |
| 2012/0035713 A1 | 2/2012 | Lattere et al. |
| 2012/0035722 A1 | 2/2012 | Tuval |
| 2012/0040742 A1 | 2/2012 | Tuyal et al. |
| 2012/0041547 A1 | 2/2012 | Duffy et al. |
| 2012/0041551 A1 | 2/2012 | Spenser et al. |
| 2012/0046735 A1 | 2/2012 | Lau et al. |
| 2012/0053652 A1 | 3/2012 | Kovalsky et al. |
| 2012/0053676 A1 | 3/2012 | Ku et al. |
| 2012/0053688 A1 | 3/2012 | Fogarty et al. |
| 2012/0059454 A1 | 3/2012 | Millwee et al. |
| 2012/0078237 A1 | 3/2012 | Wang et al. |
| 2012/0078353 A1 | 3/2012 | Quadri et al. |
| 2012/0078357 A1 | 3/2012 | Conklin |
| 2012/0083832 A1 | 4/2012 | Delaloye et al. |
| 2012/0083839 A1 | 4/2012 | Letac et al. |
| 2012/0083879 A1 | 4/2012 | Eberhardt et al. |
| 2012/0089223 A1 | 4/2012 | Nguyen et al. |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0123511 A1 | 5/2012 | Brown |
| 2012/0123530 A1 | 5/2012 | Carpentier et al. |
| 2012/0130473 A1 | 5/2012 | Norris et al. |
| 2012/0130474 A1 | 5/2012 | Buckley |
| 2012/0130475 A1 | 5/2012 | Shaw |
| 2012/0136434 A1 | 5/2012 | Carpentier et al. |
| 2012/0150218 A1 | 6/2012 | Sandgren et al. |
| 2012/0165915 A1 | 6/2012 | Melsheimer et al. |
| 2012/0179244 A1 | 7/2012 | Schankereli et al. |
| 2012/0197292 A1 | 8/2012 | Chin-Chen et al. |
| 2012/0283824 A1 | 11/2012 | Lutter et al. |
| 2012/0290062 A1 | 11/2012 | McNamara et al. |
| 2012/0296360 A1 | 11/2012 | Norris et al. |
| 2012/0300063 A1 | 11/2012 | Majkrzak et al. |
| 2012/0310328 A1 | 12/2012 | Olson et al. |
| 2012/0323316 A1 | 12/2012 | Chau et al. |
| 2012/0330408 A1 | 12/2012 | Hillukka et al. |
| 2013/0006347 A1 | 1/2013 | McHugo |
| 2013/0018450 A1 | 1/2013 | Hunt |
| 2013/0018458 A1 | 1/2013 | Yohanan et al. |
| 2013/0035759 A1 | 2/2013 | Gross et al. |
| 2013/0041451 A1 | 2/2013 | Patterson et al. |
| 2013/0046373 A1 | 2/2013 | Cartledge et al. |
| 2013/0079872 A1 | 3/2013 | Gallagher |
| 2013/0116780 A1 | 5/2013 | Miller et al. |
| 2013/0123896 A1 | 5/2013 | Bloss et al. |
| 2013/0123900 A1 | 5/2013 | Eblacas et al. |
| 2013/0144381 A1 | 6/2013 | Quadri et al. |
| 2013/0150945 A1 | 6/2013 | Crawford et al. |
| 2013/0150956 A1 | 6/2013 | Yohanan et al. |
| 2013/0158647 A1 | 6/2013 | Norris et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0172992 A1 | 7/2013 | Gross et al. |
| 2013/0190861 A1 | 7/2013 | Chau et al. |
| 2013/0211501 A1 | 8/2013 | Buckley et al. |
| 2013/0245742 A1 | 9/2013 | Norris |
| 2013/0261737 A1 | 10/2013 | Costello |
| 2013/0289711 A1 | 10/2013 | Liddy et al. |
| 2013/0297013 A1 | 11/2013 | Klima et al. |
| 2013/0304197 A1 | 11/2013 | Buchbinder et al. |
| 2013/0304200 A1 | 11/2013 | McLean et al. |
| 2013/0310928 A1 | 11/2013 | Morriss et al. |
| 2013/0325114 A1 | 12/2013 | McLean et al. |
| 2013/0331929 A1 | 12/2013 | Mitra et al. |
| 2014/0005778 A1 | 1/2014 | Buchbinder et al. |
| 2014/0018911 A1 | 1/2014 | Zhou et al. |
| 2014/0031928 A1 | 1/2014 | Murphy et al. |
| 2014/0046430 A1 | 2/2014 | Shaw |
| 2014/0052237 A1 | 2/2014 | Lane et al. |
| 2014/0067054 A1 | 3/2014 | Chau et al. |
| 2014/0081376 A1 | 3/2014 | Burkart et al. |
| 2014/0106951 A1 | 4/2014 | Brandon |
| 2014/0120287 A1 | 5/2014 | Jacoby et al. |
| 2014/0121749 A1 | 5/2014 | Roeder |
| 2014/0121763 A1 | 5/2014 | Duffy et al. |
| 2014/0135695 A1 | 5/2014 | Andress et al. |
| 2014/0135894 A1 | 5/2014 | Norris et al. |
| 2014/0142681 A1 | 5/2014 | Norris |
| 2014/0148891 A1 | 5/2014 | Johnson |
| 2014/0163690 A1 | 6/2014 | White |
| 2014/0172069 A1 | 6/2014 | Roeder et al. |
| 2014/0172077 A1 | 6/2014 | Bruchman et al. |
| 2014/0172082 A1 | 6/2014 | Bruchman et al. |
| 2014/0188210 A1 | 7/2014 | Beard et al. |
| 2014/0188221 A1 | 7/2014 | Chung et al. |
| 2014/0194981 A1 | 7/2014 | Menk et al. |
| 2014/0194983 A1 | 7/2014 | Kovalsky et al. |
| 2014/0207231 A1 | 7/2014 | Hacohen et al. |

(56) References Cited

U.S. PATENT DOCUMENTS

| | | |
|---|---|---|
| 2014/0214159 A1 | 7/2014 | Vidlund et al. |
| 2014/0222136 A1 | 8/2014 | Geist et al. |
| 2014/0249622 A1 | 9/2014 | Carmi et al. |
| 2014/0257461 A1 | 9/2014 | Robinson et al. |
| 2014/0257467 A1 | 9/2014 | Lane et al. |
| 2014/0257475 A1 | 9/2014 | Gross et al. |
| 2014/0257476 A1 | 9/2014 | Montorfano et al. |
| 2014/0277353 A1 | 9/2014 | Siazas |
| 2014/0277409 A1 | 9/2014 | Bortlein et al. |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296962 A1 | 10/2014 | Cartledge et al. |
| 2014/0296969 A1 | 10/2014 | Tegels et al. |
| 2014/0324164 A1 | 10/2014 | Gross et al. |
| 2014/0336744 A1 | 11/2014 | Tani et al. |
| 2014/0343670 A1 | 11/2014 | Bakis et al. |
| 2014/0358224 A1 | 12/2014 | Tegels et al. |
| 2014/0379065 A1 | 12/2014 | Johnson et al. |
| 2014/0379074 A1 | 12/2014 | Spence et al. |
| 2014/0379076 A1 | 12/2014 | Vidlund et al. |
| 2015/0018944 A1 | 1/2015 | O'Connell et al. |
| 2015/0045881 A1 | 2/2015 | Lim |
| 2015/0094802 A1 | 4/2015 | Buchbinder et al. |
| 2015/0119970 A1 | 4/2015 | Nakayama et al. |
| 2015/0127097 A1 | 5/2015 | Neumann et al. |
| 2015/0142100 A1 | 5/2015 | Morriss et al. |
| 2015/0142103 A1 | 5/2015 | Vidlund |
| 2015/0157457 A1 | 6/2015 | Hacohen |
| 2015/0173896 A1 | 6/2015 | Richter et al. |
| 2015/0173897 A1 | 6/2015 | Raanani et al. |
| 2015/0164640 A1 | 8/2015 | McLean et al. |
| 2015/0216661 A1 | 8/2015 | Hacohen et al. |
| 2015/0238313 A1 | 8/2015 | Spence et al. |
| 2015/0245934 A1 | 9/2015 | Lombardi et al. |
| 2015/0272730 A1 | 10/2015 | Melnick et al. |
| 2015/0282964 A1 | 10/2015 | Beard et al. |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0351903 A1 | 12/2015 | Morriss et al. |
| 2015/0351904 A1 | 12/2015 | Cooper et al. |
| 2015/0359629 A1 | 12/2015 | Ganesan et al. |
| 2015/0359631 A1 | 12/2015 | Sheahan et al. |
| 2016/0030169 A1 | 2/2016 | Shahriari |
| 2016/0030171 A1 | 2/2016 | Quijano et al. |
| 2016/0095700 A1 | 4/2016 | Righini |
| 2016/0106539 A1 | 4/2016 | Buchbinder et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0184098 A1 | 6/2016 | Vaturi |
| 2016/0220367 A1 | 8/2016 | Barrett |
| 2016/0228247 A1 | 8/2016 | Maimon et al. |
| 2016/0242902 A1 | 8/2016 | Morriss et al. |
| 2016/0270911 A1 | 9/2016 | Ganesan et al. |
| 2016/0310268 A1 | 10/2016 | Oba et al. |
| 2016/0310274 A1 | 10/2016 | Gross et al. |
| 2016/0317301 A1 | 11/2016 | Quadri et al. |
| 2016/0324633 A1 | 11/2016 | Gross et al. |
| 2016/0324640 A1 | 11/2016 | Gifford, III et al. |
| 2016/0331525 A1 | 11/2016 | Straubinger et al. |
| 2016/0331526 A1 | 11/2016 | Schweich, Jr. et al. |
| 2016/0367360 A1 | 12/2016 | Cartledge et al. |
| 2016/0367368 A1 | 12/2016 | Vidlund et al. |
| 2017/0042678 A1 | 2/2017 | Ganesan et al. |
| 2017/0056171 A1 | 3/2017 | Cooper et al. |
| 2017/0128205 A1 | 5/2017 | Tamir et al. |
| 2017/0196688 A1 | 7/2017 | Christianson et al. |
| 2017/0196692 A1 | 7/2017 | Kirk et al. |
| 2017/0209264 A1 | 7/2017 | Chau et al. |
| 2017/0216026 A1 | 8/2017 | Quill et al. |
| 2017/0231759 A1 | 8/2017 | Geist et al. |
| 2017/0231760 A1 | 8/2017 | Lane et al. |
| 2018/0049873 A1 | 2/2018 | Manash et al. |
| 2018/0055628 A1 | 3/2018 | Patel et al. |
| 2018/0055630 A1 | 3/2018 | Patel et al. |
| 2018/0153689 A1 | 6/2018 | Maimon et al. |
| 2018/0177594 A1 | 6/2018 | Patel et al. |
| 2018/0250130 A1 | 9/2018 | Hariton et al. |
| 2018/0256323 A1 | 9/2018 | Hariton et al. |
| 2018/0256325 A1 | 9/2018 | Hariton et al. |
| 2018/0271654 A1 | 9/2018 | Hariton et al. |
| 2018/0271655 A1 | 9/2018 | Hariton et al. |
| 2018/0289479 A1 | 10/2018 | Hariton et al. |

FOREIGN PATENT DOCUMENTS

| | | | |
|---|---|---|---|
| WO | 98/43557 A1 | 10/1998 | |
| WO | 99/30647 A1 | 6/1999 | |
| WO | 00/47139 A1 | 8/2000 | |
| WO | 01/62189 A1 | 8/2001 | |
| WO | 01/87190 A2 | 11/2001 | |
| WO | 03/028558 A2 | 4/2003 | |
| WO | 2006/007401 A2 | 1/2006 | |
| WO | 2006/054930 A1 | 5/2006 | |
| WO | 2006/070372 A2 | 7/2006 | |
| WO | 2006/089236 A1 | 8/2006 | |
| WO | 2007/059252 A1 | 5/2007 | |
| WO | 2008/013915 A3 | 1/2008 | |
| WO | 2008/029296 A2 | 3/2008 | |
| WO | WO 2008/029296 A2 | 3/2008 | |
| WO | 2008/070797 A2 | 6/2008 | |
| WO | 2008/103722 A2 | 8/2008 | |
| WO | 2009/033469 A1 | 3/2009 | |
| WO | 2009/053497 A1 | 4/2009 | |
| WO | 2009/091509 A1 | 7/2009 | |
| WO | 2010/006627 A1 | 1/2010 | |
| WO | WO 2010057262 A1 * | 5/2010 | ......... A61B 17/0057 |
| WO | 2010/073246 A2 | 7/2010 | |
| WO | 2010/081033 A1 | 7/2010 | |
| WO | 2011/025972 A2 | 3/2011 | |
| WO | 2011/069048 A2 | 6/2011 | |
| WO | 2011/106137 A1 | 9/2011 | |
| WO | 2011/111047 A2 | 9/2011 | |
| WO | 2011/137531 A1 | 11/2011 | |
| WO | 2011/143263 A2 | 11/2011 | |
| WO | 2011/154942 A2 | 12/2011 | |
| WO | 2012/011108 A2 | 1/2012 | |
| WO | 2012/024428 A2 | 2/2012 | |
| WO | 2012/036740 A2 | 3/2012 | |
| WO | WO 2012/036740 A2 | 3/2012 | |
| WO | 2012/127309 A1 | 9/2012 | |
| WO | 2012/177942 A2 | 12/2012 | |
| WO | 2013/021374 A2 | 2/2013 | |
| WO | 2013/021375 A2 | 2/2013 | |
| WO | 2013/021384 A1 | 2/2013 | |
| WO | 2013/059747 A1 | 4/2013 | |
| WO | WO 2013/059747 A1 | 4/2013 | |
| WO | 2013/078497 A1 | 6/2013 | |
| WO | 2013/128436 A1 | 6/2013 | |
| WO | 2014/022124 A1 | 2/2014 | |
| WO | 2014/145338 A1 | 9/2014 | |
| WO | 2014/164364 A1 | 10/2014 | |
| WO | WO 2014/164364 A1 | 10/2014 | |
| WO | 2015/173794 A1 | 11/2015 | |
| WO | 2016/093877 A1 | 6/2016 | |
| WO | WO 2016/098104 A2 | 6/2016 | |
| WO | WO 2016/125160 A1 | 8/2016 | |
| WO | 2017/223486 A1 | 12/2017 | |
| WO | 2018/025260 A1 | 2/2018 | |
| WO | WO 2018/025260 A1 | 2/2018 | |
| WO | 2018/106837 A1 | 6/2018 | |
| WO | 2018/112429 A1 | 6/2018 | |
| WO | 2018/118717 A1 | 6/2018 | |
| WO | WO 2018/106837 A1 | 6/2018 | |
| WO | WO 2018/112429 A1 | 6/2018 | |
| WO | WO 2018/118717 A1 | 6/2018 | |
| WO | 2018/131042 A1 | 7/2018 | |
| WO | 2018/131043 A1 | 7/2018 | |

(56) References Cited

FOREIGN PATENT DOCUMENTS

| WO | WO 2018/131042 A1 | 7/2018 |
|---|---|---|
| WO | WO 2018/131043 A1 | 7/2018 |

OTHER PUBLICATIONS

An Office Action dated Jun. 18, 2018, which issued during the prosecution of UK Patent Application No. 1800399.6.
An International Search Report and a Written Opinion both dated Jun. 20, 2018, which issued during the prosecution of Applicant's PCT/IL2018/050024.
USPTO AA dated Apr. 2, 2018 in connection with U.S. Appl. No. 14/736,004.
USPTO RR dated May 4, 2018 in connection with U.S. Appl. No. 15/872,501.
USPTO NFOA dated Jul. 26, 2018 in connection with U.S. Appl. No. 15/872,501.
USPTO NOA mailed Apr. 20, 2018 in connection with U.S. Appl. No. 15/878,206.
USPTO NFOA dated Apr. 20, 2018 in connection with U.S. Appl. No. 15/886,517.
USPTO NFOA dated Aug. 9, 2018 in connection with U.S. Appl. No. 15/899,858.
USPTO NFOA dated Aug. 9, 2018 in connection with U.S. Appl. No. 15/002,403.
USPTO NFOA dated Jun. 28, 2018 in connection with U.S. Appl. No. 29/635,658.
USPTO NFOA dated Jun. 28, 2018 in connection with U.S. Appl. No. 29/635,661.
USPTO NFOA dated Oct. 23, 2017 in connection with U.S. Appl. No. 14/763,004.
USPTO FOA dated Jan. 17, 2018 in connection with U.S. Appl. No. 14/763,004.
USPTO NFOA dated Feb. 7, 2018 in connection with U.S. Appl. No. 15/197,069.
USPTO NFOA dated Dec. 7, 2017 in connection with U.S. Appl. No. 15/213,791.
Interview Summary dated Feb. 8, 2018 in connection with U.S. Appl. No. 15/213,791.
USPTO NFOA dated Jan. 5, 2018 in connection with U.S. Appl. No. 15/541,783.
USPTO NFOA dated Feb. 2, 2018 in connection with U.S. Appl. No. 15/329,920.
Invitation to pay additional fees dated Jan. 2, 2018; PCT/IL2017/050849.
Invitation to Pay Additional Fees, dated Jun. 12, 2014; PCT/IL2014/050087.
Invitation to Pay Additional Fees, dated Sep. 29, 2017; PCT/IL2017/050873.
EESR dated Jun. 29, 2017; Appln. 11809374.9.
EESR dated Feb. 18, 2015; Appln. 12821522.5.
EPO Office Action dated Feb. 10, 2017; Appln. 12821522.5.
Great Britain Office Action dated Feb. 7, 2017; Appln. GB1613219.3.
IPRP dated Dec. 2, 2013; PCT/IL2011/000582.
IPRP dated Sep. 11, 2012; PCT/IL2011/000231.
IPRP dated Feb. 11, 2014; PCT/IL2012/000292.
IPRP dated Feb. 11, 2014 PCT/IL2012/000293.
ISR and WO dated Dec. 5, 2011; PCT/IL11/00582.
ISR and WO dated Mar. 17, 2014; PCT/IL13/50937.
ISR and WO dated Oct. 13, 2011; PCT/IL11/00231.
ISR and WO dated Feb. 6, 2013; PCT/IL2012/000292.
ISR and WO dated Feb. 6, 2013; PCT/Il2012/000293.
ISR and WO dated Sep. 4, 2014; PCT/IL2014/050087.
ISR and WO dated Oct. 27, 2015; PCT/IL2015/050792.
ISR and WO dated May 30, 2016; PCT/IL2016/050125.
Alexander Geha, et al; "Replacement of Degenerated Mitral and Aortic Bioprostheses Without Explantaton", Ann. Thorac Surg. Jun. 2001; 72: 1509-1514.

Dominque Himbert MD; "Mitral Regurgitation and Stenosis from Bioprosthesis and Annuloplast Failure Transcatheter Approaches and Outcomes", 24 pages, Oct. 28, 2013.
Saturn Project; A Novel Solution for Transcatheter Hear Valve Replacement Specifically Designed to Address Clinical Therapeutic Needs on Mitral Valve; Dec. 2016; 8 pages.
Frank Langer MD, et al; RING plus STRING: "Papillary Muscle Repositioning as an Adjunctive Repair Technique for Ischemic Mitral Regurgitation", J. Thoracic Cardiovasc. Surg. 133: 247-9, Jan. 2007.
Frank Langer MD, et al; "RING+STRING Successful Repair Technique for Ischemic Mitral Regurgitation With Severe Leaflet Tethering", Circulation 120[Suppl 1]: S85-S91, Sep. 2009.
Francesco Maisano, MD: "Valvetech Cardiovalve: Novel Design Feature and Clinical Update" 2015; TCR Presentation re Cardiovalave; 10 pages.
Giovanni Righini; Righini presentation EuroPCR May 2015 (Saturn)- downloaded from: https://www.pcronline.com/Cases-resourceimages/ Resources/Course-videos-slides/2015/Cardiovascularinnovaton- pipeline-Mitral-and-tricuspid-valve-interventions).
John G Webb, et al; "Transcatheter Valve-in-Valve Implantation for Failed Bioprosthetic Heart Valves", Circulation 2010; 1121;1848-1847; originally published online Apr. 12, 2010.
S. Willeke, et al; "Detachable shape-memory sewing ring for heart valves", Artificial Organs, 16:294-297; 1992 (an abstract).
U.S. Appl. No. 61/283,819.
U.S. Appl. No. 61/492,449.
U.S. Appl. No. 61/515,372.
U.S. Appl. No. 61/525,281.
U.S. Appl. No. 61/537,276.
U.S. Appl. No. 61/555,160.
U.S. Appl. No. 61/588,892.
USPTO FOA dated Feb. 10, 2014; U.S. Appl. No. 13/033,852.
USPTO FOA dated Feb. 15, 2013; U.S. Appl. No. 12/840,463.
USPTO FOA dated Feb. 25, 2016; U.S. Appl. No. 14/522,987.
USPTO FOA dated Mar. 25, 2015; U.S. Appl. No. 12/840,463.
USPTO FOA dated Apr. 13, 2016; U.S. Appl. No. 14/626,267.
USPTO FOA dated May 23, 2014; U.S. Appl. No. 13/412,814.
USPTO FOA dated Jul. 18, 2013; U.S. Appl. No. 13/044,694.
USPTO FOA dated Jul. 23, 2013; U.S. Appl. No. 13/961,721.
USPTO FOA dated Sep. 12, 2013; U.S. Appl. No. 13/412,814.
USPTO NFOA dated Jan. 18, 2017; U.S. Appl. No. 14/626,267.
USPTO NFOA dated Jan. 21, 2016; U.S. Appl. No. 14/237,264.
USPTO NFOA dated Feb. 6, 2013; U.S. Appl. No. 13/412,814.
USPTO NFOA dated Feb. 7, 2017; U.S. Appl. No. 14/689,608.
USPTO NFOA dated Jun. 4, 2014; U.S. Appl. No. 12/840,463.
USPTO NFOA dated Jun. 17, 2014; U.S. Appl. No. 12/961,721.
USPTO NFOA dated Jun. 30, 2015; U.S. Appl. No. 14/522,987.
USPTO NFOA dated Jul. 2, 2014; U.S. Appl. No. 13/811,308.
USPTO NFOA dated Jul. 3, 2014; U.S. Appl. No. 13/033,852.
USPTO NFOA dated Aug. 2, 2013; U.S. Appl. No. 13/033,852.
USPTO NFOA dated Sep. 19, 2014; U.S. Appl. No. 13/044,694.
USPTO NFOA dated Nov. 8, 2013; U.S. Appl. No. 12/840,463.
USPTO NFOA dated Nov. 23, 2012; U.S. Appl. No. 13/033,852.
USPTO NFOA dated Nov. 27, 2015; U.S. Appl. No. 14/626,267.
USPTO NFOA dated Nov. 28, 2012; U.S. Appl. No. 12/961,721.
USPTO NFOA dated Dec. 10, 2015; U.S. Appl. No. 14/237,258.
USPTO NFOA dated Dec. 31, 2012; U.S. Appl. No. 13/044,694.
USPTO NFOA dated May 29, 2012; U.S. Appl. No. 12/840,463.
USPTO NOA dated May 20, 2016; U.S. Appl. No. 14/237,258.
USPTO NOA dated Jul. 6, 2017; U.S. Appl. No. 14/689,608.
USPTO NOA dated Aug. 18, 2017; U.S. Appl. No. 14/689,608.
USPTO NOA mailed Feb. 11, 2015; U.S. Appl. No. 13/033,852.
USPTO NOA mailed Mar. 10, 2015; U.S. Appl. No. 13/811,308.
USPTO NOA mailed Apr. 8, 2016; U.S. Appl. No. 14/237,258.
USPTO NOA mailed May 5, 2015; U.S. Appl. No. 12/840,463.
USPTO NOA dated May 10, 2016; U.S. Appl. No. 14/237,258.
USPTO NOA dated May 22, 2017; U.S. Appl. No. 14/689,608.
USPTO NOA dated Aug. 15, 2014; U.S. Appl. No. 13/412,814.
USPTO RR dated Jan. 20, 2016; U.S. Appl. No. 14/161,921.
USPTO RR dated Feb. 3, 2014; U.S. Appl. No. 13/811,308.
USPTO RR dated Apr. 21, 2017; U.S. Appl. No. 15/213,791.
USPTO RR dated Jul. 2, 2012; U.S. Appl. No. 13/033,852.

(56) References Cited

OTHER PUBLICATIONS

USPTO RR dated Aug. 13, 2012; U.S. Appl. No. 13/044,694.
USPTO RR dated Aug. 14, 2012; U.S. Appl. No. 12/961,721.
USPTO RR dated Aug. 28, 2015; U.S. Appl. No. 14/237,264.
USPTO RR dated Sep. 26, 2016; U.S. Appl. No. 14/763,004.
International Search Report dated Dec. 5, 2011, by the United States Patent and Trademark Office in PCT/IL2011/000582 (3 pages).
Written Opinion of the International Searching Authority dated Dec. 5, 2011, by the United States Patent and Trademark Office in PCT/IL2011/000582 (12 pages).

* cited by examiner

FIG. 3A
FIG. 3B
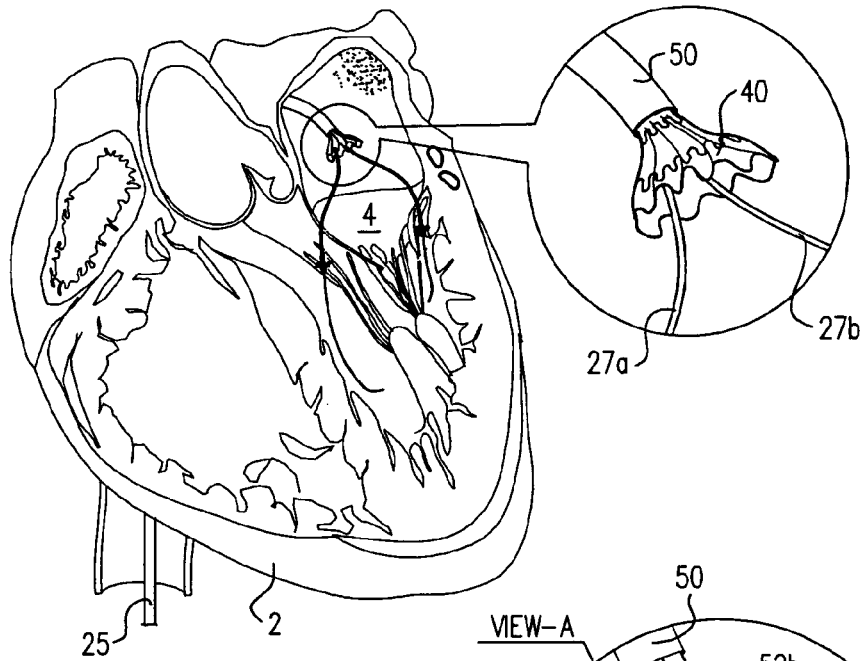
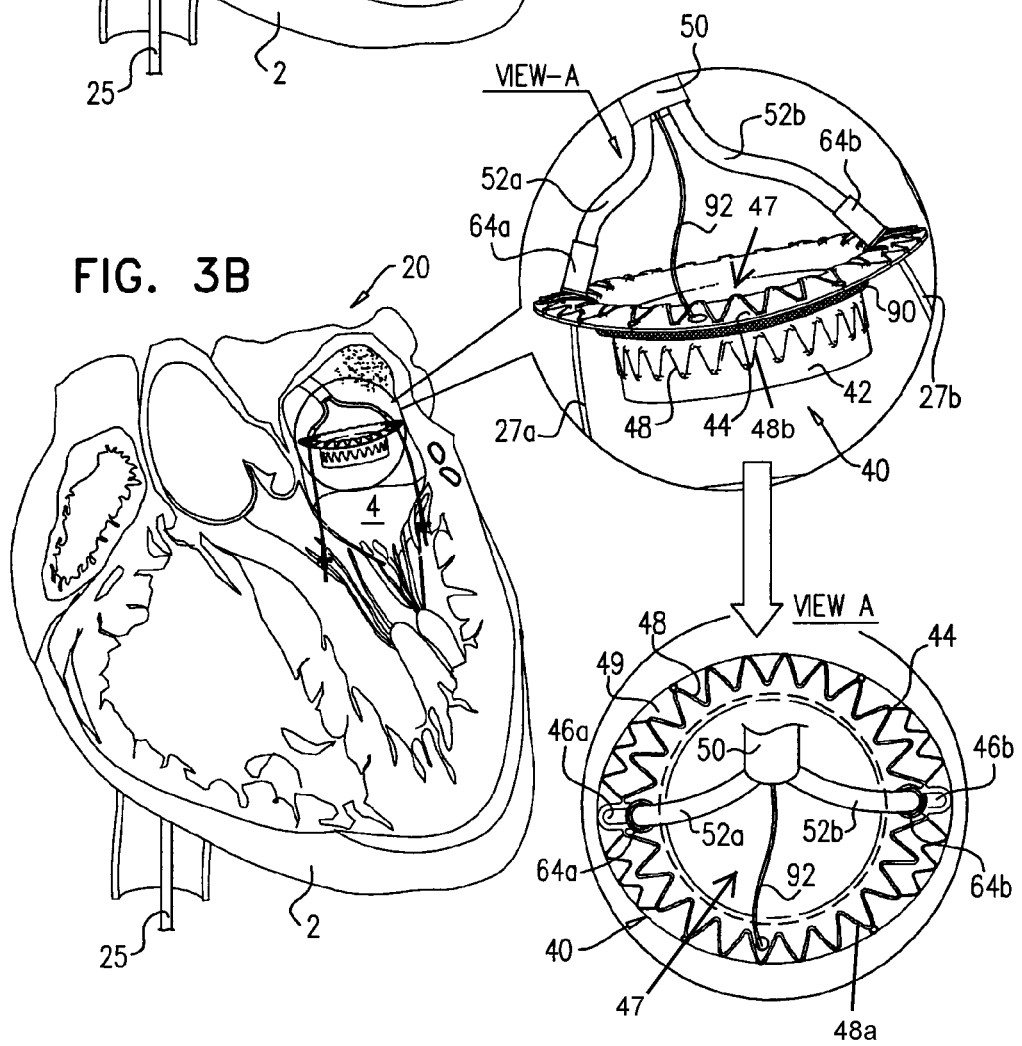

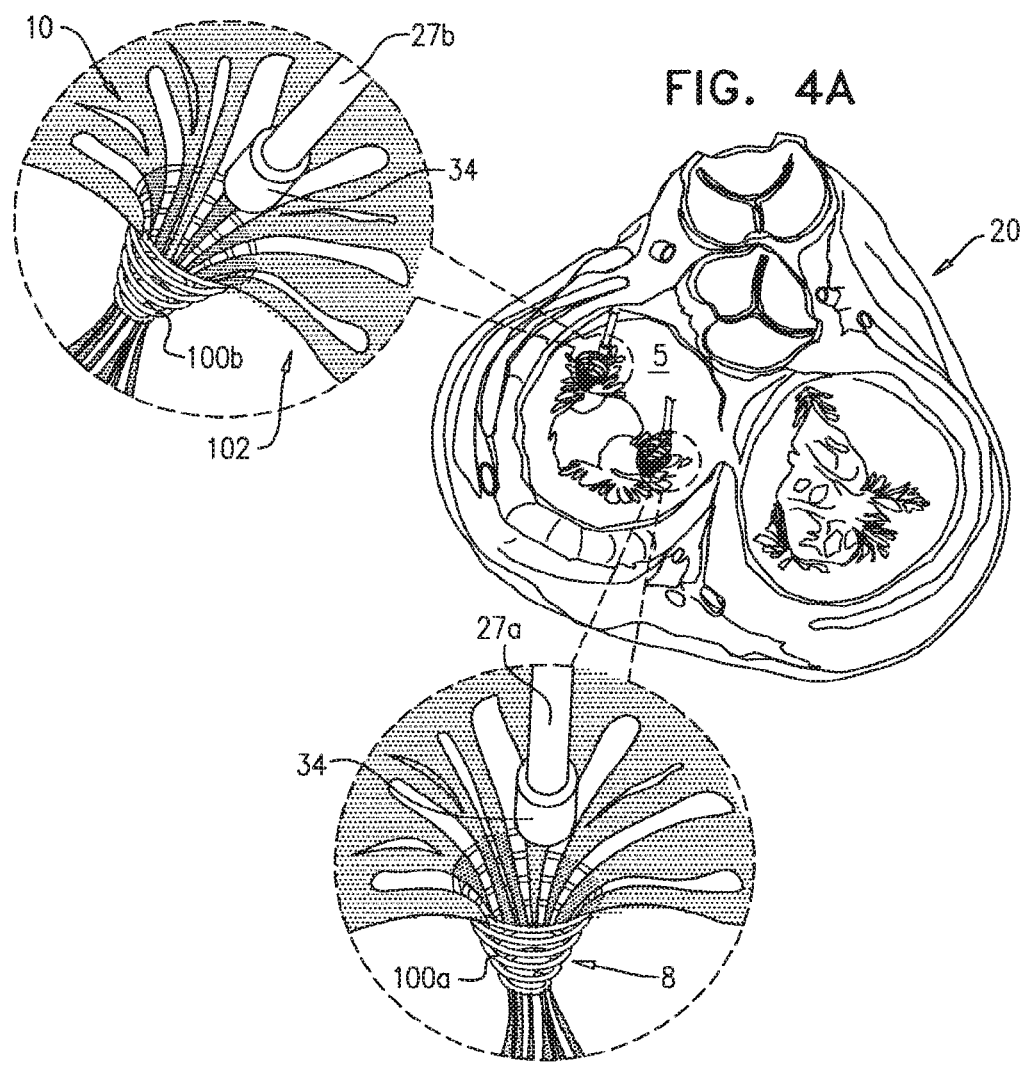

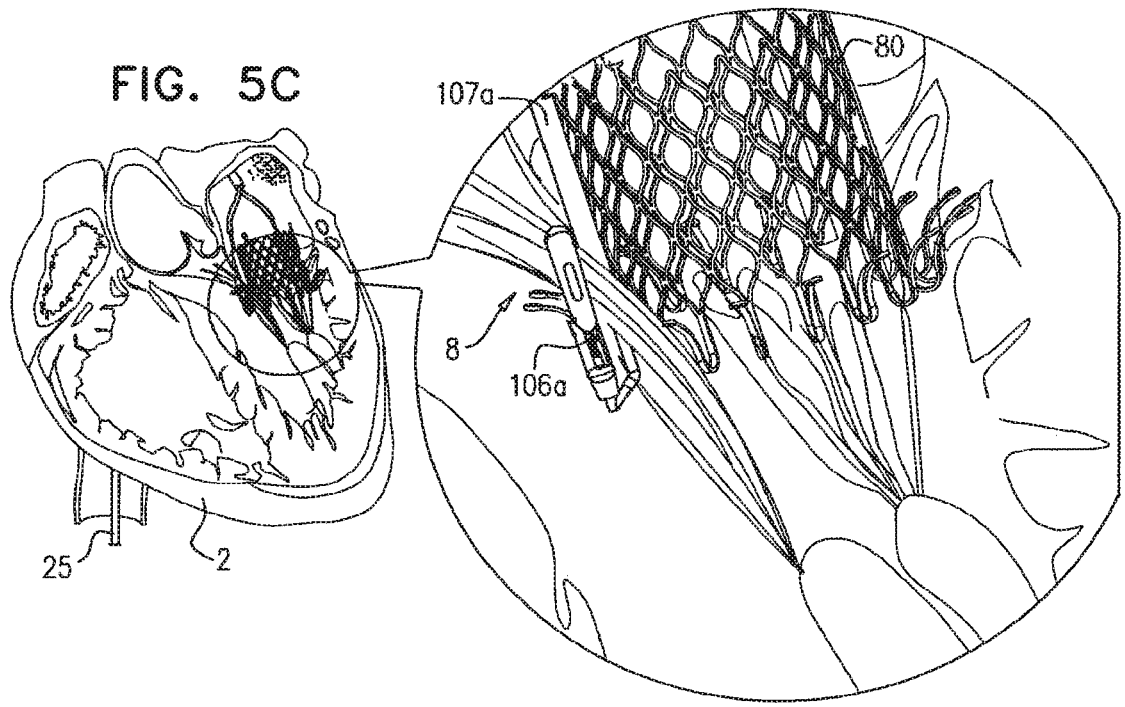
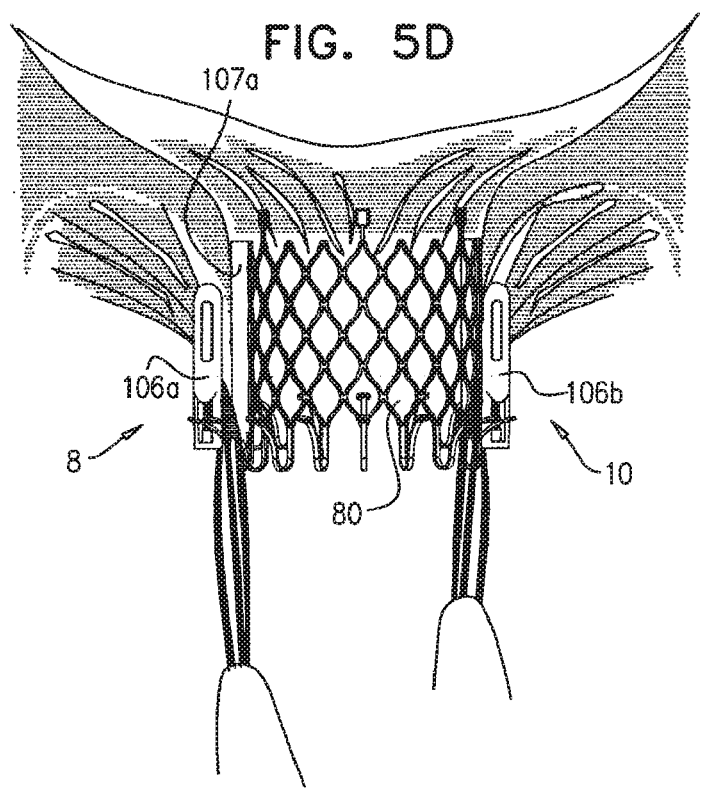

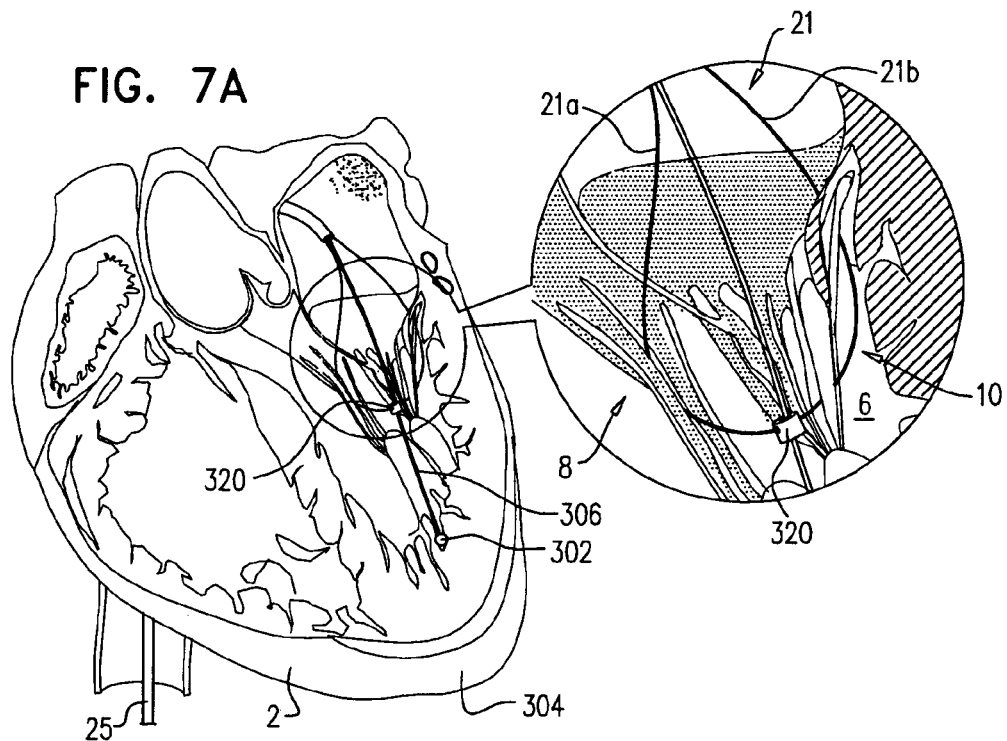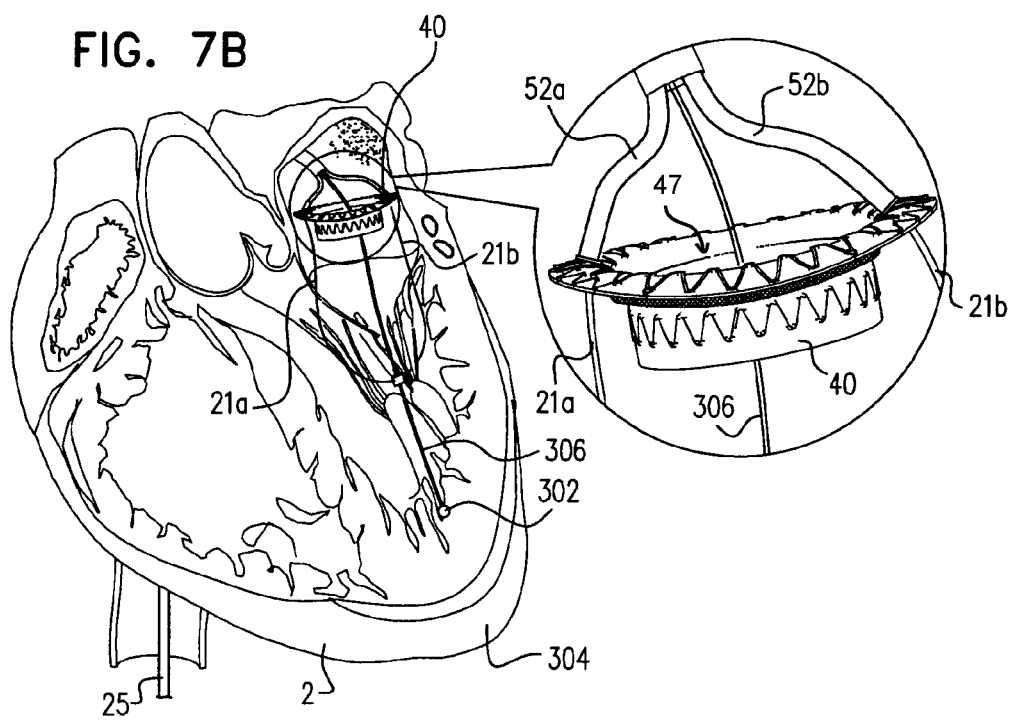

FIG. 10
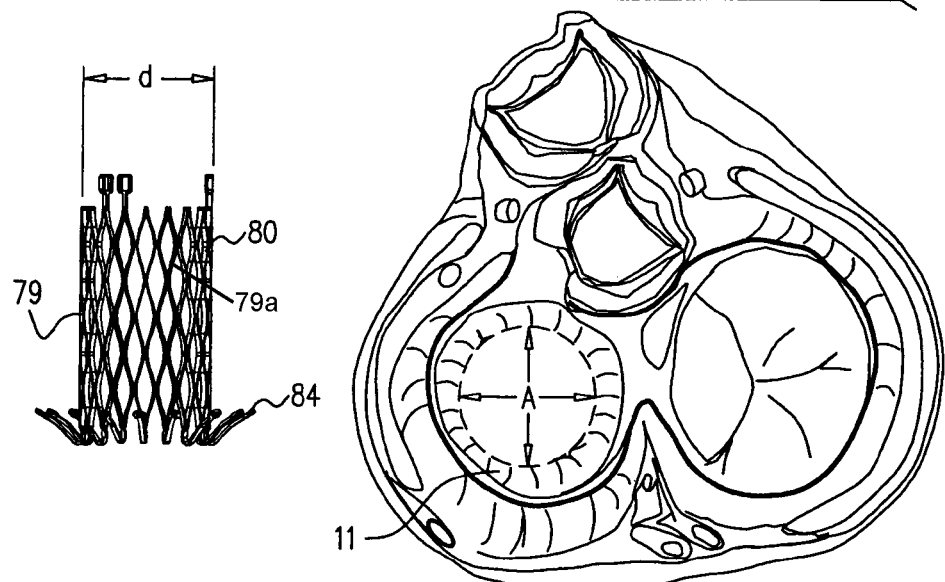
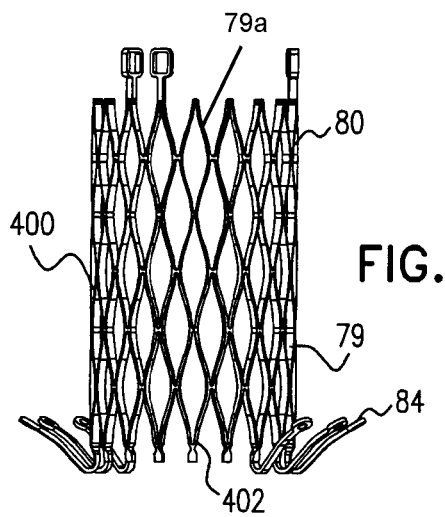
FIG. 11A
FIG. 11B
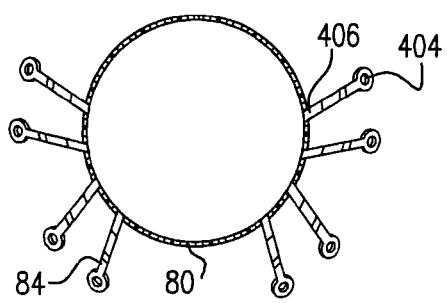
FIG. 11C
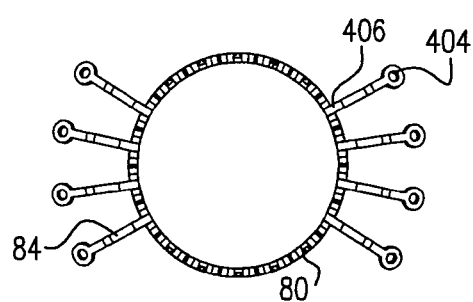

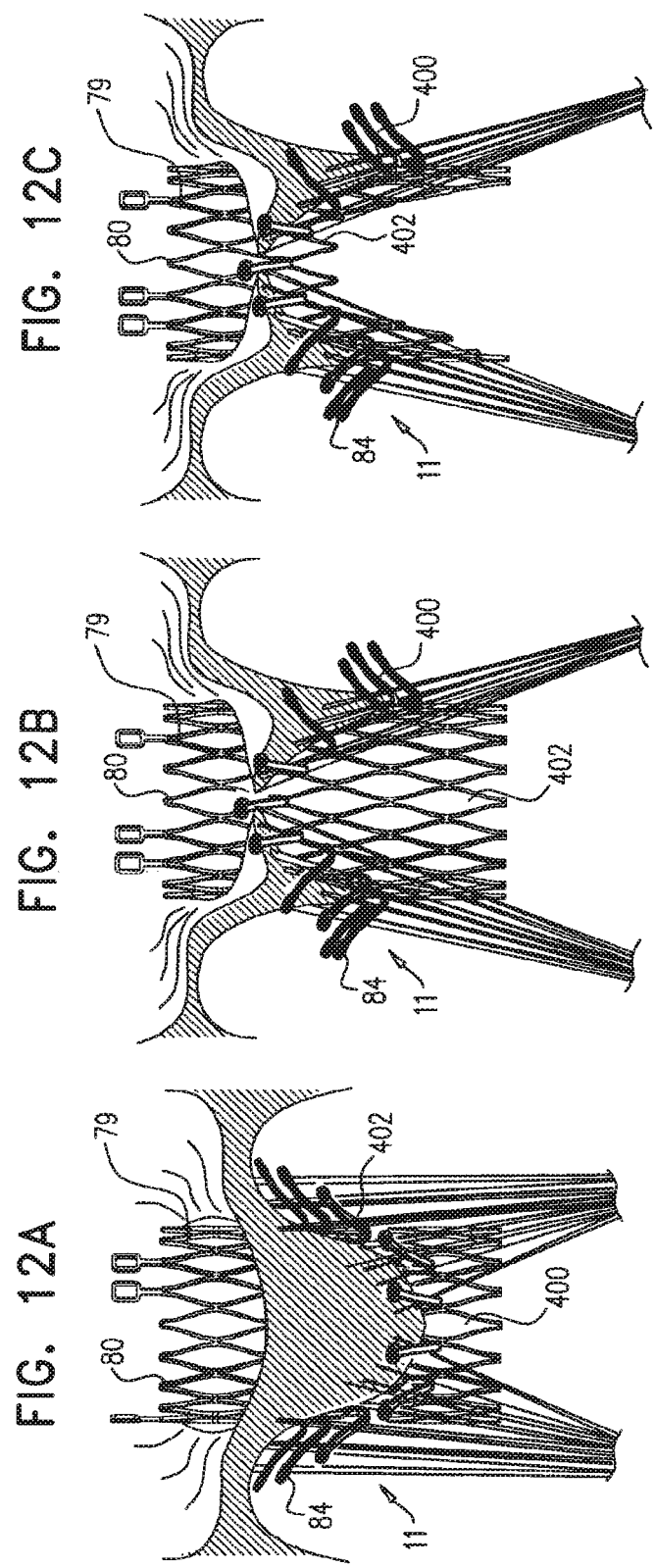

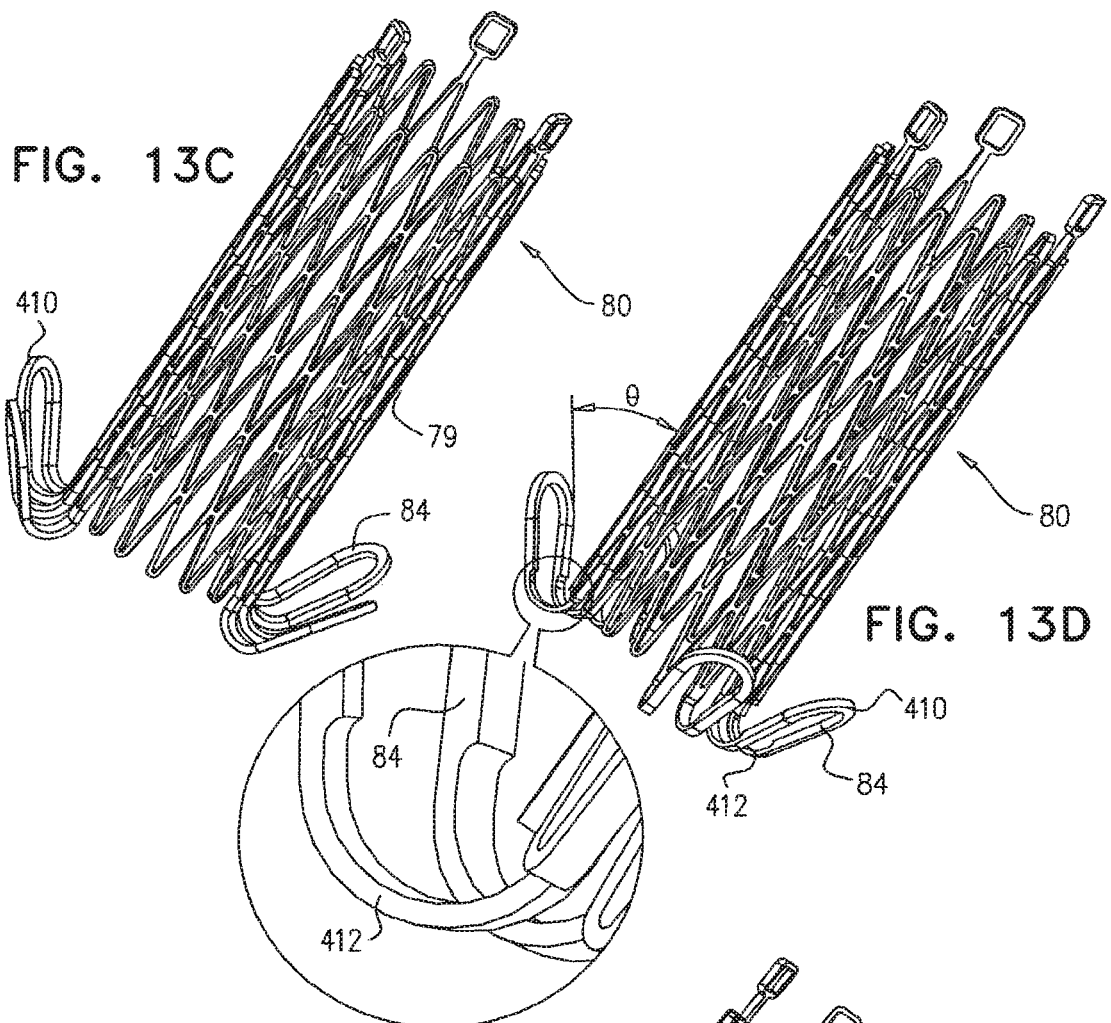
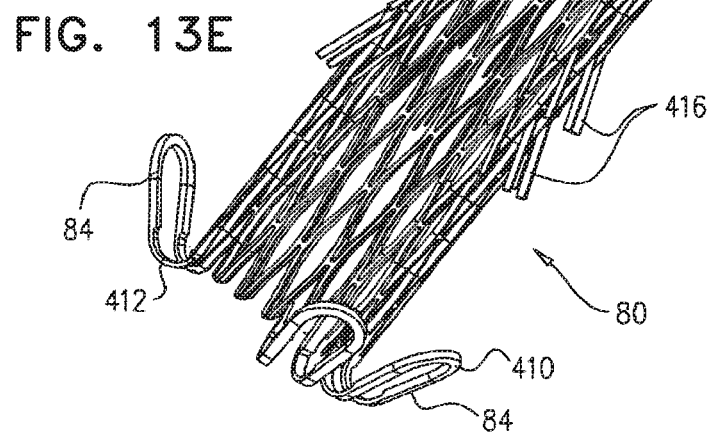

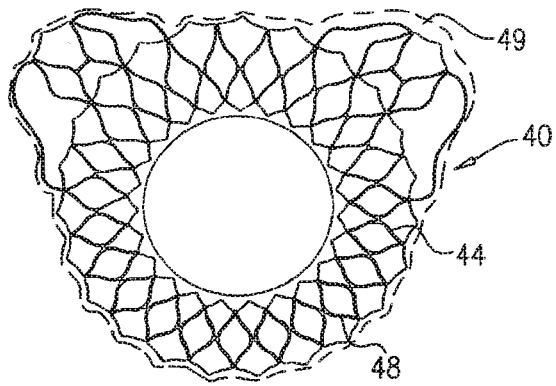
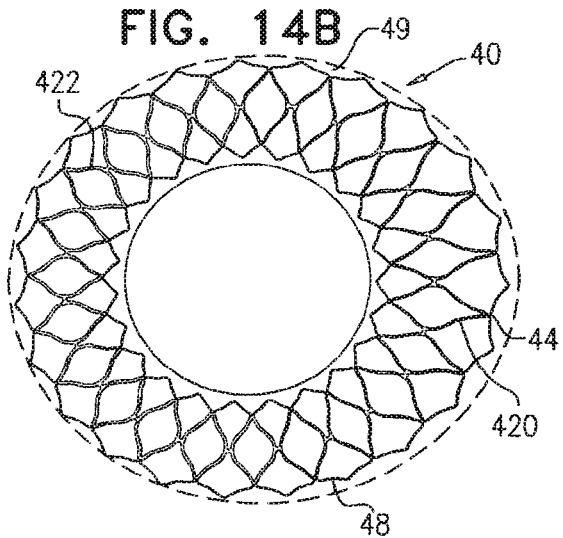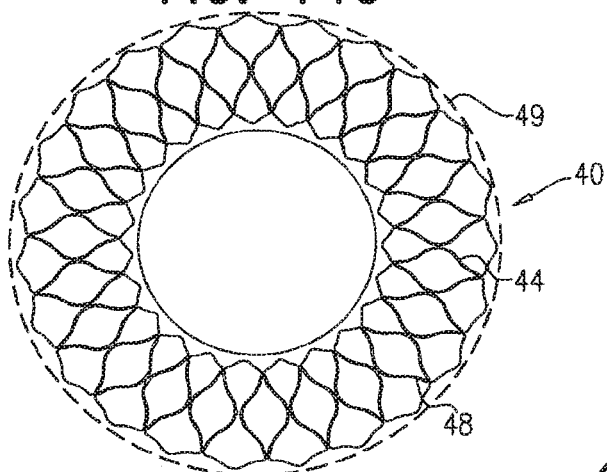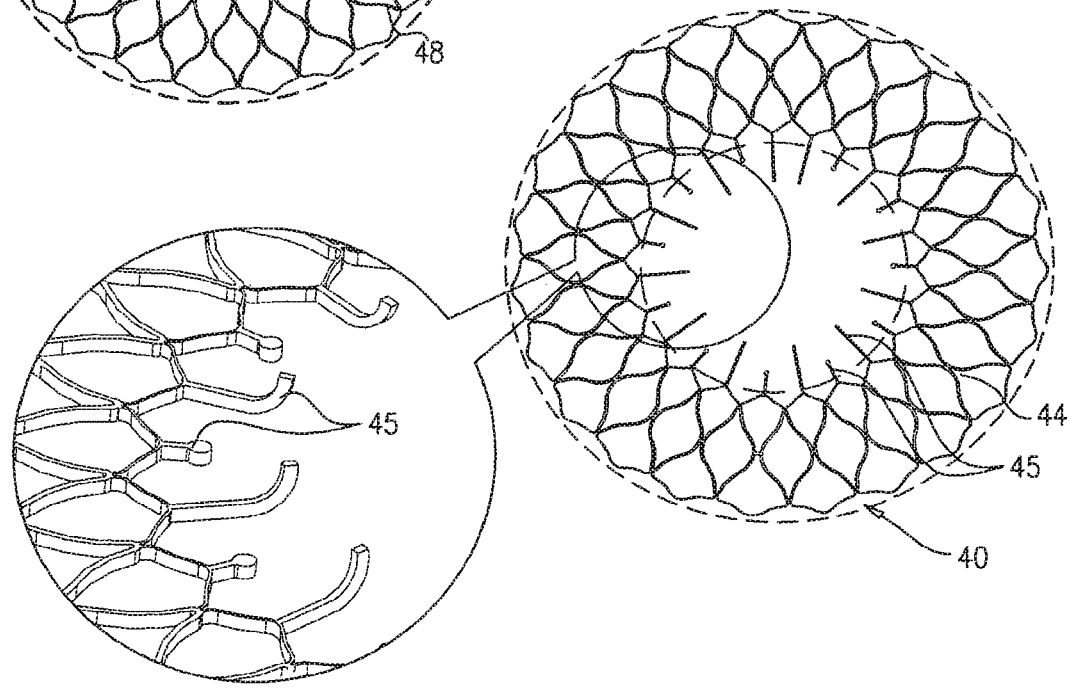

SECTION A-A

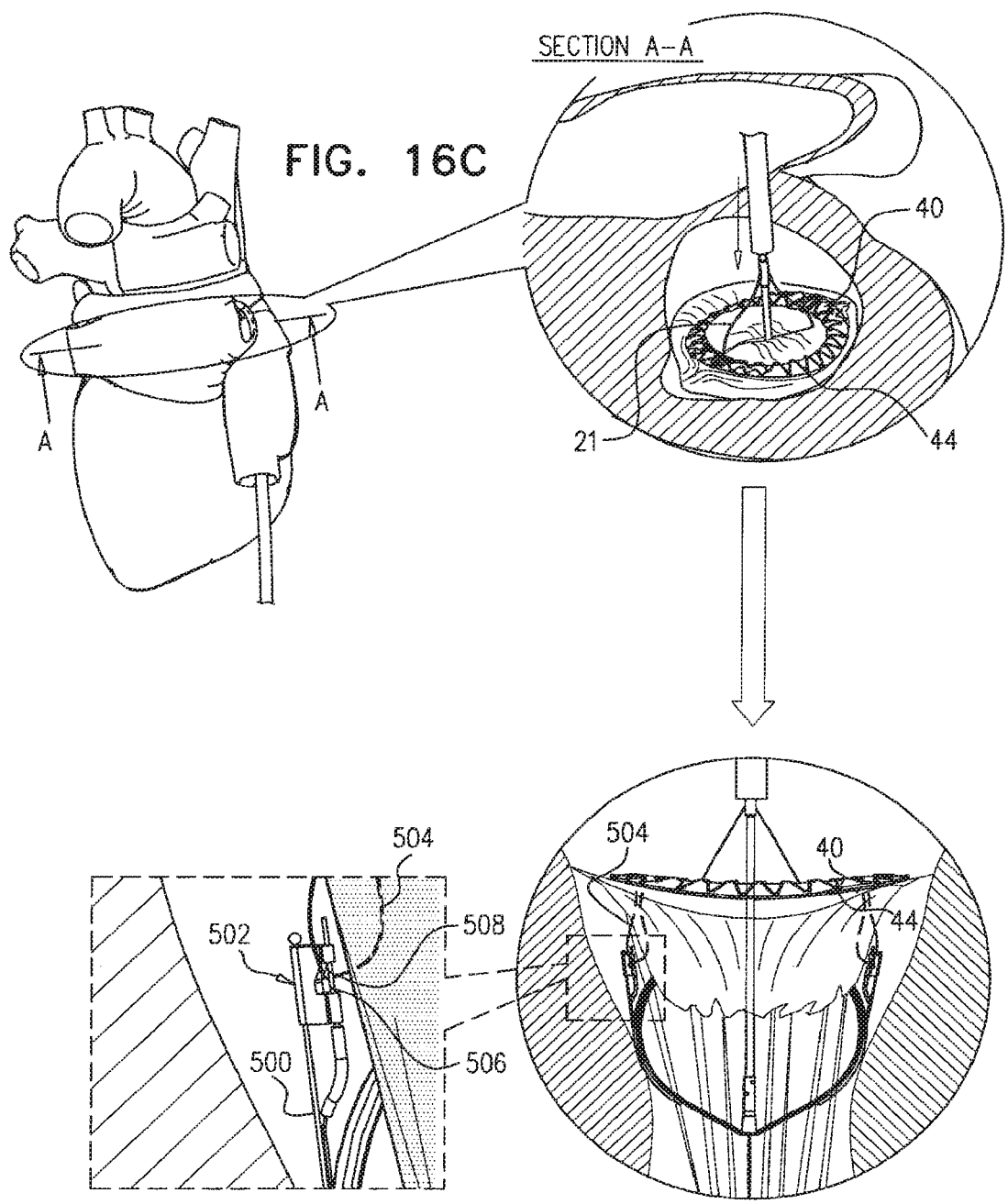

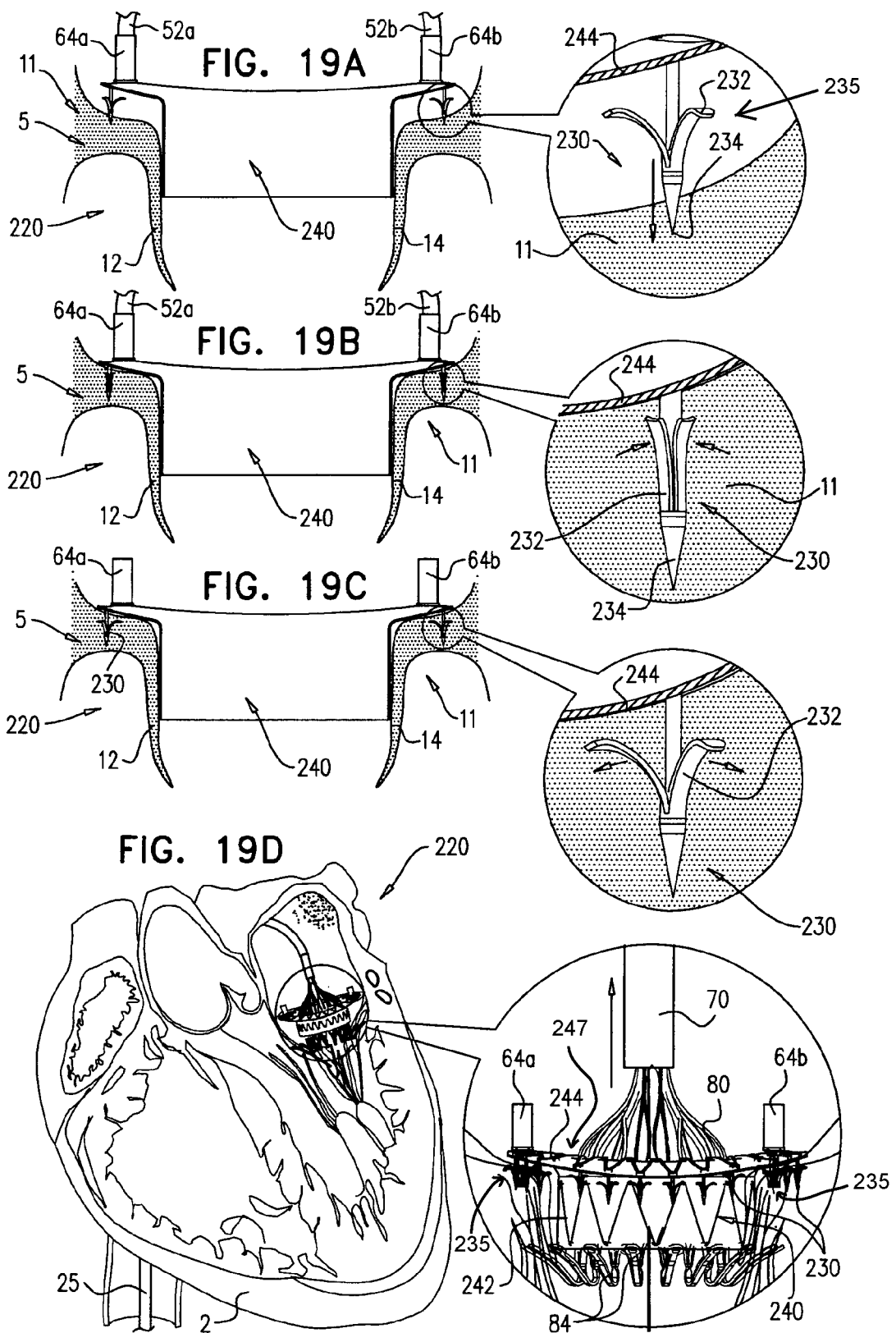

VALVE PROSTHESIS CONFIGURED FOR DEPLOYMENT IN ANNULAR SPACER

CROSS-REFERENCES TO RELATED APPLICATIONS

The present application is a continuation of U.S. patent application Ser. No. 15/691,032, filed Aug. 30, 2017, now pending, which is a continuation of U.S. patent application Ser. No. 14/689,608, filed Apr. 17, 2015, which issued as U.S. Pat. No. 9,763,657 on Sep. 19, 2017, which is a continuation of U.S. patent application Ser. No. 13/811,308, filed Mar. 7, 2013, which issued as U.S. Pat. No. 9,017,399 on Apr. 28, 2015, which is a U.S. national stage entry under 35 U.S.C. § 371 of International Application No. PCT/IL2011/000582, filed Jul. 21, 2011, which claims priority and is a continuation-in-part of:

(a) U.S. patent application Ser. No. 12/840,463, filed Jul. 21, 2010;

(b) U.S. patent application Ser. No. 13/033,852, filed Feb. 24, 2011, which is a continuation-in-part of U.S. patent application Ser. No. 12/840,463, filed Jul. 21, 2010; and claims priority from U.S. Provisional Patent Application No. 61/492,449, filed Jun. 2, 2011.

All of the above-referenced applications are incorporated herein by reference.

FIELD OF THE INVENTION

Embodiments of the present disclosure relate in general to valve replacement. More specifically, embodiments of the present disclosure relate to prosthetic valves for replacement of an atrioventricular valve.

BACKGROUND

Dilation of the annulus of the mitral valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium. Dilation of the annulus is sometimes treated by implanting a prosthetic mitral valve at a patient's native mitral valve.

SUMMARY

For some embodiments of the present disclosure, one or more guide members (e.g., wires, sutures, or strings) is configured to be anchored to respective commissures of a native atrioventricular valve of a patient, and each guide member facilitates the advancement therealong of respective commissural anchors. The commissural anchors are shaped so as to define a plurality of barbs or prongs which are expandable to restrict proximal movement of the anchors following their deployment. The guide members facilitate advancement of a collapsible prosthetic valve support (e.g., a skirt) which serves as a base for and receives a collapsible prosthetic mitral valve which is subsequently coupled to the support. The support includes a proximal annular element, or ring, and a distal cylindrical element. The cylindrical element is configured to push aside and press against the native leaflets of the native valve, and the proximal annular element is shaped so as to define one or more holes for sliding the valve support along the one or more guide members. The proximal annular element is configured to be positioned along the annulus of the native valve.

The collapsible prosthetic valve is configured for implantation in and/or at least partial replacement (e.g., full replacement) of the native atrioventricular valve of the patient, such as a native mitral valve or a native tricuspid valve. The valve support and the prosthetic valve are configured to assume collapsed states for minimally-invasive delivery to the diseased native valve, such as by percutaneous or transluminal delivery using one or more catheters. For some embodiments, the valve support and the prosthetic valve are implanted during an open-heart procedure.

The prosthetic valve support is shaped so as to define a downstream skirt. The downstream skirt is configured to be placed at native valve, such that the downstream skirt passes through the orifice of the native valve and extends toward, and, in some embodiments partially into, a ventricle. The downstream skirt in some embodiments additionally pushes aside and presses against the native leaflets of the native valve, which are left in place during and after implantation of the prosthetic valve support and/or the prosthetic valve.

The proximal annular element has upper and lower surfaces. For some embodiments of the present disclosure, one or more, e.g., a plurality of, tissue anchors are coupled to the lower surface and facilitate anchoring of the proximal annular element to the annulus of the native valve. For some embodiments, the one or more anchors include at least first and second commissural anchors that are configured to be implanted at or in the vicinity of the commissures of the native valve.

The cylindrical element of the valve support has first and second ends and a cylindrical body disposed between the first and second ends. The first end of the cylindrical element is coupled to the annular element while the second end defines a free end of the cylindrical element. For some embodiments of the present disclosure, the cylindrical element of the valve support is invertible such that (1) during a first period, the second end and the cylindrical body of the cylindrical element are disposed above the annular element (e.g., in the atrium of the heart), and (2) during a second period, the second end and the cylindrical body of the cylindrical element are disposed below the annular element (e.g., in the ventricle of the heart).

For some embodiments, techniques are applied to facilitate sealing of the interface between the valve support and the native valve, and/or the interface between the prosthetic valve and the native valve. For example, a sealing balloon may be placed on a valve-facing, lower side of the annular element of the valve support, the sealing balloon being configured to be inflated such that the balloon seals the interface between the valve support and the native valve. Alternatively or additionally, commissural helices are wrapped around chordae tendineae of the patient in order to facilitate sealing of the valve commissures around the valve support and/or around the valve. Further alternatively or additionally, the valve commissures are grasped by grasping elements that act in order to facilitate sealing of the commissures around the valve support and/or around the valve. For some embodiments, one or more of the aforementioned sealing elements facilitates anchoring of the prosthetic valve to the native valve in addition to facilitating sealing.

For some embodiments, the prosthetic valve includes an expandable frame (e.g., a wire frame), and a sealing material (such as latex) is disposed on the outer surface of the frame so as to form webbing between at least some of the struts of the wire frame, and to provide sealing between the wire frame and the native valve.

For some embodiments, an invertible prosthetic valve support is used to support a prosthetic valve. In some embodiments, a sealing element is disposed circumferentially around a surface of the invertible prosthetic valve support that is initially an inner surface of the invertible prosthetic valve support. The invertible prosthetic valve support is anchored to the native valve, and is subsequently inverted. Subsequent to the inversion of the invertible prosthetic valve support, the sealing element is disposed on the outer surface of the invertible prosthetic valve support and acts to seal the interface between the outer surface and the native valve.

In accordance with some embodiments of the present disclosure, an apparatus may include a prosthetic valve support configured to be placed at an annulus of a native atrioventricular valve of a patient, the prosthetic valve support defining an annular element that defines an inner cross-sectional area thereof; an expandable prosthetic valve configured to be placed into a ventricle of the patient, the prosthetic valve including: an expandable frame; and prosthetic valve leaflets coupled to the expandable frame; the expandable frame of the prosthetic valve being configured such that when the frame is in a non-constrained state thereof, a cross-sectional area of the frame, along at least a given portion of a length of the frame, is greater than the cross-sectional area defined by the annular element of the prosthetic valve support, the prosthetic valve thereby being couplable to the prosthetic valve support at any location along the portion, responsively to radial forces acted upon the valve support by the expandable frame, by the expandable frame being expanded when the location along the portion is aligned with the annular element of the prosthetic valve support.

For some embodiments, the valve support is collapsible for transcatheter delivery.

For some embodiments, the native atrioventricular valve includes a mitral valve, and the prosthetic valve includes three prosthetic leaflets.

For some embodiments, the annular element of the valve support is asymmetrically shaped.

For some embodiments, the annular element is shaped to define a hole, and a center of the hole is disposed asymmetrically with respect to an outer perimeter of the annular element.

For some embodiments, the frame includes proximally-facing protrusions at a distal end thereof, the protrusions being configured to prevent proximal migration of the valve into an atrium.

For some embodiments, the protrusions are disposed at an angle from the frame of more than 40 degrees.

For some embodiments, the protrusions are disposed at an angle from the frame of less than 80 degrees.

For some embodiments, a length of each of the protrusions is less than 5 mm.

For some embodiments, the frame includes a single proximally-facing protrusion corresponding to each native valve leaflet of the valve, each of the protrusions having a width of less than 1 mm.

For some embodiments, the protrusions are disposed in a sinusoidal configuration such that the protrusions conform with a saddle shape of the patient's native annulus.

For some embodiments, the protrusions are configured to prevent the native leaflets from interfering with a left ventricular outflow tract of the patient.

For some embodiments, the frame includes first and second sets of one or more protrusions, each set of protrusions configured to ensnare a respective native leaflet of the native valve of the patient, the first set of protrusions being disposed within a first circumferential arc with respect to a longitudinal axis of the prosthetic valve, on a first side of a distal end of the frame, the second set of protrusions being disposed within a second circumferential arc with respect to the longitudinal axis of the prosthetic valve, on a second side of the distal end of the frame, the first and second sets being disposed so as to provide first and second gaps therebetween at the distal end of the frame, at least one of the gaps having a circumferential arc of at least 20 degrees, the apparatus further including one or more valve guide members configured to be delivered to one or more commissures of the native valve, and to guide the valve such that the first and second circumferential arcs are aligned with respective leaflets of the native valve and such that the first and second gaps are aligned with respective commissures of the native valve.

For some embodiments, the at least one of the gaps has a circumferential arc of at least 60 degrees.

For some embodiments, the first circumferential arc defines an angle of between 25 degrees and 90 degrees about the longitudinal axis of the prosthetic valve.

For some embodiments, the second circumferential arc defines an angle of between 25 degrees and 90 degrees about the longitudinal axis of the prosthetic valve.

For some embodiments, the first circumferential arc defines an angle of between 45 degrees and 75 degrees about the longitudinal axis of the prosthetic valve.

For some embodiments, the second circumferential arc defines an angle of between 45 degrees and 75 degrees about the longitudinal axis of the prosthetic valve.

For some embodiments, the expandable frame of the prosthetic valve is configured such that when the frame is in a non-constrained state thereof the frame has a maximum diameter of less than 25 mm.

For some embodiments, the expandable frame of the prosthetic valve is configured such that when the frame is in a non-constrained state thereof the frame has a maximum diameter of more than 15 mm.

For some embodiments, the expandable frame of the prosthetic valve is configured such that when the frame is in a non-constrained state thereof the frame has a maximum diameter of less than 20 mm.

For some embodiments, the expandable frame of the prosthetic valve is configured such that when the frame is in a non-constrained state thereof, a cross-sectional area of the frame at a proximal end of the frame is greater than a cross-sectional area of the frame at a distal end of the frame.

For some embodiments, the expandable frame of the prosthetic valve is configured such that when the frame is in the non-constrained state thereof the frame defines a frustoconical shape.

For some embodiments, the expandable frame of the prosthetic valve is configured such that when the frame is in the non-constrained state thereof the frame defines a trumpet shape.

In accordance with some embodiments of the present disclosure, a method may include placing a prosthetic valve support at an annulus of a native atrioventricular valve of a patient, the prosthetic valve support defining an annular element that defines an inner cross-sectional area thereof; placing into a ventricle of the patient, an expandable prosthetic valve, the prosthetic valve including an expandable frame, and prosthetic valve leaflets coupled to the expandable frame, the expandable frame of the prosthetic valve being configured such that when the frame is in a non-constrained state thereof, a cross-sectional area of the frame, along at least a given portion of a length of the frame, is greater than the cross-sectional area defined by the annular element of the prosthetic valve support; determining a location anywhere along the portion at which to couple the expandable valve the prosthetic valve support; and in response thereto, aligning the location along the portion of the expandable frame with the annular element of the prosthetic valve support; and coupling the expandable valve to the prosthetic valve support at the location, responsively to radial forces acted upon the valve support by the expandable frame, by facilitating expansion of the expandable frame, when the location along the portion is aligned with the annular element of the prosthetic valve support.

For some embodiments, placing the valve support at the annulus includes transcatheterally placing the valve support at the annulus in a collapsed state.

For some embodiments, the native atrioventricular valve includes a mitral valve, and placing the prosthetic valve into the ventricle includes placing into the ventricle a prosthetic valve that includes three prosthetic leaflets.

For some embodiments, placing the prosthetic valve support at the annulus includes placing an asymmetrically-shaped prosthetic valve support at the annulus.

For some embodiments, placing the prosthetic valve support at the annulus includes placing at the annulus an annular element that is shaped to define a hole, a center of the hole being disposed asymmetrically with respect to an outer perimeter of the annular element, the annular element being placed such that a center of the hole is disposed asymmetrically with respect to the annulus.

For some embodiments, the frame includes proximally-facing protrusions at a distal end thereof, the protrusions being configured to prevent proximal migration of the valve into an atrium, and coupling the expandable valve to the prosthetic valve support includes preventing proximal migration of the valve by coupling the valve to the valve support such that the leaflets are disposed at least partially between the protrusions and the valve support.

For some embodiments, coupling the expandable valve to the prosthetic valve support includes preventing the native leaflets from interfering with a left ventricular outflow tract of the patient.

For some embodiments, coupling the expandable valve to the prosthetic valve support includes allowing movement of the leaflets with respect to the frame while preventing the proximal migration of the valve.

For some embodiments, the frame includes first and second sets of one or more protrusions, each set of protrusions configured to ensnare a respective native leaflet of the native valve of the patient, the first set of protrusions being disposed within a first circumferential arc with respect to a longitudinal axis of the prosthetic valve, on a first side of a distal end of the frame, the second set of protrusions being disposed within a second circumferential arc with respect to the longitudinal axis of the prosthetic valve, on a second side of the distal end of the frame, the first and second sets being disposed so as to provide first and second gaps therebetween at the distal end of the frame, at least one of the gaps having a circumferential arc of at least 20 degrees, the method further including guiding the valve such that the first and second circumferential arcs are aligned with respective leaflets of the native valve and such that the first and second gaps are aligned with respective commissures of the native valve.

For some embodiments, facilitating expansion of the frame includes facilitating expansion of the frame to a maximum diameter of less than 25 mm.

For some embodiments, facilitating expansion of the frame includes facilitating expansion of the frame to a maximum diameter of more than 15 mm.

For some embodiments, facilitating expansion of the frame includes facilitating expansion of the frame to a maximum diameter of less than 20 mm.

For some embodiments, facilitating expansion of the frame includes facilitating expansion of the frame such that a cross-sectional area of the frame at a proximal end of the frame is greater than a cross-sectional area of the frame at a distal end of the frame.

For some embodiments, facilitating expansion of the frame includes facilitating expansion of the frame such that the frame defines a frustoconical shape.

For some embodiments, facilitating expansion of the frame includes facilitating expansion of the frame such that the frame defines a trumpet shape.

In accordance with some embodiments of the present disclosure, a method may include determining an indication of an area defined by an annulus of a native atrioventricular valve of a patient; selecting a prosthetic valve support by determining that the prosthetic valve support defines an annular element that defines an inner cross-sectional area that is less than the area defined by the annulus; placing the prosthetic valve support at the annulus of the native atrioventricular valve; placing into a ventricle of the patient, an expandable prosthetic valve, the prosthetic valve including an expandable frame, and prosthetic valve leaflets coupled to the expandable frame; coupling the expandable valve to the prosthetic valve support at the location, responsively to radial forces acted upon the valve support by the expandable frame, by facilitating expansion of the expandable frame, a cross-sectional area defined by the expandable frame of the prosthetic valve being limited by the cross-sectional area defined by the annular element of the prosthetic valve support, such as to facilitate sealing of the native valve with respect to the prosthetic valve by facilitating closing of leaflets of the native valve around the prosthetic valve, upon deployment of the prosthetic valve.

For some embodiments, facilitating closing of leaflets of the native valve around the prosthetic valve includes facilitating sealing of the native valve at commissures of the native valve.

For some embodiments, facilitating closing of leaflets of the native valve around the prosthetic valve includes facilitating closing of the leaflets of the native valve around an outer surface of the expandable frame.

For some embodiments, placing the valve support at the annulus includes transcatheterally placing the valve support at the annulus in a collapsed state.

For some embodiments, the native atrioventricular valve includes a mitral valve, and placing the prosthetic valve into the ventricle includes placing into the ventricle a prosthetic valve that includes three prosthetic leaflets.

For some embodiments, placing the prosthetic valve support at the annulus includes placing an asymmetrically-shaped prosthetic valve support at the annulus.

For some embodiments, placing the prosthetic valve support at the annulus includes placing at the annulus an annular element that is shaped to define a hole, a center of the hole being disposed asymmetrically with respect to an outer perimeter of the annular element, the annular element being placed such that a center of the hole is disposed asymmetrically with respect to the annulus.

For some embodiments, the frame includes proximally-facing protrusions at a distal end thereof, the protrusions being configured to prevent proximal migration of the valve into an atrium, and coupling the expandable valve to the prosthetic valve support includes preventing proximal migration of the valve by coupling the valve to the valve support such that the leaflets are disposed at least partially between the protrusions and the valve support.

For some embodiments, coupling the expandable valve to the prosthetic valve support includes preventing the native leaflets from interfering with a left ventricular outflow tract of the patient.

For some embodiments, coupling the expandable valve to the prosthetic valve support includes allowing movement of the leaflets with respect to the frame while preventing proximal migration of the valve.

For some embodiments, the frame includes first and second sets of one or more protrusions, each set of protrusions configured to ensnare a respective native leaflet of the native valve of the patient, the first set of protrusions being disposed within a first circumferential arc with respect to a longitudinal axis of the prosthetic valve, on a first side of a distal end of the frame, the second set of protrusions being disposed within a second circumferential arc with respect to the longitudinal axis of the prosthetic valve, on a second side of the distal end of the frame, the first and second sets being disposed so as to provide first and second gaps therebetween at the distal end of the frame, at least one of the gaps having a circumferential arc of at least 20 degrees, the method further including guiding the valve such that the first and second circumferential arcs are aligned with respective leaflets of the native valve and such that the first and second gaps are aligned with respective commissures of the native valve.

For some embodiments, facilitating expansion of the frame includes facilitating expansion of the frame to a maximum diameter of less than 25 mm.

For some embodiments, facilitating expansion of the frame includes facilitating expansion of the frame to a maximum diameter of more than 15 mm.

For some embodiments, facilitating expansion of the frame includes facilitating expansion of the frame to a maximum diameter of less than 20 mm.

For some embodiments, facilitating expansion of the frame includes facilitating expansion of the frame such that a cross-sectional area of the frame at a proximal end of the frame is greater than a cross-sectional area of the frame at a distal end of the frame.

For some embodiments, facilitating expansion of the frame includes facilitating expansion of the frame such that the frame defines a frustoconical shape.

For some embodiments, facilitating expansion of the frame includes facilitating expansion of the frame such that the frame defines a trumpet shape.

In accordance with some embodiments of the present disclosure, a method may include placing a prosthetic valve support at an annulus of a native atrioventricular valve of a patient; placing a prosthetic valve into a ventricle of the patient, the prosthetic valve including protrusions at a distal end thereof; ensnaring one or more native leaflets of the native valve of the patient with the protrusions; and coupling the prosthetic valve to the native valve, by sandwiching native leaflets of the native valve between the protrusions and the valve support, by pulling the prosthetic valve proximally with respect to the valve support, and while the native leaflets are sandwiched between the protrusions and the valve support, coupling the prosthetic valve to the valve support, by facilitating radial expansion of the prosthetic valve such that the prosthetic valve is held in place with respect to the valve support responsively to radial forces acted upon the valve support by the prosthetic valve.

In accordance with some embodiments of the present disclosure, a method may include determining an indication of an area defined by an annulus of a native atrioventricular valve of a patient: selecting a prosthetic valve to be placed in the native valve by determining that the valve defines a cross-sectional area that is less than 90% of the area defined by the annulus: and deploying the prosthetic valve at the native valve, the selecting of the prosthetic valve facilitating sealing of the native valve with respect to the prosthetic valve by facilitating closing of leaflets of the native valve around the prosthetic valve, upon deployment of the prosthetic valve.

For some embodiments, selecting the prosthetic valve includes selecting a prosthetic valve having a material disposed on an outer surface thereof.

For some embodiments, selecting the prosthetic valve includes selecting a prosthetic valve having a material that prevents tissue growth disposed on an outer surface thereof.

For some embodiments, selecting the prosthetic valve includes selecting a prosthetic valve having a material that promotes tissue growth disposed on an outer surface thereof.

For some embodiments, selecting the prosthetic valve to be placed in the native valve includes determining that the valve defines a cross-sectional area that is less than 80% of the area defined by the annulus.

For some embodiments, selecting the prosthetic valve to be placed in the native valve includes determining that the valve defines a cross-sectional area that is less than 60% of the area defined by the annulus.

In accordance with some embodiments of the present disclosure, an apparatus may include one or more valve support guide members configured to be delivered to one or more commissures of a native atrioventricular valve of a patient; one or more valve support anchors configured to be anchored to the one or more commissures of the native valve; a prosthetic valve support advanceable toward the native valve along the one or more valve support guide members and anchored to the native valve at at least the one or more commissures; and a prosthetic valve configured to be coupled to the valve support.

For some embodiments, the valve support is collapsible for transcatheter delivery and expandable to contact the native atrioventricular valve.

For some embodiments, the one or more valve support anchors are configured to be anchored to the one or more commissures from ventricular surfaces thereof.

For some embodiments, the one or more valve support guide members includes one valve support guide member that is looped through first and second commissures of the atrioventricular valve in a manner in which a looped portion of the valve support guide member is disposed in a ventricle of the patient and first and second free ends of the valve support guide member are accessible from a site outside a body of the patient.

For some embodiments, the one or more valve support anchors includes first and second tissue anchors, the first and second tissue anchors being configured to be anchored to respective first and second commissures of the atrioventricular valve of the patient.

For some embodiments, the one or more valve support anchors each include one or more radially-expandable prongs, and the one or more prongs are disposed within a sheath in a compressed state prior to the anchoring, and exposed from within the sheath in order to expand and facilitate anchoring of the valve support anchor to the respective commissures.

For some embodiments, the prosthetic valve includes two or more prosthetic leaflets.

For some embodiments, the native atrioventricular valve includes a mitral valve, and the prosthetic valve includes three prosthetic leaflets.

For some embodiments, the valve support guide members are removable from the patient following the anchoring of the prosthetic valve support at the atrioventricular valve.

For some embodiments, the valve support is shaped so as to define a distal portion which is configured to push aside, at least in part, native leaflets of the valve of the patient.

For some embodiments, the one or more valve support anchors are advanceable along the one or more valve support guide members.

For some embodiments, the valve support is shaped so as to define one or more holes, the one or more holes being configured to facilitate slidable passage therethrough of a respective one of the one or more valve support guide members.

For some embodiments, the prosthetic valve is shaped so as to define one or more snares configured to ensnare one or more native leaflets of the native valve of the patient.

For some embodiments, the one or more valve support anchors includes one or more ventricular anchors, and the apparatus further includes one or more atrial anchors, each atrial anchor being configured to be advanced toward an atrial surface of the valve support and anchor in place the valve support in a vicinity of a respective one of the ventricular anchors.

For some embodiments, the apparatus includes one or more delivery lumens, and: each one of the one or more valve support anchors is removably coupled to a distal end of a respective delivery lumen, the delivery lumen is configured to facilitate advancement of the one or more anchors along the one or more guide members, and the delivery lumen is decoupled from the anchor following the anchoring of the anchor to the one or more commissures.

For some embodiments, the one or more valve support guide members are removable from the body of the patient following the advancement of the one or more anchors along the one or more guide members.

For some embodiments, the valve support is shaped so as to define one or more holes, the one or more holes are configured to facilitate slidable passage therethrough of a respective one of the one or more delivery lumens, and the one or more delivery lumens are decoupleable from the respective valve support anchor following the anchoring of the valve support to at least the one or more commissures.

For some embodiments, the one or more delivery lumens are removable from the body of the patient following the anchoring of the valve support to at least the one or more commissures.

For some embodiments, the valve support includes an annular element and a generally cylindrical element coupled to the annular element, the generally cylindrical element being configured to push aside native leaflets of the native valve, the cylindrical element has first and second ends and a cylindrical body that is disposed between the first and second ends.

For some embodiments, the apparatus includes one or more annular element tissue anchors, the annular element has an upper surface and a lower surface, and the lower surface is coupled to the one or more annular element tissue anchors, the one or more annular element tissue anchors being configured to puncture tissue of a native annulus of the native valve of the patient.

For some embodiments, one or more annular element tissue anchors includes a plurality of annular element tissue anchors positioned around the lower surface of the annular element.

For some embodiments, the one or more annular element tissue anchors includes a first commissural anchor configured to puncture tissue of the native valve at a first commissure thereof, and a second commissural anchor configured to puncture tissue of the native valve at a second commissure thereof.

For some embodiments, each anchor of the one or more annular element tissue anchors includes a distal pointed tip and one or more radially-expandable prongs, the prongs being configured to expand and facilitate anchoring of the anchor and restrict proximal motion of the annular element tissue anchor.

For some embodiments, the apparatus includes one or more prosthetic valve guide members reversibly couplable to the cylindrical element in a vicinity of the second end of the cylindrical element, the prosthetic valve guide members being configured to facilitate advancement of the prosthetic valve therealong and toward the valve support.

For some embodiments, the first end of the cylindrical element is coupled to the annular element, during a first period, the second end of the cylindrical element is disposed above the annular element in a manner in which the body of the cylindrical element is disposed above the annular element, and the cylindrical element is invertible in a manner in which, during a second period, the second end of the cylindrical element is disposed below the annular element and the body of the cylindrical element is disposed below the annular element.

For some embodiments, during the first period, the second end of the cylindrical element is disposed in an atrium of a heart of the patient and the annular element is positioned along an annulus of the native valve, the prosthetic valve is advanceable along the one or more prosthetic valve guide members into a ventricle of the heart of the patient, and in response to advancement of the prosthetic valve into the ventricle, the one or more prosthetic valve guide members are pulled into the ventricle and pull the second end and the body of the cylindrical element into the ventricle to invert the cylindrical element.

In accordance with some embodiments of the present disclosure, a method may include advancing one or more valve support guide members toward one or more commissures of a native atrioventricular valve of a patient; advancing along the one or more valve support guide members one or more valve support tissue anchors toward the one or more commissures; anchoring the one or more valve support tissue anchors to the one or more commissures; anchoring a prosthetic valve support at the native atrioventricular valve by anchoring the prosthetic valve support at at least the one or more commissures; and coupling a prosthetic valve to the prosthetic valve support.

For some embodiments, the method includes removing the one or more valve support guide members following the anchoring of the prosthetic valve support at the native atrioventricular valve.

For some embodiments, advancing the one or more valve support guide members toward the one or more commissures includes advancing one guide member and looping the one guide member through first and second commissures of the native atrioventricular valve in a manner in which a looped portion of the guide member is disposed in a ventricle of the patient and first and second free ends of the guide member are accessible from a site outside a body of the patient.

For some embodiments, anchoring the one or more valve support anchors includes anchoring the one or more valve support anchors to ventricular surface of the respective commissures of the native valve.

For some embodiments, anchoring the one or more valve support anchors includes anchoring first and second tissue anchors to respective first and second commissures of the native valve.

For some embodiments, advancing along the one or more valve support guide members the one or more valve support tissue anchors includes advancing the one or more valve support tissue anchors within a sheath, and anchoring the one or more valve support tissue anchors includes exposing the one or more valve support anchors from within the sheath and facilitating radial expansion of one or more radially-expandable prongs of the one or more anchors.

For some embodiments, coupling the prosthetic valve to the prosthetic valve support includes coupling a prosthetic valve having two or more leaflets.

For some embodiments, the native atrioventricular valve includes a mitral valve of the patient, and coupling the prosthetic valve to the prosthetic valve support includes coupling a prosthetic valve having three leaflets.

For some embodiments, anchoring the prosthetic valve support includes pushing aside, at least in part, native leaflets of the valve of the patient by at least a portion of the support.

For some embodiments, the prosthetic valve support is coupled to one or more annulus tissue anchors, and anchoring the prosthetic valve support includes pushing the one or more annulus tissue anchors into tissue of an annulus of the native valve.

For some embodiments, coupling the prosthetic valve to the prosthetic valve support includes ensnaring one or more native leaflets of the native valve of the patient by a portion of the prosthetic valve.

For some embodiments, the one or more valve support anchors includes one or more ventricular anchors, and the method further includes advancing one or more atrial anchors to an atrial surface of the valve support, and anchoring in place the valve support in a vicinity of a respective one of the ventricular anchors.

For some embodiments, the method includes advancing the valve support along the one or more valve support guide members prior to the anchoring of the valve support.

For some embodiments, the valve support is shaped so as to define one or more holes, and advancing the valve support along the one or more valve support guide members includes threading the one or more valve support guide members through the one or more holes of the valve support and sliding the valve support along the one or more guide members.

For some embodiments, the method includes removing the one or more valve support guide members from a body of the patient following the anchoring of the valve support.

For some embodiments, the valve support includes: an annular element, and a generally cylindrical element having first and second ends and a cylindrical body that is disposed between the first and second ends, the first end being coupled to the annular element; and anchoring of the valve support, including anchoring the valve support in a manner in which: the annular element is positioned along an annulus of the native valve, the second end of the cylindrical element is disposed above the annular element in an atrium of a heart of the patient, and the body of the cylindrical element is disposed above the annular element.

For some embodiments, the method includes, following the anchoring, inverting the cylindrical element to pull the second end of the cylindrical element below the annular element and into a ventricle of the heart, in a manner in which the body of the cylindrical element is disposed below the annular element and pushes aside one or more native leaflets of the valve of the patient.

For some embodiments, inverting the cylindrical element includes advancing the prosthetic valve along one or more prosthetic valve guide members reversibly coupled to the cylindrical element in a vicinity of the second end thereof, advancing the prosthetic valve includes advancing the prosthetic valve into the ventricle to pull the prosthetic valve guide members and the second end of the cylindrical element into the ventricle, and the method further includes following the advancing of the prosthetic valve into the ventricle, pulling proximally the prosthetic valve such that a proximal portion of the valve contacts the valve support.

For some embodiments, pulling the prosthetic valve proximally includes ensnaring the one or more leaflets of the valve by a portion of the prosthetic valve.

For some embodiments, advancing the one or more valve support anchors includes: providing a respective delivery lumen coupled at a distal end thereof to each one of the one or more anchors, advancing each delivery lumen along a respective one of the one or more valve support guide members, facilitating anchoring of each one of the one or more anchors to the one or more commissures by the respective delivery lumen, and decoupling the delivery lumen from each one of the one or more valve support anchors following the anchoring of the one or more valve support anchors.

For some embodiments, the method includes removing the one or more valve support guide members from a body of the patient following the anchoring of each one of the one or more valve support anchors to the one or more commissures.

For some embodiments, the method includes advancing the prosthetic valve support along the one or more delivery lumens prior to the anchoring the support at the native atrioventricular valve.

For some embodiments, the valve support is shaped so as to define one or more holes, and advancing the valve support along the one or more delivery lumens includes threading the one or more delivery lumens through the one or more holes of the valve support and sliding the valve support along the one or more delivery lumens.

For some embodiments, the method includes removing the one or more delivery lumens from a body of the patient following the anchoring the support at the atrioventricular valve.

In accordance with some embodiments of the present disclosure, an apparatus may include a valve support for receiving a prosthetic valve, the valve support including: an annular element configured to be positioned along a native annulus of a native atrioventricular valve of a patient; and a flexible generally cylindrical element configured to be positioned in the native atrioventricular valve of the patient and to push aside native leaflets of the native valve, the cylindrical element having first and second ends and a cylindrical body that is disposed between the first and second ends, and: the first end of the cylindrical element is coupled to the annular element, during a first period, the second end of the cylindrical element is disposed above the annular element in a manner in which the body of the cylindrical element is disposed above the annular element, and the cylindrical element is invertible in a manner in which, during a second period, the second end of the cylindrical element is disposed below the annular element and the body of the cylindrical element is disposed below the annular element.

For some embodiments, the cylindrical element includes a flexible wireframe covered by a fabric.

For some embodiments, the valve support is collapsible for transcatheter delivery and expandable to contact the native atrioventricular valve.

For some embodiments, the annular element has an upper surface and a lower surface, the lower surface is coupled to one or more annular element tissue anchors configured to puncture tissue of the native annulus of the patient.

For some embodiments, the one or more annular element tissue anchors includes a plurality of annular element tissue anchors positioned around the lower surface of the annular element.

For some embodiments, the one or more annular element tissue anchors includes a first commissural annular element tissue anchor configured to puncture tissue of the native valve at a first commissure thereof, and a second commissural annular element tissue anchor configured to puncture tissue of the native valve at a second commissure thereof.

For some embodiments, each anchor of the one or more annular element tissue anchors includes a distal pointed tip and one or more radially-expandable prongs, the prongs being configured to expand and facilitate anchoring of the anchor and restrict proximal motion of the annular element tissue anchor.

For some embodiments, the apparatus includes one or more valve support guide members configured to be delivered to one or more commissures of the native atrioventricular valve of the patient, the one or more valve support guide members are configured to facilitate advancement of the valve support toward the native valve.

For some embodiments, the valve support is shaped so as to define one or more holes, the one or more holes configured to facilitate slidable passage therethrough of a respective one of the one or more valve support guide members.

For some embodiments, the one or more valve support guide members includes one valve support guide member that is looped through first and second commissures of the atrioventricular valve in a manner in which a looped portion of the valve support guide member is disposed in a ventricle of the patient and first and second free ends of the valve support guide member are accessible from a site outside a body of the patient.

For some embodiments, the apparatus includes one or more valve support tissue anchors configured to be advanceable along the one or more valve support guide members and anchored to the one or more commissures of the valve.

For some embodiments, the one or more valve support anchors includes one or more ventricular anchors, and the apparatus further includes one or more atrial anchors, each atrial anchor being configured to be advanced toward an atrial surface of the valve support and anchor in place the valve support in a vicinity of a respective one of the ventricular anchors.

For some embodiments, the valve support guide members are removable from the patient following the anchoring of the valve support at the atrioventricular valve.

For some embodiments, the one or more valve support anchors are configured to be anchored to the one or more commissures from ventricular surfaces thereof prior to advancement of the valve support.

For some embodiments, the one or more valve support tissue anchors includes first and second valve support tissue anchors, the first and second valve support tissue anchors being configured to be anchored to respective first and second commissures of the atrioventricular valve of the patient.

For some embodiments, the one or more valve support tissue anchors each include one or more radially-expandable prongs, and the one or more prongs are disposed within a sheath in a compressed state prior to the anchoring and exposed from within the sheath in order to expand and facilitate anchoring of the anchor to the respective commissures.

For some embodiments, the apparatus includes one or more prosthetic valve guide members reversibly couplable to the cylindrical element in a vicinity of the second end of the cylindrical element, the prosthetic valve guide members being configured to facilitate advancement of the prosthetic valve therealong and toward the valve support.

For some embodiments, the apparatus includes the prosthetic valve, and the prosthetic valve is couplable to the valve support.

For some embodiments, during the first period, the second end of the cylindrical element is disposed in an atrium of a heart of the patient and the annular element is positioned along an annulus of the native valve, the prosthetic valve is advanceable along the one or more prosthetic valve guide members into a ventricle of the heart of the patient, and in response to advancement of the prosthetic valve into the ventricle, the one or more prosthetic valve guide members are pulled into the ventricle and pull the second end of the cylindrical element into the ventricle to invert the cylindrical element.

For some embodiments, the prosthetic valve is collapsible for transcatheter delivery and expandable when exposed from within a delivery catheter.

For some embodiments, the prosthetic valve includes two or more prosthetic leaflets.

For some embodiments, the native atrioventricular valve includes a mitral valve, and the prosthetic valve includes three prosthetic leaflets.

For some embodiments, the prosthetic valve guide members are removable from the patient following the anchoring of the prosthetic valve at the atrioventricular valve.

For some embodiments, the prosthetic valve is shaped so as to define one or more snares configured to ensnare one or more native leaflets of the native valve of the patient.

In accordance with some embodiments of the present disclosure, a method may include advancing toward a native atrioventricular valve of a heart of a patient, a valve support including: an annular element, and a generally cylindrical element having first and second ends and a cylindrical body that is disposed between the first and second ends, the first end being coupled to the annular element; anchoring the annular element to an annulus of the native atrioventricular valve, following the anchoring, the second end of the cylindrical element is disposed above the annular element in an atrium of the heart, in a manner in which the body of the cylindrical element is disposed above the annular element; and following the anchoring, inverting the cylindrical element to pull the second end of the cylindrical element below the annular element and into a ventricle of the heart, in a manner in which the body of the cylindrical element is disposed below the annular element and pushes aside one or more native leaflets of the valve of the patient.

For some embodiments, anchoring the annular element to the annulus of the native atrioventricular valve includes:

advancing one or more valve support anchors that are distinct from the valve support toward one or more commissures of the heart, and anchoring the annular element to the annulus using the one or more positioning anchors.

For some embodiments, the annular element is coupled to one or more annular element tissue anchors, and anchoring the annular element includes pushing the one or more annular element tissue anchors into tissue of the annulus.

For some embodiments, inverting the cylindrical element includes advancing a prosthetic valve along one or more valve guide members reversibly coupled to the cylindrical element in a vicinity of the second end thereof, advancing the prosthetic valve includes advancing the prosthetic valve into the ventricle to pull the guide members and the second end of the cylindrical element into the ventricle, and the method further includes following the advancing of the prosthetic valve into the ventricle, pulling proximally the prosthetic valve such that a proximal portion of the valve contacts the valve support.

For some embodiments, pulling the prosthetic valve proximally includes ensnaring the one or more leaflets of the valve by a portion of the prosthetic valve.

In accordance with some embodiments of the present disclosure, an apparatus may include a valve support for receiving a prosthetic valve, the valve support including: an annular element configured to be positioned along a native annulus of a native atrioventricular valve of a patient, the annular element having upper and lower surfaces; and one or more annular element tissue anchors coupled to the lower surface of the annular element, the one or more annular element tissue anchors being configured to puncture tissue of the native annulus of the patient.

For some embodiments, the valve support is collapsible for transcatheter delivery and expandable to contact the native atrioventricular valve.

For some embodiments, the one or more annular element tissue anchors includes a plurality of annular element tissue anchors positioned around the lower surface of the annular element.

For some embodiments, the one or more annular element tissue anchors includes a first commissural annular element tissue anchor configured to puncture tissue of the native valve at a first commissure thereof, and a second commissural annular element tissue anchor configured to puncture tissue of the native valve at a second commissure thereof.

For some embodiments, each anchor of the one or more annular element tissue anchors includes a distal pointed tip and one or more radially-expandable prongs, the prongs being configured to expand and facilitate anchoring of the anchor and restrict proximal motion of the anchor.

For some embodiments, the apparatus includes one or more valve support guide members configured to be delivered to one or more commissures of the native atrioventricular valve of the patient, the one or more valve support guide members are configured to facilitate advancement of the valve support toward the native valve.

For some embodiments, the valve support is shaped so as to define one or more holes, the one or more holes configured to facilitate slidable passage therethrough of a respective one of the one or more valve support guide members.

For some embodiments, the one or more valve support guide members includes one valve support guide member that is looped through first and second commissures of the atrioventricular valve in a manner in which a looped portion of the valve support guide member is disposed in a ventricle of the patient and first and second free ends of the valve support guide member are accessible from a site outside a body of the patient.

For some embodiments, the apparatus includes one or more valve support tissue anchors that are distinct from the valve support and are configured to be advanceable along the one or more valve support guide members and anchored to the one or more commissures of the valve.

For some embodiments, the one or more valve support anchors includes one or more ventricular anchors, and the apparatus further includes one or more atrial anchors, each atrial anchor being configured to be advanced toward an atrial surface of the valve support and anchor in place the valve support in a vicinity of a respective one of the ventricular anchors.

For some embodiments, the one or more valve support guide members are removable from the patient following the anchoring of the valve support at the atrioventricular valve.

For some embodiments, the one or more valve support tissue anchors are configured to be anchored to the one or more commissures from ventricular surfaces thereof prior to advancement of the valve support.

For some embodiments, the one or more valve support tissue anchors includes first and second valve support tissue anchors, the first and second valve support tissue anchors being configured to be anchored to respective first and second commissures of the atrioventricular valve of the patient.

For some embodiments, the one or more valve support tissue anchors each include one or more radially-expandable prongs, and the one or more prongs are disposed within a sheath in a compressed state prior to the anchoring and exposed from within the sheath in order to expand and facilitate anchoring of the anchor to the respective commissures.

For some embodiments, the valve support further includes a flexible generally cylindrical element coupled to the annular element and configured to be positioned in the native atrioventricular valve of the patient and to push aside native leaflets of the native valve, the cylindrical element having first and second ends and a cylindrical body that is disposed between the first and second ends.

For some embodiments, the cylindrical element includes a flexible wireframe covered by a fabric.

For some embodiments, the apparatus includes one or more prosthetic valve guide members reversibly couplable to the cylindrical element in a vicinity of the second end of the cylindrical element, the prosthetic valve guide members being configured to facilitate advancement of the prosthetic valve therealong and toward the valve support.

For some embodiments, the apparatus includes the prosthetic valve, and the prosthetic valve is couplable to the valve support.

For some embodiments, the first end of the cylindrical element is coupled to the annular element, during a first period, the second end of the cylindrical element is disposed above the annular element in a manner in which the body of the cylindrical element is disposed above the annular element, and the cylindrical element is invertible in a manner in which, during a second period, the second end of the cylindrical element is disposed below the annular element and the body of the cylindrical element is disposed below the annular element.

For some embodiments, during the first period, the second end of the cylindrical element is disposed in an atrium of a heart of the patient, the prosthetic valve is advanceable along the one or more prosthetic valve guide members into a ventricle of the heart of the patient, and in response to advancement of the prosthetic valve into the ventricle, the one or more prosthetic valve guide members are pulled into the ventricle and pull the second end of the cylindrical element into the ventricle to invert the cylindrical element.

In accordance with some embodiments of the present disclosure, an apparatus may include one or more valve support guide members configured to be delivered to one or more commissures of a native atrioventricular valve of a patient; a prosthetic valve support configured to be advanced toward the native valve along the one or more valve support guide members and placed at the native valve; a prosthetic valve configured to be coupled to the valve support; and one or more sealing elements configured to facilitate sealing of an interface between the prosthetic valve support and the native valve.

For some embodiments, the sealing element includes a balloon disposed circumferentially around an outer surface of the prosthetic valve support.

For some embodiments, the sealing element includes one or more helices that are configured to facilitate sealing of commissures of the native valve with respect to the valve support by being wrapped around chordae tendineae of the native valve.

For some embodiments, the sealing element includes grasping elements that are configured to facilitate sealing of commissures of the native valve with respect to the valve support by grasping the commissures.

For some embodiments, the sealing element is configured to facilitate anchoring of the support to the native valve.

For some embodiments, the valve support is collapsible for transcatheter delivery and expandable to contact the native atrioventricular valve.

For some embodiments, the prosthetic valve includes two or more prosthetic leaflets.

For some embodiments, the native atrioventricular valve includes a mitral valve, and the prosthetic valve includes three prosthetic leaflets.

For some embodiments, the valve support guide members are removable from the patient following coupling of the prosthetic valve to the valve support.

For some embodiments, the valve support is shaped so as to define a distal portion which is configured to push aside, at least in part, native leaflets of the valve of the patient.

For some embodiments, the valve support is shaped so as to define one or more holes, the one or more holes being configured to facilitate slidable passage therethrough of a respective one of the one or more valve support guide members.

For some embodiments, the one or more valve support guide members includes one valve support guide member that is looped through first and second commissures of the atrioventricular valve in a manner in which a looped portion of the valve support guide member is disposed in a ventricle of the patient and first and second free ends of the valve support guide member are accessible from a site outside a body of the patient.

For some embodiments, the apparatus further includes: a guide wire configured to be advanced, via the native atrioventricular valve, into a ventricle of the patient, and coupled to an inner wall of the patient's ventricle; and a valve support guide member tube coupled to the guide wire, and a distal portion of the valve support guide member is configured to loop through the valve support guide member tube, such that, in response to the valve support guide member being pushed distally, portions of the valve support guide member are pushed to respective commissures of the native valve.

For some embodiments, the prosthetic valve is shaped so as to define one or more protrusions configured to ensnare one or more native leaflets of the native valve of the patient.

For some embodiments, the protrusions are disposed in a sinusoidal configuration such that the protrusions conform with a saddle shape of the patient's native annulus.

For some embodiments, the protrusions are configured to prevent the native leaflets from interfering with a left ventricular outflow tract of the patient, by sandwiching the leaflets between the protrusions and the prosthetic valve support.

For some embodiments, the valve support includes: a first end that is configured to be placed on an atrial side of a native atrioventricular valve of a patient; and a second end that is configured, during a first period, to be disposed inside the patient's atrium, above the first end of the valve support, the valve support being at least partially invertible in a manner in which, during a second period, the second end of the valve support is disposed at least partially inside a ventricle of the patient, below the first end of the valve support.

For some embodiments, the valve support includes an annular element and a generally cylindrical element coupled to the annular element, the generally cylindrical element being configured to push aside native leaflets of the native valve, and the cylindrical element has first and second ends and a cylindrical body that is disposed between the first and second ends.

For some embodiments, the sealing element includes a balloon disposed underneath the annular element and configured to facilitate sealing of an interlace between the annular element and the native valve.

For some embodiments, the apparatus further includes one or more prosthetic valve guide members, the prosthetic valve guide members being configured to facilitate advancement of the prosthetic valve therealong and toward the valve support.

For some embodiments, the first end of the cylindrical element is coupled to the annular element, during a first period, the second end of the cylindrical element is disposed above the annular element in a manner in which the body of the cylindrical element is disposed above the annular element, and the cylindrical element is invertible in a manner in which, during a second period, the second end of the cylindrical element is disposed below the annular element and the body of the cylindrical element is disposed below the annular element.

For some embodiments, during the first period, the second end of the cylindrical element is disposed in an atrium of a heart of the patient and the annular element is positioned along an annulus of the native valve, the prosthetic valve is advanceable along the one or more prosthetic valve guide members into a ventricle of the heart of the patient, and in response to advancement of the prosthetic valve into the ventricle, the one or more prosthetic valve guide members are pulled into the ventricle and pull the second end and the body of the cylindrical element into the ventricle to invert the cylindrical element.

In accordance with some embodiments of the present disclosure, an apparatus may include a prosthetic valve support configured to be advanced toward a native atrioventricular valve of a patient and placed at the native valve; a prosthetic valve configured to be coupled to the valve support, the prosthetic valve being shaped so as to define first and second sets of one or more protrusions, each set of protrusions configured to ensnare a respective native leaflet of the native valve of the patient, the first set of protrusions being disposed within a first circumferential arc with respect to a longitudinal axis of the prosthetic valve, on a first side of a distal end of the prosthetic valve, the second set of protrusions being disposed within a second circumferential arc with respect to the longitudinal axis of the prosthetic valve, on a second side of the distal end of the prosthetic valve, the first and second sets being disposed so as to provide first and second gaps therebetween at the distal end of the prosthetic valve, at least one of the gaps having a circumferential arc of at least 20 degrees; and one or more valve guide members configured to be delivered to one or ore commissures of the native valve, and to guide the valve such that the first and second circumferential arcs are aligned with respective leaflets of the native valve and such that the first and second gaps are aligned with respective commissures of the native valve.

For some embodiments, the at least one of the gaps has a circumferential are of at least 60 degrees.

For some embodiments, the first circumferential arc defines an angle of between 25 degrees and 90 degrees about the longitudinal axis of the prosthetic valve.

For some embodiments, the second circumferential arc defines an angle of between 25 degrees and 90 degrees about the longitudinal axis of the prosthetic valve.

For some embodiments, the first circumferential arc defines an angle of between 45 degrees and 75 degrees about the longitudinal axis of the prosthetic valve.

For some embodiments, the second circumferential arc defines an angle of between 45 degrees and 75 degrees about the longitudinal axis of the prosthetic valve.

In accordance with some embodiments of the present disclosure, a method may include determining an area defined by an annulus of a native atrioventricular valve of a patient; selecting a prosthetic valve to be placed in the native valve by determining that the valve defines a cross-sectional area that is less than 90% of the area defined by the annulus; and deploying the prosthetic valve at the native valve, the selecting of the prosthetic valve facilitating sealing of the native valve with respect to the prosthetic valve by facilitating closing of leaflets of the native valve around the prosthetic valve, upon deployment of the prosthetic valve.

For some embodiments, selecting the prosthetic valve includes selecting a prosthetic valve having a material disposed on an outer surface thereof.

For some embodiments, selecting the prosthetic valve includes selecting a prosthetic valve having a material that prevents tissue growth disposed on an outer surface thereof.

For some embodiments, selecting the prosthetic valve includes selecting a prosthetic valve having a material that promotes tissue growth disposed on an outer surface thereof.

For some embodiments, selecting the prosthetic valve to be placed in the native valve includes determining that the valve defines a cross-sectional area that is less than 80% of the area defined by the annulus.

For some embodiments, selecting the prosthetic valve to be placed in the native valve includes determining that the valve defines a cross-sectional area that is less than 60% of the area defined by the annulus.

In accordance with some embodiments of the present disclosure, an apparatus may include a valve support for receiving a prosthetic valve, the valve support including: a first end that is configured to be placed on an atrial side of a native atrioventricular valve of a patient; and a second end that is configured, during a first period, to be disposed inside the patient's atrium, above the first end of the valve support, the valve support being at least partially invertible in a manner in which, during a second period, the second end of the cylindrical element is disposed at least partially inside a ventricle of the patient, below the first end of the valve support.

For some embodiments, the valve support includes a flexible wireframe covered by a fabric.

For some embodiments, the valve support is collapsible for transcatheter delivery and expandable to contact the native atrioventricular valve.

For some embodiments, the valve support defines a surface that is an inner surface of the valve support during the first period, and an outer surface of the valve support during the second period, and the apparatus further includes a sealing material that is disposed on the surface, such that during the second period the sealing material facilitates sealing between the valve support and the native valve.

For some embodiments, the first end includes a coupling element configured to couple the valve support to tissue of the native valve on the atrial side of the native valve.

For some embodiments, the first end is shaped to define barbs that are configured to couple the valve support to tissue of the native valve on the atrial side of the native valve.

For some embodiments, the valve support includes: an annular element configured to be positioned along a native annulus of the native atrioventricular valve; and a flexible generally cylindrical element configured to be positioned in the native atrioventricular valve of the patient and to push aside native leaflets of the native valve, the first end of the cylindrical element defining the first end of the valve support, and the first end of the cylindrical element being coupled to the annular element.

For some embodiments, the apparatus further includes one or more valve support guide members configured to be delivered to one or more commissures of the native atrioventricular valve of the patient, and the one or more valve support guide members are configured to facilitate advancement of the valve support toward the native valve.

For some embodiments, the valve support is shaped so as to define one or more holes, the one or more holes configured to facilitate slidable passage therethrough of a respective one of the one or more valve support guide members.

For some embodiments, the one or more valve support guide members includes one valve support guide member that is looped through first and second commissures of the atrioventricular valve in a manner in which a looped portion of the valve support guide member is disposed in a ventricle of the patient and first and second free ends of the valve support guide member are accessible from a site outside a body of the patient.

For some embodiments, the apparatus further includes: a guide wire configured to be advanced, via the native atrioventricular valve, into a ventricle of the patient, and coupled to an inner wall of the patient's ventricle; and a valve support guide member tube coupled to the guide wire, and a distal portion of the valve support guide member is configured to loop through the valve support guide member tube, such that, in response to the valve support guide member being pushed distally, portions of the valve support guide member are pushed to respective commissures of the native valve.

For some embodiments, the apparatus further includes one or more prosthetic valve guide members reversibly couplable to the cylindrical element in a vicinity of the second end of the cylindrical element, the prosthetic valve guide members being configured to facilitate advancement of the prosthetic valve therealong and toward the valve support.

For some embodiments, the apparatus further includes the prosthetic valve, and the prosthetic valve is couplable to the valve support.

For some embodiments, during the first period, the second end of the cylindrical element is disposed in an atrium of a heart of the patient and the annular element is positioned along an annulus of the native valve, the prosthetic valve is advanceable along the one or more prosthetic valve guide members into a ventricle of the heart of the patient, and in response to advancement of the prosthetic valve into the ventricle, the one or more prosthetic valve guide members are pulled into the ventricle and pull the second end of the cylindrical element into the ventricle to invert the cylindrical element.

For some embodiments, the apparatus further includes one or more sealing elements configured to facilitate sealing of an interface between the prosthetic valve support and the native valve.

For some embodiments, the sealing element includes a balloon disposed circumferentially around a surface of the prosthetic valve support.

For some embodiments, the sealing element includes one or more helices that are configured to facilitate sealing of commissures of the native valve with respect to the valve support by being wrapped around chordae tendineae of the native valve.

For some embodiments, the sealing element includes grasping elements that are configured to facilitate sealing of commissures of the native valve with respect to the valve support by grasping the commissures.

For some embodiments, the sealing element is configured to facilitate anchoring of the support to the native valve.

For some embodiments, the apparatus further includes the prosthetic valve, and the prosthetic valve is couplable to the valve support.

For some embodiments, the prosthetic valve is collapsible for transcatheter delivery and expandable when exposed from within a delivery catheter.

For some embodiments, the prosthetic valve includes two or more prosthetic leaflets.

For some embodiments, the native atrioventricular valve includes a mitral valve, and the prosthetic valve includes three prosthetic leaflets.

For some embodiments, the prosthetic valve is shaped so as to define one or more protrusions configured to ensnare one or more native leaflets of the native valve of the patient.

For some embodiments, the protrusions are disposed in a sinusoidal configuration such that the protrusions conform with a saddle shape of the patient's native annulus.

For some embodiments, the protrusions are configured to prevent the native leaflets from interfering with a left ventricular outflow tract of the patient, by sandwiching the leaflets between the protrusions and the prosthetic valve support.

In accordance with some embodiments of the present disclosure, an apparatus may include a guide wire configured to be advanced into a patient's ventricle via a native atrioventricular valve of the patient, and coupled to an inner wall of the patient's ventricle; a valve support guide member tube coupled to the guide wire; a valve support guide member, a distal portion of the valve support guide member looping through the valve support guide member tube, such that, in response to the valve support guide member being pushed distally, portions of the valve support guide member are pushed to respective commissures of the native valve; a prosthetic valve support configured to be advanced toward the commissures of the native valve along the valve support guide member portions; and a prosthetic valve configured to be coupled to the valve support.

For some embodiments, first and second free ends of the valve support guide member are accessible from a site outside a body of the patient.

For some embodiments, the valve support includes: an annular element configured to be positioned along a native annulus of the native atrioventricular valve; and a generally cylindrical element configured to be positioned in the native atrioventricular valve of the patient and to push aside native leaflets of the native valve, the cylindrical element being coupled to the annular element, at a first end of the cylindrical element.

For some embodiments, the valve support is shaped so as to define one or more holes, the one or more holes configured to facilitate slidable passage therethrough of respective portions of the portions of the valve support guide member.

For some embodiments, the guide member is configured to facilitate advancement of the prosthetic valve therealong and toward the valve support.

For some embodiments, the prosthetic valve is collapsible for transcatheter delivery and expandable when exposed from within a delivery catheter.

For some embodiments, the prosthetic valve includes two or more prosthetic leaflets.

For some embodiments, the native atrioventricular valve includes a mitral valve, and the prosthetic valve includes three prosthetic leaflets.

For some embodiments, the guide member is removable from the patient following the coupling of the prosthetic valve to the valve support.

For some embodiments, the prosthetic valve is shaped so as to define one or more protrusions configured to ensnare one or more native leaflets of the native valve of the patient.

For some embodiments, the protrusions are disposed in a sinusoidal configuration such that the protrusions conform with a saddle shape of the patient's native annulus.

For some embodiments, the protrusions are configured to prevent the native leaflets from interfering with a left ventricular outflow tract of the patient, by sandwiching the leaflets between the protrusions and the prosthetic valve support.

For some embodiments, the apparatus further includes one or more sealing elements configured to facilitate sealing of an interface between the prosthetic valve support and the native valve.

For some embodiments, the sealing element includes a balloon disposed circumferentially around a surface of the prosthetic valve support.

For some embodiments, the sealing element includes one or more helices that are configured to facilitate sealing of commissures of the native valve with respect to the valve support by being wrapped around chordae tendineae of the native valve.

For some embodiments, the scaling element includes grasping elements that are configured to facilitate sealing of commissures of the native valve with respect to the valve support by grasping the commissures.

For some embodiments, the sealing element is configured to facilitate anchoring of the support to the native valve.

In accordance with some embodiments of the present disclosure, an apparatus may include one or more valve guide members configured to be delivered to one or more commissures of a native atrioventricular valve of a patient;

a prosthetic valve configured to be advanced to be advanced toward the native valve along the one or more valve guide members and placed at the native valve at at least the one or more commissures; and one or more proximally-facing grasping elements that are configured to facilitate sealing of commissures of the native valve with respect to the valve by: being inserted into a ventricle of the patient; and being pulled proximally and being closed around tissue in a vicinity of the commissures.

For some embodiments, the grasping elements include two surfaces that are hingedly coupled to one another, and that are configured to facilitate the sealing of the commissures of the native valve with respect to the prosthetic valve by being closed about the hinge with respect to one another.

In accordance with some embodiments of the present disclosure, a method may include advancing one or more valve support guide members toward one or more commissures of a native atrioventricular valve of a patient; placing a prosthetic valve support at the native atrioventricular valve by advancing the valve support along the one or more valve support guide members; coupling a prosthetic valve to the prosthetic valve support; and facilitating sealing of an interface between the prosthetic valve support and the native valve by deploying a sealing element in a vicinity of the interface.

In accordance with some embodiments of the present disclosure, a method may include placing a first end of a prosthetic valve support on an atrial side of a native atrioventricular valve of a patient, such that a second end of the valve support is disposed, during a first period, inside the patient's atrium, above the first end of the valve support; and subsequent to the placing of the valve support, inverting at least a portion of the valve support such that, during a second period, the second end of the valve support is disposed at least partially inside a ventricle of the patient, below the first end of the valve support.

In accordance with some embodiments of the present disclosure, a method may include advancing a guide wire, via a native atrioventricular valve, into a ventricle of the patient, a valve support guide member tube being coupled to the guide wire; coupling a distal end of the guide wire to an inner wall of the patient's ventricle; and causing portions of a valve support guide member to be pushed to respective commissures of the native valve, by pushing the guide member distally, a distal portion of the valve support guide member looping through the valve support guide member tube; advancing a prosthetic valve support toward the commissures of the native valve along the valve support guide member portions; and coupling a prosthetic valve to the valve support.

In accordance with some embodiments of the present disclosure, a method may include advancing one or more valve guide members toward one or more commissures of a native atrioventricular valve of a patient; placing a prosthetic valve at the native atrioventricular valve by advancing the valve along the one or more valve guide members; and facilitating sealing of commissures of the native valve with respect to the valve by: inserting into a ventricle of the patient one or more grasping elements that are coupled to the prosthetic valve; pulling the grasping elements proximally; and closing the grasping elements around tissue in a vicinity of the commissures.

The present disclosure will be more fully understood from the following detailed description of embodiments thereof, taken together with the drawings, in which:

BRIEF DESCRIPTION OF THE DRAWINGS

FIGS. 3A-B are schematic illustrations of the advancement of a prosthetic valve support toward a native atrioventricular valve of a patient, the valve support including a sealing balloon, in accordance with some embodiments of the present disclosure;

FIGS. 4A-C are schematic illustrations of a valve support being used with commissural helices that facilitate anchoring and/or sealing of the valve support, in accordance with some embodiments of the present disclosure;

FIGS. 5A-D are schematic illustrations of grasping elements being used to anchor and/or provide sealing of a prosthetic valve, in accordance with some embodiments of the present disclosure;

FIGS. 7A-F are schematic illustrations of a guide wire delivery system, in accordance with some embodiments of the present disclosure;

FIG. 10 is a schematic illustration of a prosthetic valve, the cross-sectional area of which is smaller than the area defined by the patient's native valve annulus, in accordance with some embodiments of the present disclosure;

FIGS. 11A-D are schematic illustrations of a prosthetic valve that defines protrusions from portions of the distal end of the valve, in accordance with some embodiments of the present disclosure;

FIGS. 12A-C are schematic illustrations of a prosthetic valve that defines distal protrusions that are disposed sinusoidally around the circumference of the valve, in accordance with some embodiments of the present disclosure;

FIGS. 13A-E are schematic illustrations of respective configurations of a frame of a prosthetic valve, in accordance with some embodiments of the present disclosure;

FIGS. 14A-D are schematic illustrations of respective configurations of a prosthetic valve support, in accordance with some embodiments of the present disclosure;

FIGS. 16A-H are schematic illustrations of respective steps of an alternative procedure for deploying a prosthetic valve, in accordance with some embodiments of the present disclosure;

FIGS. 19A-D are schematic illustrations of the valve support of FIGS. 18A-B being implanted in the native valve of the patient and facilitating implantation of a prosthetic valve, in accordance with embodiments of the present disclosure.

DETAILED DESCRIPTION OF THE EMBODIMENTS

Figure 1A:
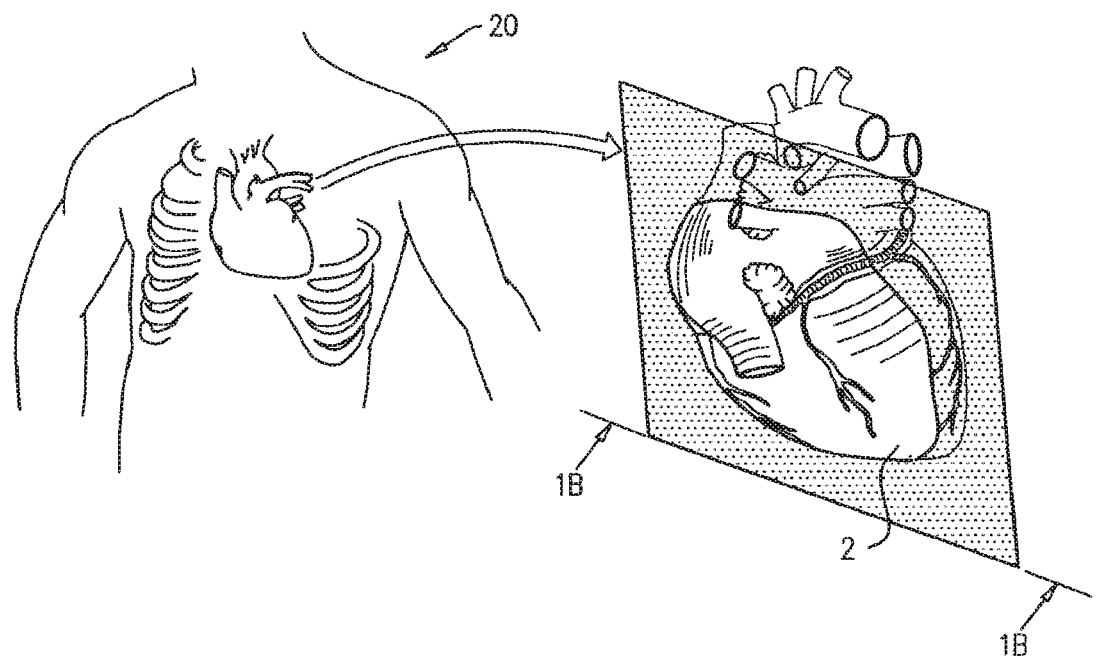
FIGS. 1A-B are schematic illustrations of advancement of one or more guide members toward respective commissures of a mitral valve, in accordance with some embodiments of the present disclosure.
Figure 1B:
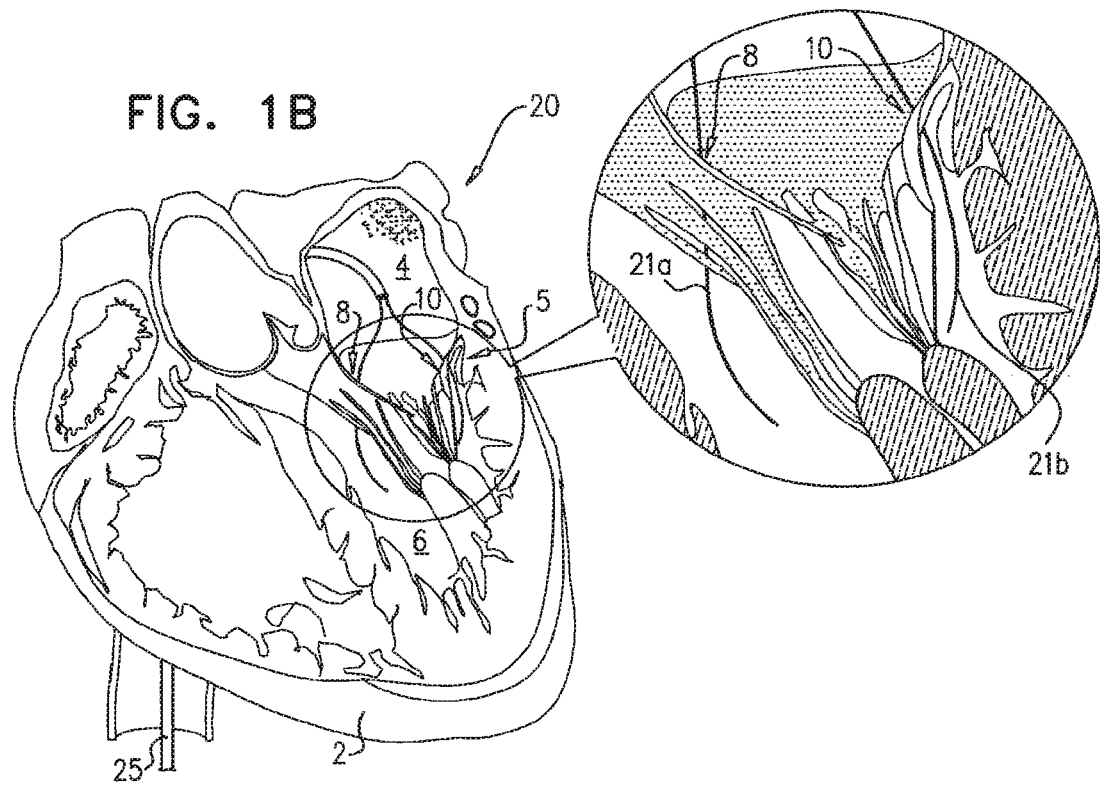
Figure 1C:
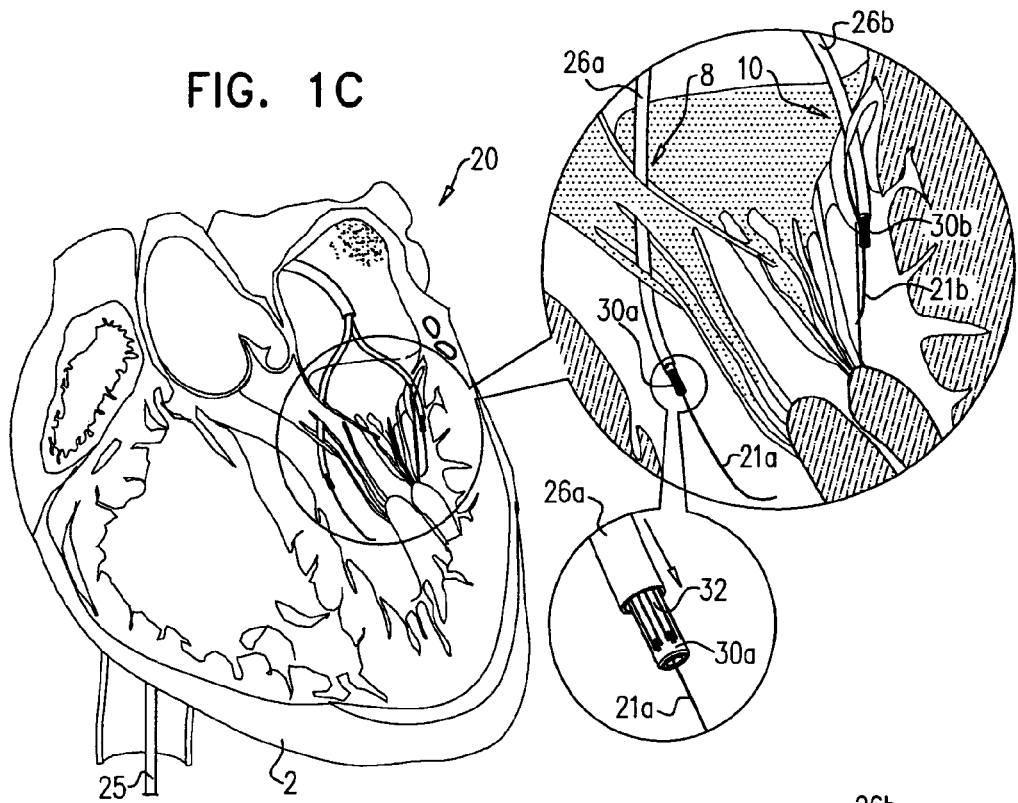
FIGS. 1C-D are schematic illustrations of the advancement and deployment of commissural anchors via the guide members, in accordance with some embodiments of the present disclosure.

Reference is now made to FIGS. 1A-B, which are schematic illustrations of a system 20 for replacing an atrioventricular valve 5 of a patient including one or more guide members 21a and 21b which are advanced toward first and second commissures 8 and 10 of valve 5 of a heart 2 of the patient, in accordance with some embodiments of the present disclosure. For some embodiments, guide members 21a and 21b include distinct guide members. Alternatively (as shown in FIGS. 7A-F), only one guide member is looped through commissures 8 and 10 in a manner in which the guide member defines a looped portion between commissures 8 and 10 (i.e., a portion of the guide member that is disposed in a ventricle 6 of heart 2), and first and second free ends which are disposed and accessible at a site outside the body of the patient. For such embodiments, the guide member defines portions 21a and 21b.

It is noted that for embodiments in which valve 5 is the patient's mitral valve, first and second commissures 8 and 10 are the anterior and posterior commissures. For embodiments in which valve 5 is the patient's tricuspid valve (which includes three commissures), the first and second commissures may be the anterior and posterior commissures of the tricuspid valve.

For some embodiments, guide members 21a and 21b include guide wires having a diameter of 0.035 inches.

The transcatheter procedure in some embodiments begins with the advancing of a semi-rigid guide wire into a right atrium 4 of the patient. The semi-rigid guide wire provides a guide for the subsequent advancement of a sheath 25 therealong and into the right atrium. Once sheath 25 has entered the right atrium, the semi-rigid guide wire is retracted from the patient's body. Sheath 25 in some embodiments includes a 13-20 F sheath, although the size may be selected as appropriate for a given patient. Sheath 25 is advanced through vasculature into the right atrium using a suitable point of origin in some embodiments determined for a given patient. For example: sheath 25 may be introduced into the femoral vein of the patient, through an inferior vena cava, into the right atrium, and into the left atrium transseptally, in some embodiments through the fossa ovalis; sheath 25 may be introduced into the basilic vein, through the subclavian vein to the superior vena cava, into the right atrium, and into the left atrium transseptally, in some embodiments through the fossa ovalis; or sheath 25 may be introduced into the external jugular vein, through the subclavian vein to the superior vena cava, into the right atrium, and into the left atrium transseptally, in some embodiments through the fossa ovalis.

In some embodiments of the present disclosure, sheath 25 is advanced through the inferior vena cava of the patient and into the right atrium using a suitable point of origin in some embodiments determined for a given patient.

Sheath 25 is advanced distally until sheath 25 reaches the interatrial septum. For some embodiments, a resilient needle and a dilator (not shown) are advanced through the sheath and into the heart. In order to advance the sheath transseptally into the left atrium, the dilator is advanced to the septum, and the needle is pushed from within the dilator and is allowed to puncture the septum to create an opening that facilitates passage of the dilator and subsequently the sheath therethrough and into the left atrium. The dilator is passed through the hole in the septum created by the needle. In some embodiments, the dilator is shaped to define a hollow shaft for passage along the needle, and the hollow shaft is shaped to define a tapered distal end. This tapered distal end is first advanced through the hole created by the needle. The hole is enlarged when the gradually increasing diameter of the distal end of the dilator is pushed through the hole in the septum.

The advancement of sheath 25 through the septum and into the left atrium is followed by the extraction of the dilator and the needle from within sheath 25.

FIGS. 1C-D and 2A-B show advancement of one or more tissue anchors 30a and 30b (alternatively, "tissue anchor bases 30a and 30b") along guide members 21a and 21b, respectively. Tissue anchor bases 30a and 30b include a flexible, biocompatible material (e.g., nitinol) and include one or more (e.g., a plurality of) radially-expandable prongs 32 (alternatively, "leaves 32") which may include, e.g., barbs. Each tissue anchor base 30a and 30b is reversibly coupled to a respective delivery mechanism, such as delivery lumen 27a and 27b. Each delivery lumen 27 slides around a respective guide member 21. A respective surrounding sheath 26a and 26b surrounds each delivery lumen 27a and 27b and around tissue anchor bases 30a and 30b at least in part in order to compress and prevent expansion of the leaves 32 of tissue anchor bases 30a and 30b.

Figure 1D:
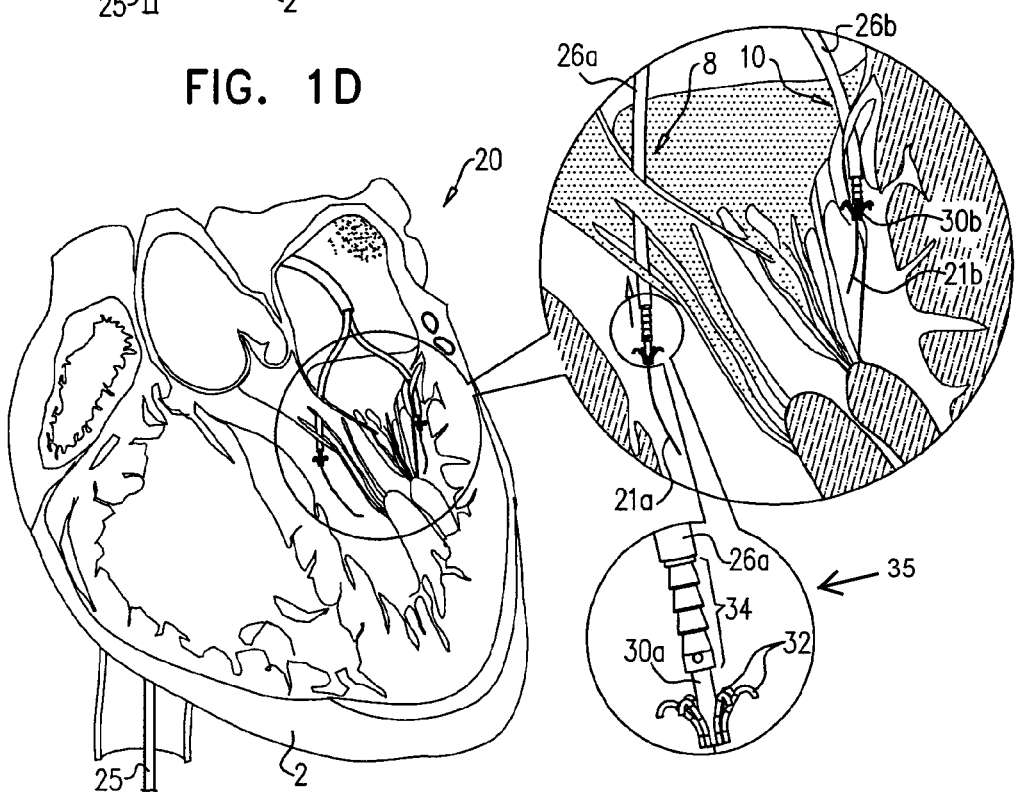

As shown in FIG. 1D, the distal ends of lumens 27a and 27b are reversibly coupled to ribbed crimping structures 34. As described hereinbelow, tissue anchor bases 30a and 30b are anchored to ventricular surfaces of commissures 8 and 10. Following the anchoring, ribbed crimping structures 34 extend from tissue anchor bases 30a and 30b through commissures 8 and 10, respectively, and toward the atrial surfaces of commissures 8 and 10. Ribbed crimping structures 34 are configured to facilitate anchoring of a valve support (described hereinbelow) to the atrial surfaces of commissures 8 and 10. Tissue anchor bases 30 and crimping structures 34 may together constitute a tissue anchor 35, which may be configured to anchor a valve support (via engagement of the valve support with crimping structures 34) to the ventricular surfaces of commissures 8 and 10 (via anchor bases 30).

Anchor bases 30*a* and 30*b*, ribbed crimping structures 34, and the distal ends of surrounding sheaths 26*a* and 26*b* are advanced into ventricle 6. Subsequently, anchor bases 30*a* and 30*b* are pushed distally from within sheaths 26*a* and 26*b*, (or sheaths 26*a* and 26*b* are pulled proximally with respect to anchor bases 30*a* and 30*b*) to expose anchor bases 30*a* and 30*b*. As anchor bases 30*a* and 30*b* are exposed from within sheaths 26*a* and 26*b*, leaves 32 are free to expand and splay outward, as shown in FIG. 1D. Leaves 32 expand such that anchor bases 30*a* and 30*b* assume a flower shape. Leaves 32, collectively in their expanded state, create a larger surface area to engage tissue than in their compressed states. Following the exposing of anchor bases 30*a* and 30*b*, sheaths 26*a* and 26*b* are extracted.

Figure 2A:
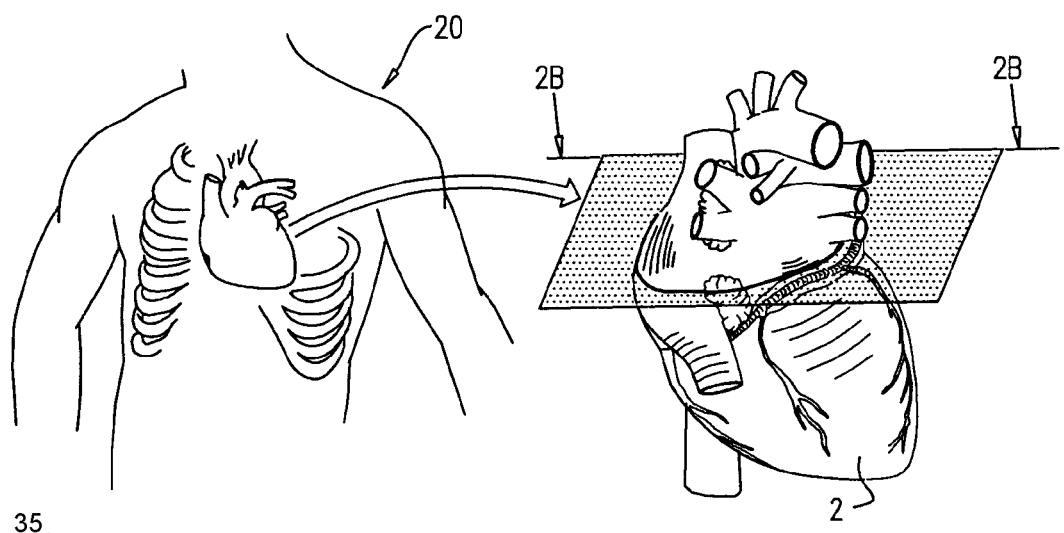
FIGS. 2A-D are schematic illustrations of the advancement of a prosthetic valve support toward a native atrioventricular valve of a patient, in accordance with some embodiments of the present disclosure.
Figure 2B:
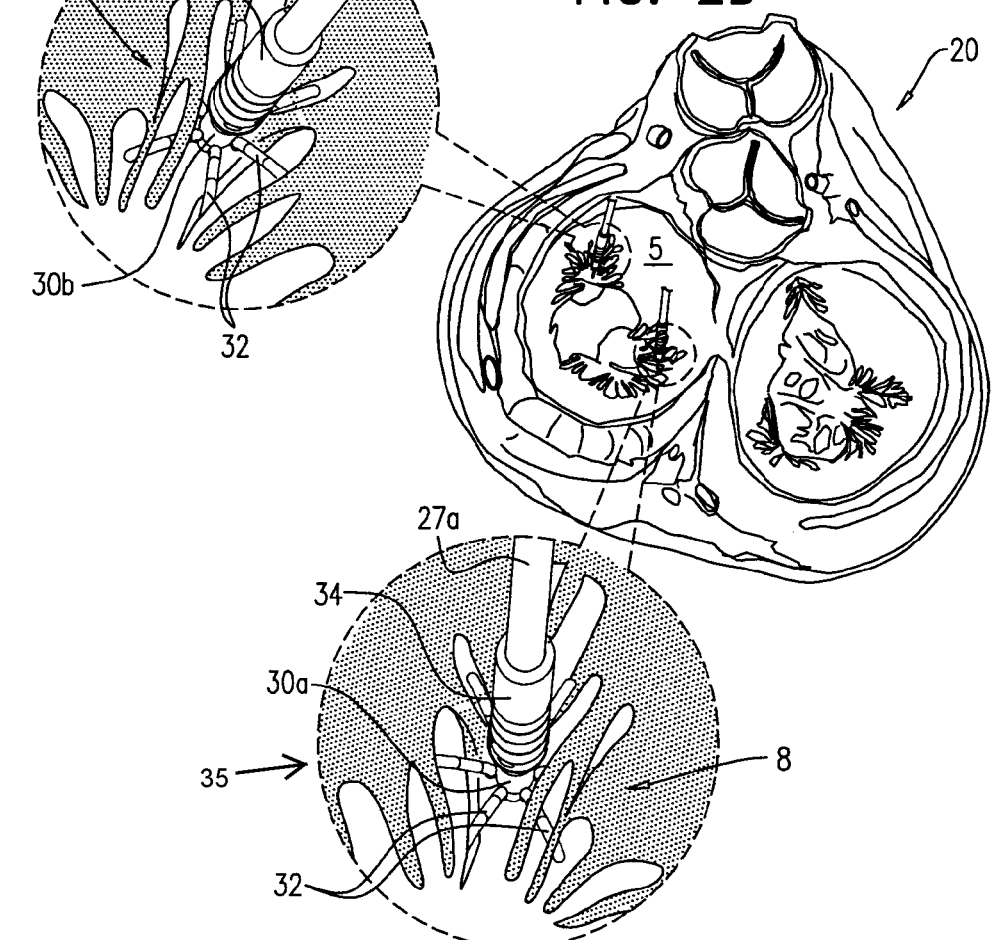

As shown in FIG. 2B, lumens 27*a* and 27*b* are pulled proximally so that leaves 32 of anchor bases 30*a* and 30*b* engage respective ventricular surface of commissures 8 and 10. Leaves 32 create a large surface area which restricts proximal motion of anchor bases 30*a* and 30*b* from commissures 8 and 10, respectively.

For some embodiments, following the anchoring of anchor bases 30*a* and 30*b* to commissures 8 and 10, respectively, guide members 21*a* and 21*b* are removed from the body of the patient.

Figure 2C:
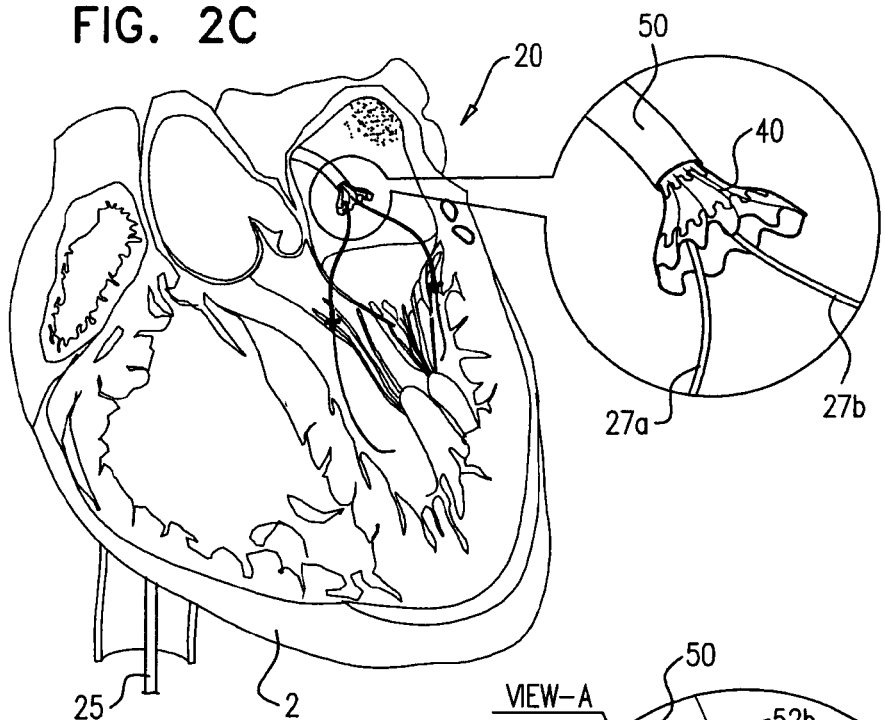
Figure 2D:
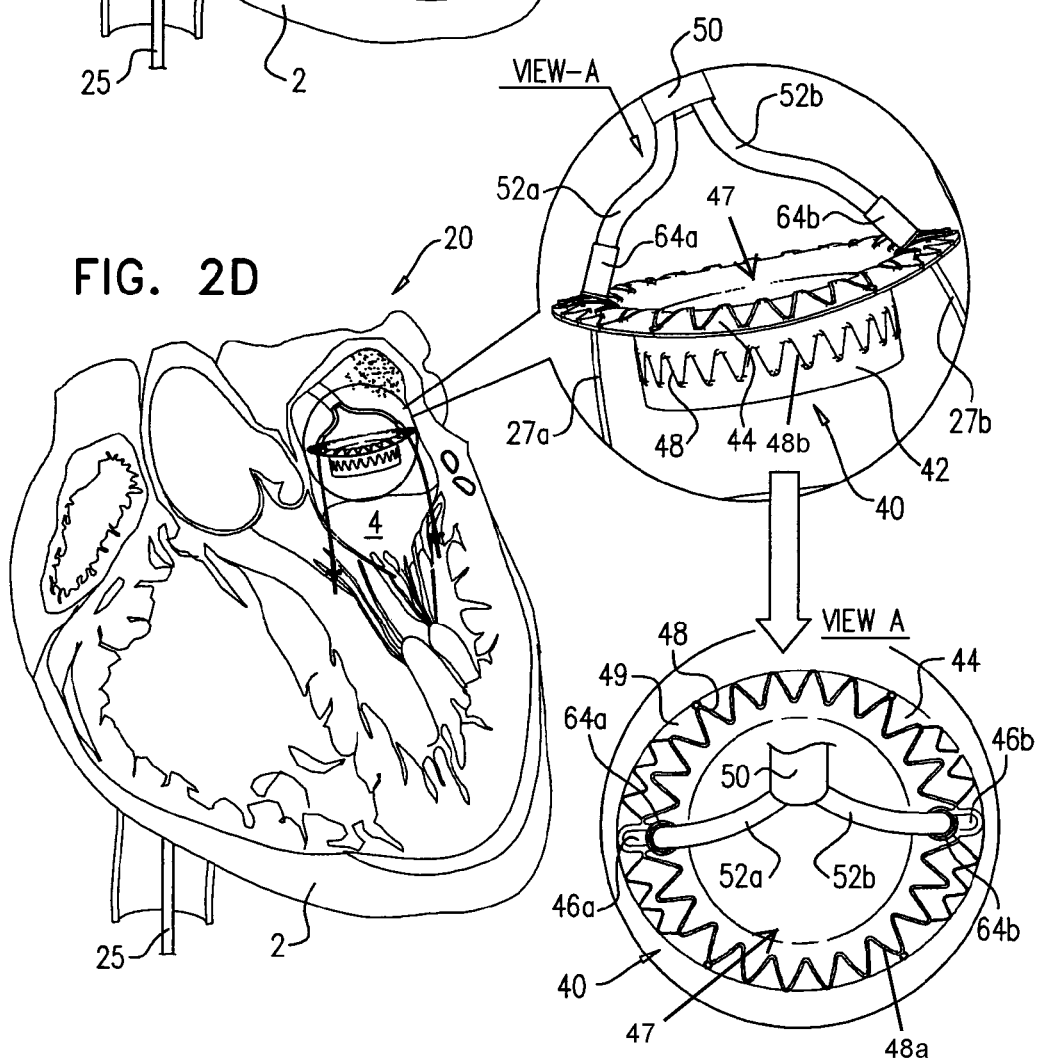

Reference is now made to FIGS. 2C-F, which are schematic illustrations of the advancement of a prosthetic valve support 40 (alternatively, "annular spacer 40") along lumens 27*a* and 27*b*, in accordance with some embodiments of the present disclosure. In such a manner, lumens 27*a* and 27*b* function as spacer guide members. As illustrated in FIG. 2D, spacer 40 may be annular, with a spacer opening 47 extending therethrough. Spacer 40 is collapsible and includes a proximal annular element 44 (alternatively, "wall 44") and a distal cylindrical element 42 (alternatively, "cylindrical skirt 42"). As illustrated in FIG. 2D, in some embodiments wall 44 may be substantially flattened or planar, thus rendering wall 44 disc-shaped. As also illustrated in FIG. 2D, an outer diameter of cylindrical skirt 42 may be smaller than an outer diameter of disc-shaped wall 44. Spacer opening 47 may extend through disc-shaped wall 44 and cylindrical skirt 42. Thus, spacer opening 47 may define an inner diameter of disc-shaped wall 44 and cylindrical skirt 42. Spacer 40 is configured to assume a collapsed state (e.g., surrounded by a sheath or overtube 50 shown in FIG. 2O) for minimally-invasive delivery to the diseased native valve, such as by percutaneous or transluminal delivery using one or more catheters. FIG. 2C and the other figures show spacer 40 in an expanded state after delivery in right atrium 4 and advancement toward the native valve. As shown in FIG. 2D, spacer 40 is shaped so as to define one or more (e.g., two, as shown in View A) holes 46*a* and 46*b* for slidable advancement of spacer 40 along lumens 27*a* and 27*b*, respectively. That is, prior to introduction of spacer 40 into the body of the patient, lumens 27*a* and 27*b* are threaded through holes 46*a* and 46*b*, respectively, and spacer 40 is slid along lumens 27*a* and 27*b*. Spacer 40 is slid by pushing elements 52*a* and 52*b* which surround delivery lumens 27*a* and 27*b*, respectively.

It is to be noted that spacer 40 is slid along lumens 27*a* and 27*b* by way of illustration and not limitation. That is, for some embodiments, following the anchoring of tissue anchor bases 30*a* and 30*b* to commissures 8 and 10, respectively, guide members 21*a* and 21*b* are not removed from the body of the patient, but rather lumens 27*a* and 27*b* are removed (e.g., by being decoupled from crimping structures 34) leaving behind tissue anchor bases 30*a* and 30*b* and guide members 21*a* and 21*b*. Guide members 21*a* and 21*b* may then be threaded through holes 46*a* and 46*b*, respectively, and spacer 40 is slid along guide members 21*a* and 21*b*. In such a manner, guide members 21*a* and 21*b* function as spacer guide members.

Figure 2E:
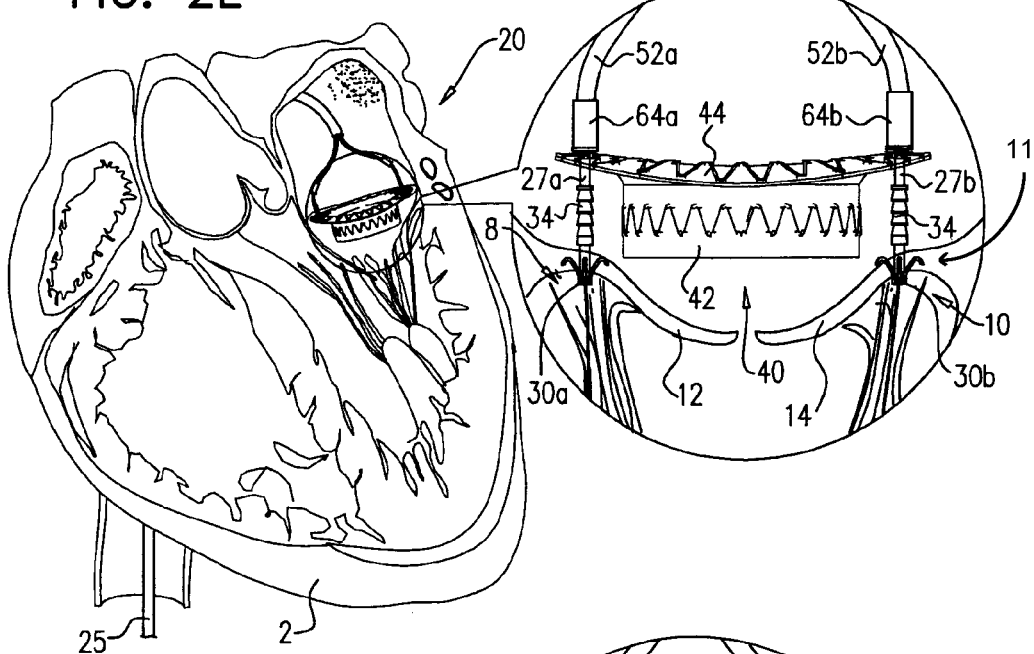
FIGS. 2E-F are schematic illustrations of locking of the prosthetic valve support at the native valve, in accordance with some embodiments of the present disclosure.

Spacer 40 includes a collapsible flexible support stent 48, which is at least partially covered by a covering 49. Spacer 40 is configured to be placed at native valve 5, such that cylindrical skirt 42 passes through the orifice of the native valve and extends towards, and, in some embodiments partially into, ventricle 6 (as shown in FIG. 2E). Since cylindrical skirt 42 may be configured to sit within the orifice of the native valve, spacer 40 may be configured such that spacer opening 47 (which defines the inner diameter of cylindrical skirt 42) may have a smaller diameter than the native valve orifice. For example, as illustrated in FIG. 2E, spacer 40 may be configured such that spacer opening 47 may have a smaller diameter than native annulus 11. Cylindrical skirt 42 in some embodiments pushes aside and presses against native leaflets of native valve 5 at least in part, which are left in place during and after implantation of the central valve section 80. Disc-shaped wall 44 is configured to be placed around a native annulus 11 of the native valve, and to extend at least partially into an atrium 4 such that disc-shaped wall 44 rests against the native annulus. Disc-shaped wall 44 is in some embodiments too large to pass through the annulus, and may, for example, have an outer diameter of between 30 and 60 mm.

For some embodiments, collapsible support stent 48 includes a plurality of struts. As illustrated in FIG. 2D, stent 48 may include struts 48*a* positioned within disc-shaped wall 44 and struts 48*b* positioned within cylindrical skirt 42. The struts may include, for example, a metal such as nitinol or stainless steel. For some embodiments, stent 48 includes a flexible metal, e.g., nitinol, which facilitates compression of spacer 40 within a delivery sheath or overtube 50. For some embodiments, covering 49 includes a fabric, such as a woven fabric, e.g., Dacron. Covering 49 is in some embodiments configured to cover at least a portion of cylindrical skirt 42, and at least a portion of disc-shaped wall 44. The covering may include a single piece, or a plurality of pieces sewn together. Disc-shaped wall 44 may be configured to at least partially obstruct blood flow therethrough due, at least in part, to the presence of stent 48 and/or due to the arrangement of covering 49 upon stent 48.

As shown in FIG. 2D, pushing elements 52*a* and 52*b* are each coupled to locking crimping elements 64*a* and 64*b*, respectively. Locking crimping elements 64*a* and 64*b* are disposed adjacently, proximally to holes 46*a* and 46*b* respectively of spacer 40. These techniques enable the surgeon to readily bring crimping elements 64*a* and 64*b* to the appropriate sites along disc-shaped wall 44, without the need for excessive imaging, such as fluoroscopy.

FIG. 2E shows spacer 40 prior to implantation at annulus 11. As shown, ribbed crimping structures 34 project away from tissue anchor bases 30*a* and 30*b*, through commissures 8 and 10, and toward atrium 4. Spacer 40 is advanced along lumens 27*a* and 27*b* toward structures 34 by being pushed by pushing elements 52*a* and 52*b* and locking crimping elements 64*a* and 64*b*.

Figure 2F:
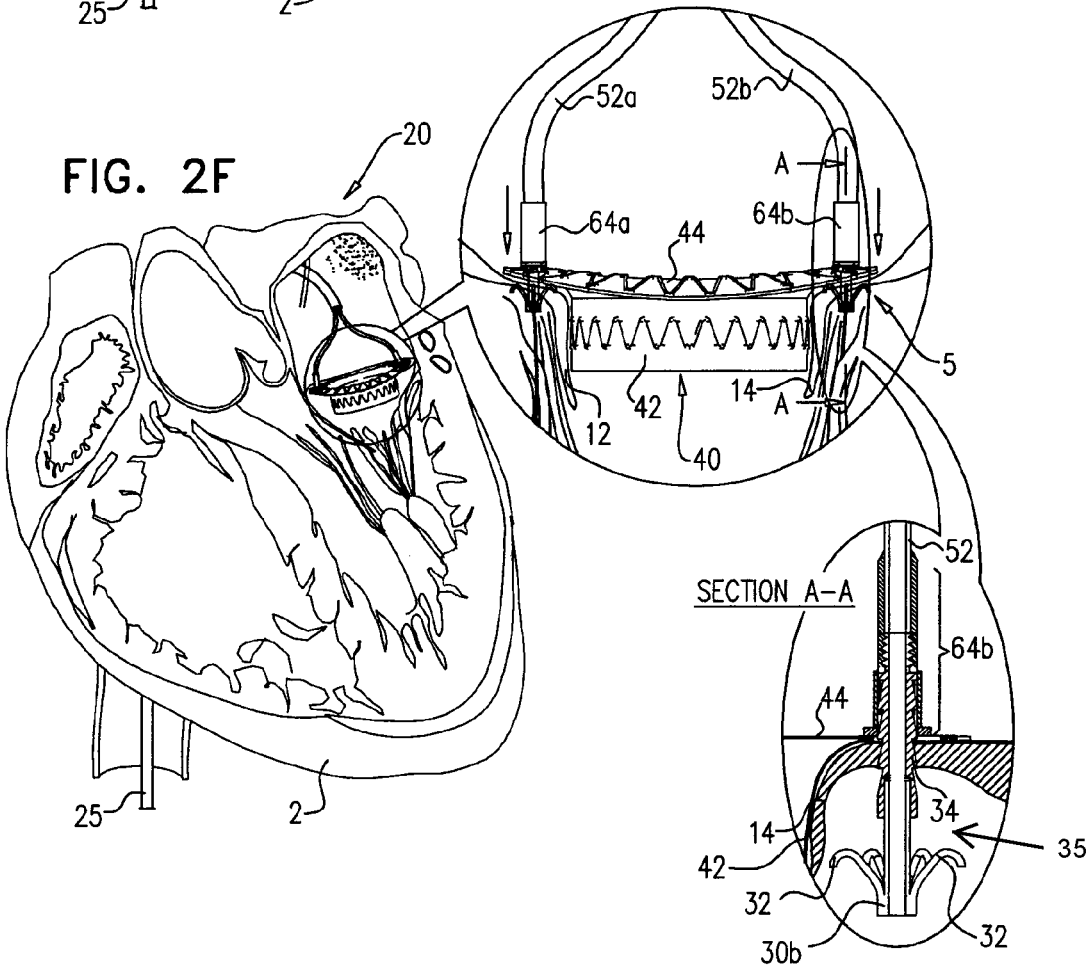

In FIG. 2F, spacer 40 is further pushed by pushing elements 52*a* and 52*b* and locking crimping elements 64*a* and 64b such that holes 46a and 46b of spacer 40 advance around ribbed crimping structures 34. As holes 46a and 46b are advanced around ribbed crimping structures 34, locking crimping elements 64a and 64b advance over and surround ribbed crimping elements 34 to lock in place spacer 40 from an atrial surface of valve 5.

Responsively to the placement of spacer 40 at native valve 5, cylindrical skirt 42 is positioned partially within ventricle 6 and native leaflets 12 and 14 of native valve 5 are pushed aside.

As shown in section A-A, ribbed crimping structures 34 of tissue anchors 35 are shaped so as to define a plurality of male couplings. Locking crimping elements 64a and 64b each include a cylindrical element having an inner lumen that is shaped so as to surround a respective ribbed crimping structure 34. Each inner lumen of locking crimping elements 64a and 64b is shaped so as to define female couplings to receive the male couplings of ribbed crimping structure 34. The female couplings of locking crimping element 64 are directioned such that they facilitate distal advancement of locking crimping element 64 while restricting proximal advancement of locking crimping element 64. When the female couplings of locking crimping element 64 receive the male couplings of ribbed crimping structure 34, spacer 40 is locked in place from an atrial surface of valve 5. It is to be noted that for some embodiments, ribbed crimping elements 34 include female couplings, and locking crimping elements 64 include male couplings.

Reference is now made to FIGS. 2G-K which are schematic illustrations of the coupling of a central valve section 80 to spacer 40, in accordance with some embodiments of the present disclosure. Spacer 40 receives the central valve section 80 within spacer opening 47 and functions as a docking station. Thus, the docking station is a coupling element that provides coupling between two other elements (in this case, between annulus 11 and central valve section 80.)

Figure 2G:
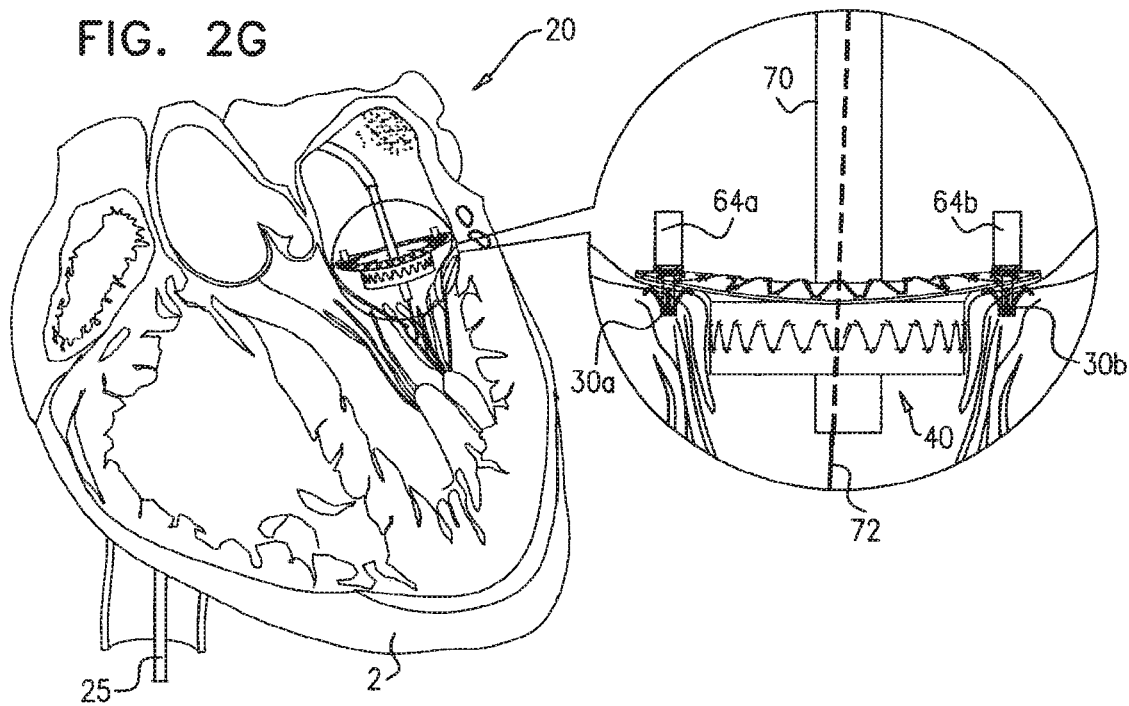
FIGS. 2G-K are schematic illustrations of the advancement of a prosthetic valve and the coupling of the prosthetic valve to the valve support, in accordance with some embodiments of the present disclosure.

Following the placement of spacer 40 at annulus 11, pushing elements 52a and 52b and sheath or overtube 50 are removed from the body of the patient, leaving behind lumens 27a and 27b, as shown in FIG. 2G.

As shown in FIG. 2G, a guide wire 72 is advanced toward ventricle 6 and facilitates the advancement of an overtube 70 through sheath 25 and the positioning of a distal end of overtube 70 within ventricle 6. Overtube 70 facilitates the advancement of central valve section 80 in a compressed state, toward spacer 40.

Figure 2H:
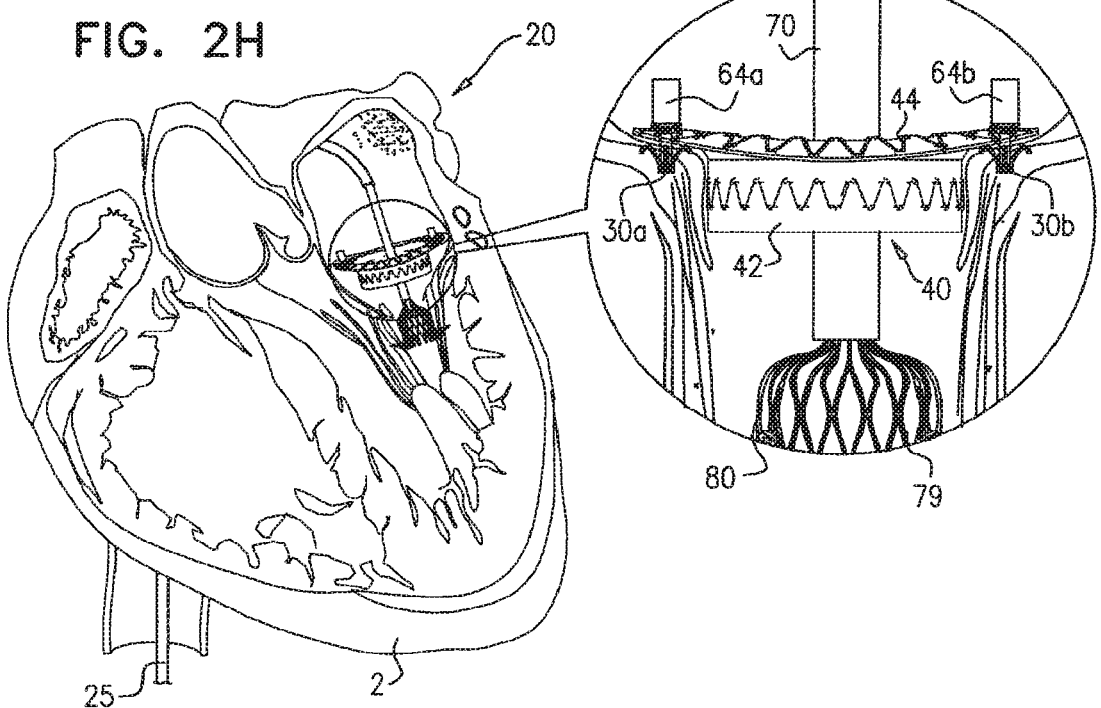

FIG. 2H shows partial deployment of central valve section 80 within ventricle 6 of heart 2. Central valve section 80 is shown including an expandable frame 79 including a plurality of stent struts 79a by way of illustration and not limitation. The wireframe of central valve section 80 includes a flexible metal, e.g., nitinol or stainless steel. It is to be noted that the wireframe of central valve section 80 is covered by a covering (not shown for clarity of illustration) including a braided mesh or in a fabric such as a woven fabric, e.g., Dacron. The covering is in some embodiments configured to cover at least a portion of the frame. The covering may include a single piece, or a plurality of pieces sewn together. Expandable frame 79 is in some embodiments self-expandable, although the scope of the present disclosure includes using a prosthetic valve that includes a balloon expandable frame, mutatis mutandis.

Figure 2I:
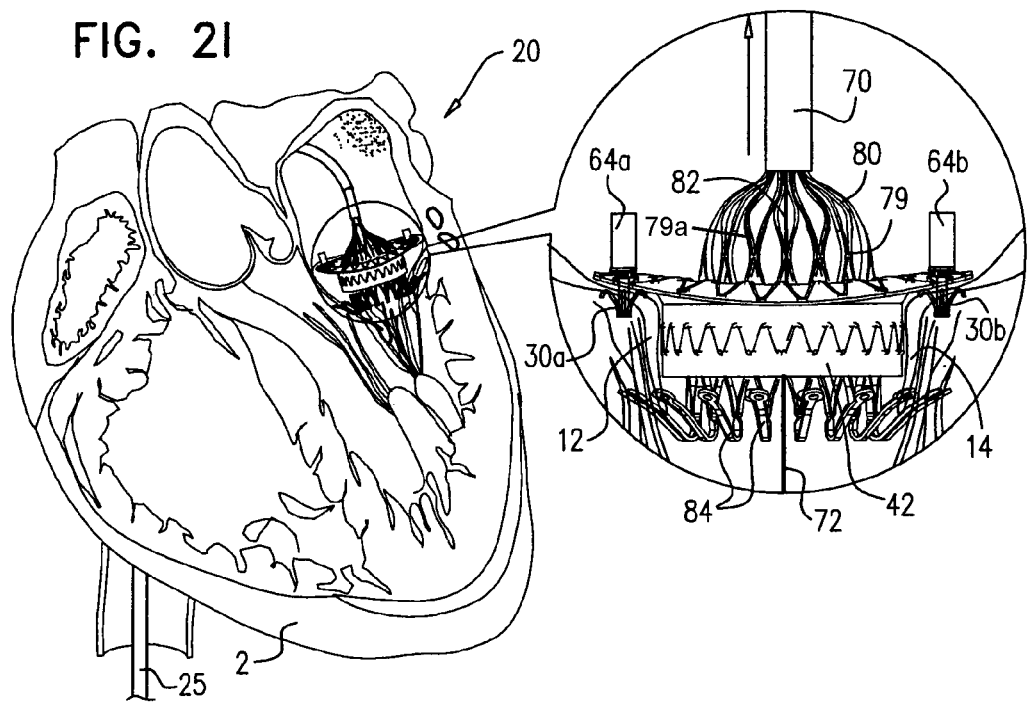
Figure 2J:
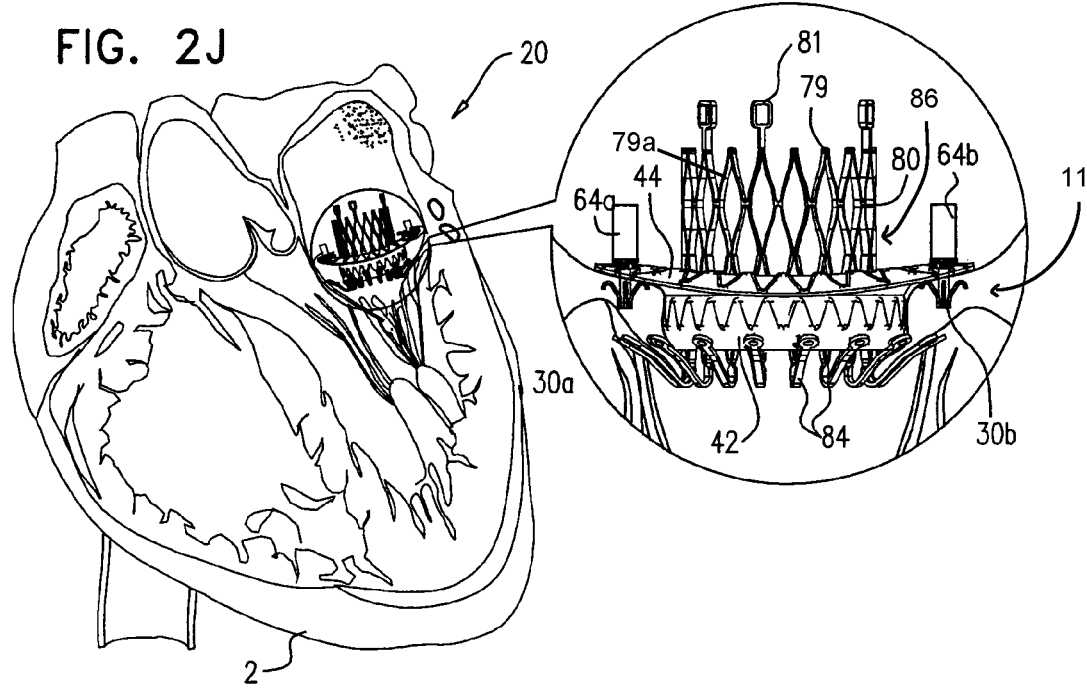

Following the partial deployment of central valve section 80 in ventricle 6, overtube 70 is pulled proximally to pull central valve section 80 proximally such that cylindrical skirt 42 and/or disc-shaped wall 44 of spacer 40 surrounds a proximal portion of central valve section 80. Central valve section 80 may be configured to expand such that central valve section 80, in particular cylindrical portion 86 thereof, is held in place with respect to spacer 40 responsively to radial forces acted upon spacer 40 by central valve section 80. Because spacer 40 and central valve section 80 are configured to be implanted separately and to engage one another within the body, spacer 40 and central valve section 80 may be separable such that the features can be disengaged (e.g. by contracting central valve section 80 and removing it from spacer 40. In addition, and as illustrated in FIG. 2J, an outer diameter of cylindrical portion 86 of the central valve section may be smaller than the diameter of native annulus 11 due, at least in part, to the engagement between expanded cylindrical portion 86 and spacer 40.

Central valve section 80 includes a plurality of distal protrusions 84 (e.g., snares). As illustrated in FIGS. 2I and 2J, protrusions 84 are configured to extend radially outward beyond cylindrical skirt 42 of the annular spacer. When central valve section 80 is pulled proximally, as described hereinabove, protrusions 84 ensnare and engage the native leaflets of the atrioventricular valve. By the ensnaring of the native leaflets, protrusions 84 sandwich the native valve between protrusions 84 and spacer 40. Such ensnaring helps further anchor central valve section 80 to the native atrioventricular valve. The scope of the present disclosure includes using any sort of protrusions (e.g., hooks) that protrude from the distal end of expandable frame 79 of central valve section 80 and that are configured such that the native valve is sandwiched between the protrusions and spacer 40. In some embodiments, the protrusions cause sandwiching of the native valve leaflets, such that the leaflets do not interfere with the left ventricular outflow tract (LVOT).

For some embodiments, protrusions 84 are such as to (a) prevent proximal migration of the central valve section into the patient's atrium, while (b) allowing movement of the native leaflets with respect to the frame of the central valve section. For example, the protrusions may have the aforementioned functionalities by having lengths of less than 5 mm, and/or by a total width of each set of protrusions corresponding to respective leaflets of the native valve being less than 5 mm. For example, the central valve section may include a single protrusion corresponding to each leaflet of the native valve, the width of each of the single protrusions being less than 1 mm. Thus, the central valve section may be stopped from proximally migrating into the atrium, by the protrusions preventing the distal end of the central valve section from migrating further proximally than edges of native leaflets of the valve. Furthermore, the protrusions may allow movement of the native leaflets with respect to the frame of the central valve section by not generally squeezing the native leaflets between the protrusions and the frame of the central valve section. For some embodiments, by allowing movement of the native leaflets with respect to the frame of the central valve section, sealing of the native leaflets against the outer surface of the frame of the central valve section is facilitated, in accordance with the techniques described hereinbelow with reference to FIG. 10. In some embodiments, spacer 40 prevents the central valve section from migrating distally into the patient's ventricle.

For some embodiments, during the procedure, the central valve section is pulled back proximally with respect to the annular spacer, as described hereinabove. The central valve section is pulled back to a position with respect to the annular spacer that is such that protrusions 84 prevent the native leaflets from interfering with the LVOT, by sandwiching the native leaflets between the protrusions and the annular spacer, and/or by anchoring ends of the native leaflets as described hereinabove. The central valve section is then deployed at this position.

For some embodiments, protrusions are disposed on the central valve section on the sides of the central valve section that are adjacent to the anterior and posterior leaflets of the native valve, and the central valve section does not includes protrusions on the portions of the central valve section that are adjacent to the commissures of the native valve, as described with reference to FIGS. 11A-D. For some embodiments, the protrusions are disposed in a sinusoidal configuration in order to conform with the saddle shape of the native valve, as described hereinbelow with reference to FIGS. 12A-C.

Additionally, as shown in FIG. 2J, central valve section 80 includes one or more (e.g., a plurality, as shown) coupling elements 81 at the proximal end of central valve section 80. Overtube 70, which facilitates the advancement of central valve section 80, is reversibly coupled to central valve section 80, via coupling elements 81.

Central valve section 80 is configured for implantation in and/or at least partial replacement of a native atrioventricular valve 5 of the patient, such as a native mitral valve or a native tricuspid valve. Central valve section 80 is configured to assume a collapsed state for minimally-invasive delivery to the diseased native valve, such as by percutaneous or transluminal delivery using one or more catheters. FIG. 2J shows central valve section 80 in an expanded state after delivery to the native valve.

Figure 2K:
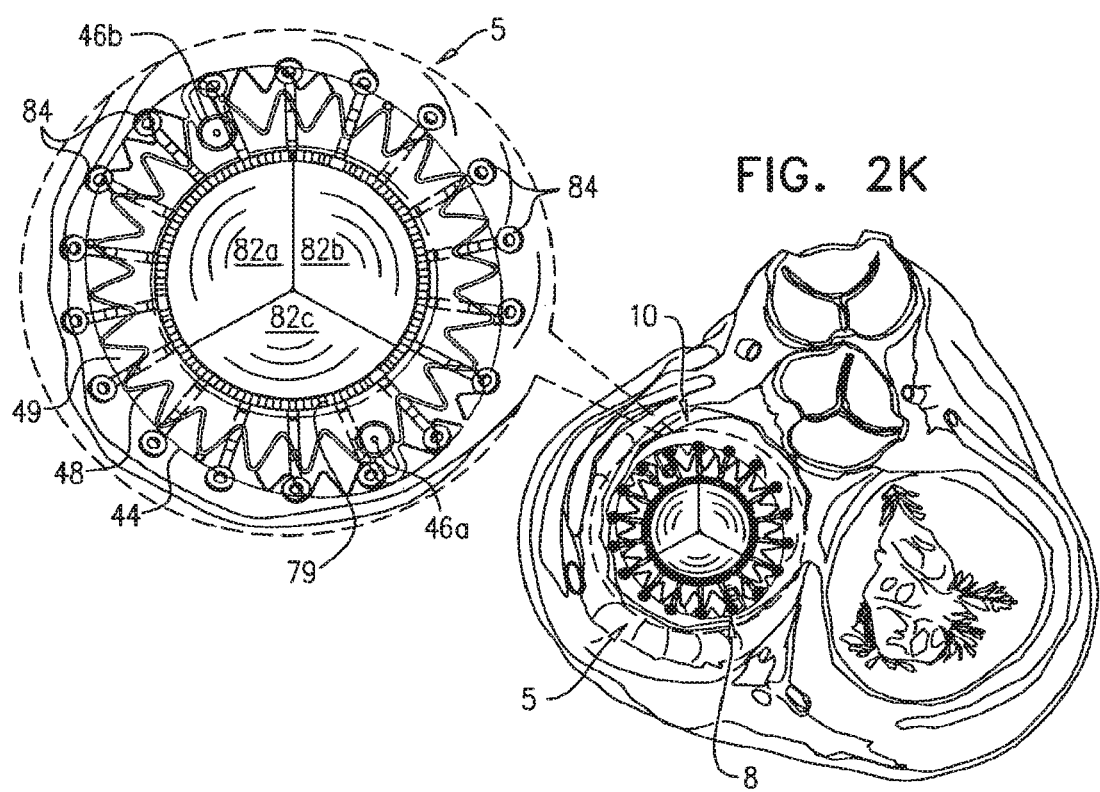

Reference is now made to FIG. 2K which shows a bird's-eye view of central valve section 80. Central valve section 80 further includes a plurality of valve leaflets 82, which may be artificial or tissue-based. The leaflets are in some embodiments coupled to an inner surface of the central valve section. Leaflets 82 are coupled, e.g., sewn, to expandable frame 79 and/or to the covering. For embodiments in which the central valve section is configured to be implanted at the native mitral valve, the central valve section in some embodiments includes three leaflets 82a, 82b, and 82c, as shown in FIG. 2K.

Figure 3C:
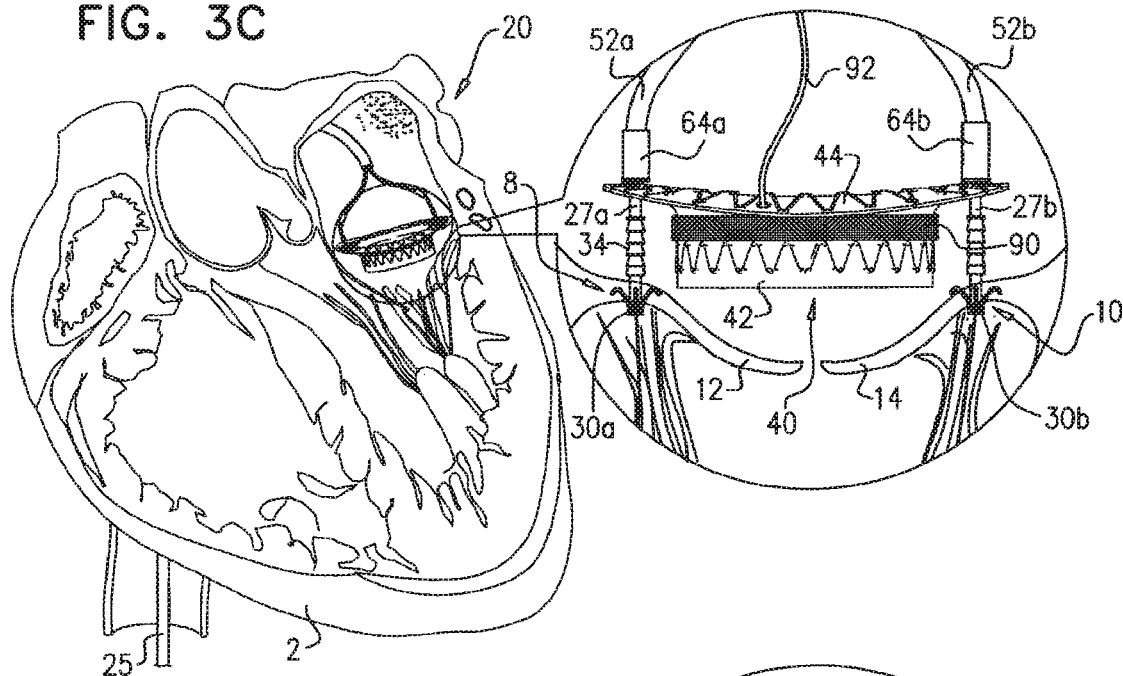
FIGS. 3C-D are schematic illustrations of locking of the prosthetic valve support at the native valve, the valve support including the sealing balloon, in accordance with some embodiments of the present disclosure.
Figure 3D:
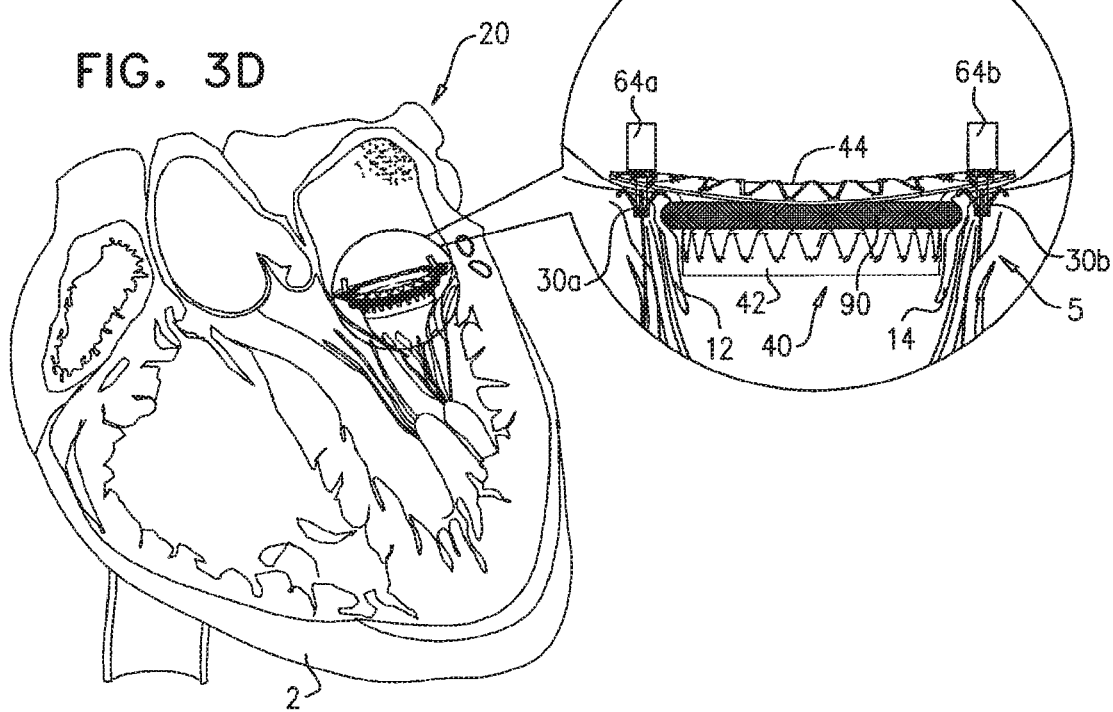

Reference is now made to FIGS. 3A-D, which are schematic illustrations of the advancement of spacer 40 toward native atrioventricular valve 5 of a patient, the annular spacer including a sealing balloon 90, in accordance with some embodiments of the present disclosure. The steps shown in FIGS. 3A-C are generally similar to those shown in FIGS. 2C-F. For some embodiments, sealing balloon 90 is disposed on the valve-facing, lower side of disc-shaped wall 44 of the annular spacer. FIG. 3D shows spacer 40, the spacer having been implanted at annulus 11. In some embodiments, at this stage, balloon 90 is inflated, as shown in the transition from FIG. 3O to FIG. 3D. The balloon is inflated via an inflation lumen 92, shown in FIG. 3C, for example. For some embodiments, the balloon seals the interface between the spacer and native annulus 11, thereby reducing retrograde blood flow from ventricle 6 into atrium 4, relative to retrograde blood flow in the absence of a sealing balloon. For some embodiments, the balloon is inflated prior to the placement of the prosthetic support at annulus 11.

Figure 4B:
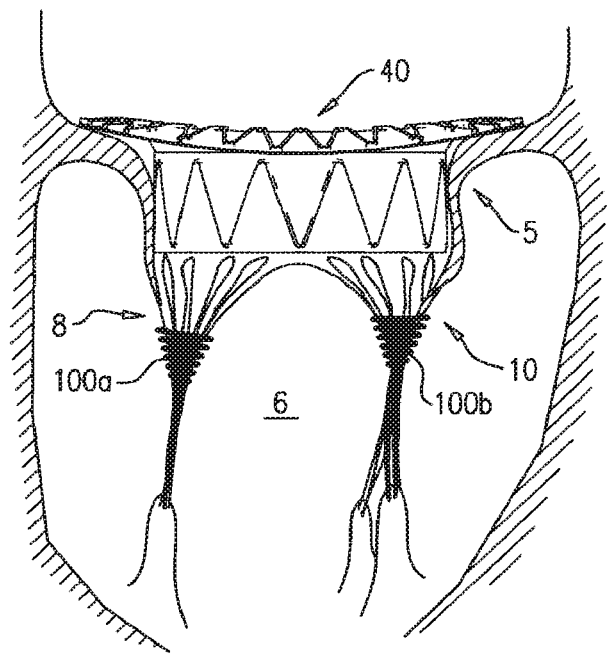
Figure 4C:
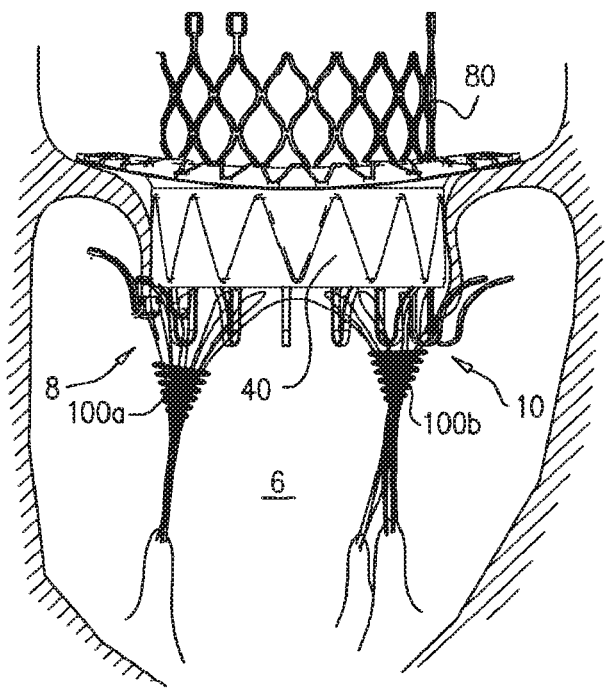

Reference is now made to FIGS. 4A-C, which are schematic illustrations of spacer 40 being used with commissural helices 100a and 100b that facilitate anchoring and/or sealing of the spacer, in accordance with some embodiments of the present disclosure. For some embodiments, commissural helices are used as an alternative or in addition to tissue anchor bases 30a and 30b and/or other anchoring elements described herein, in order to facilitate the anchoring of spacer 40.

Commissural helices 100a and 100b are in some embodiments placed at commissures 8 and 10 in a generally similar technique to that described with reference to tissue anchor bases 30a and 30b. In some embodiments, each helix 30a and 30b is reversibly coupled to a respective delivery lumen 27a and 27b. As described above, each delivery lumen 27 slides around a respective guide member 21, and a respective surrounding sheath 26a and 26b surrounds each delivery lumen 27a and 27b.

Commissural helices 100a and 100b (optionally, ribbed crimping structures 34), and the distal ends of surrounding sheaths 26a and 26b are advanced into ventricle 6. The helices are pushed out of the distal ends of surrounding sheaths 26a and 26b. Subsequently, the helices are rotated proximally such that the helices wrap around at least some chordae tendineae 102 of the patient. Following the advancement of the helices out of sheaths 26a and 26b, the sheaths are extracted. For some embodiments the helices are conical helices (as shown), and the wider end of the conical helix is disposed at the proximal end of the helix.

Subsequent to the placement of commissural helices 100a and 100b around the chordae tendineae, spacer 40 is placed at annulus 11, in accordance with the techniques described hereinabove, and as shown in FIG. 4B. Subsequently, central valve section 80 is coupled to spacer 40, in accordance with the techniques described hereinabove, and as shown in FIG. 4C.

In some embodiments, commissural helices 100a and 100b facilitate sealing of native commissures 8 and 10, thereby reducing retrograde blood flow via the commissures, relative to retrograde blood flow in the absence of the helices. Further in some embodiments, the sealing of the native commissures facilitates anchoring of the spacer to native valve 5.

Figure 5A:
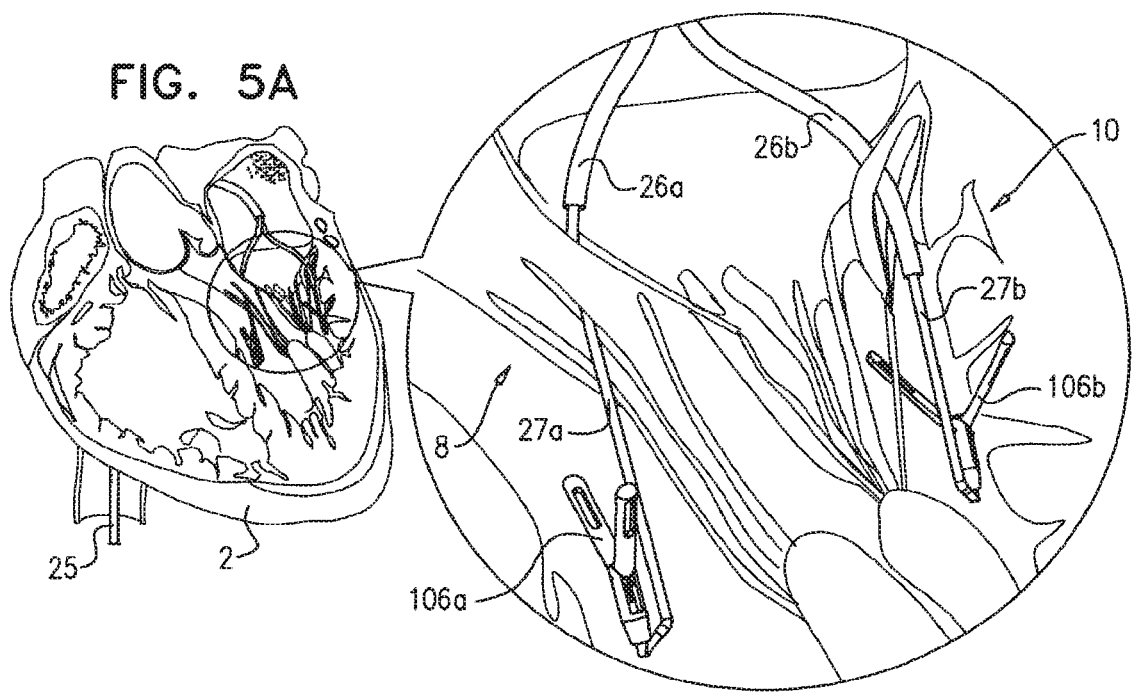

Reference is now made to FIGS. 5A-D, which are schematic illustrations of grasping elements 106a and 106b being used to anchor central valve section 80, in accordance with some embodiments of the present disclosure. For some embodiments, guide members 21a and 21b are advanced toward first and second commissures 8 and 10 of valve 5 of the patient, as described hereinabove. Grasping elements 106a and 106b are reversibly coupled to distal ends of delivery lumen 27a and 27b, the delivery lumens being advanced over respective guide members, as described hereinabove. For some embodiments, the guiding members and the grasping elements are advanced toward the patient's commissures via surrounding sheaths 26a and 26b, the surrounding sheaths being generally as described hereinabove. The grasping elements are in some embodiments placed distally to the commissures in a proximally-facing configuration, as shown in FIG. 5A. For example, as shown, the grasping elements may be configured to be proximally facing due to the coupling of the grasping elements to the guide members.

Figure 5B:
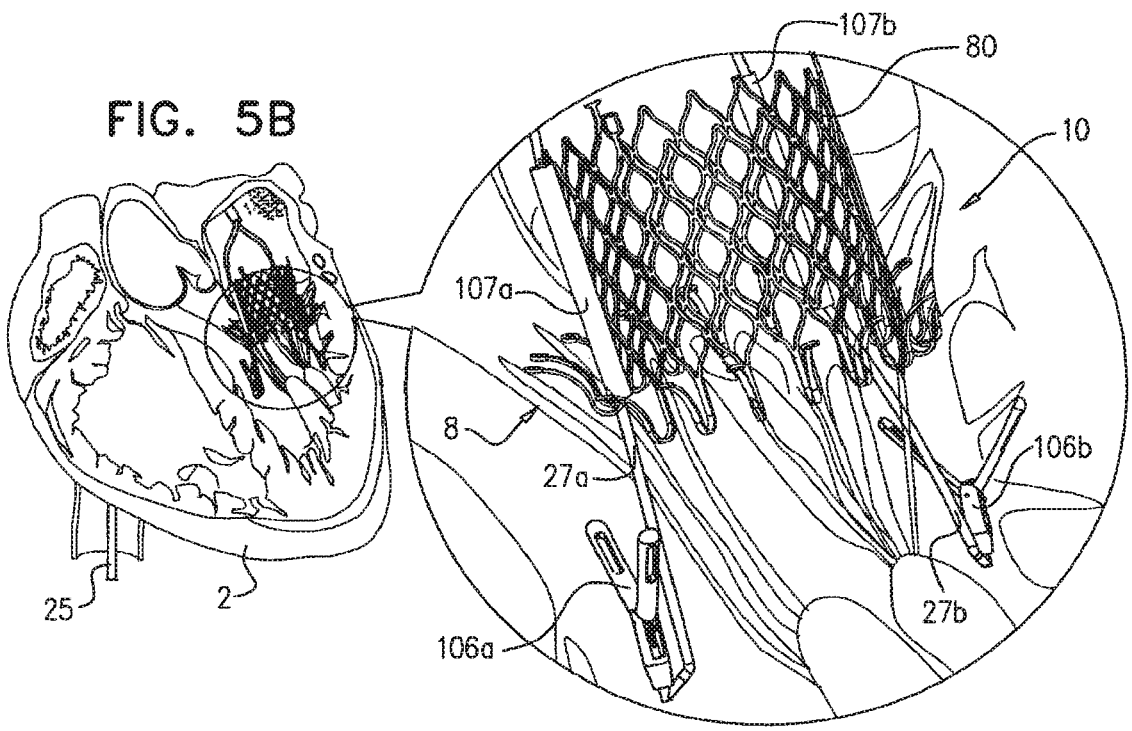

Subsequent to the placement of grasping elements 106a and 106b distally to native commissures 8 and 10, central valve section 80 is advanced toward native valve 5, as shown in FIG. 5B. For example, the central valve section may be advanced over delivery lumens 27a and 27b, as shown. The central valve section is placed at the native valve and, subsequently, the grasping elements are retracted proximally toward commissures 8 and 10, as shown in the transition from FIG. 5B to FIG. 5C. For some embodiments, the grasping elements are coupled to central valve section 80 via coupling tubes 107a and 107b, the coupling tubes being coupled to the sides of the central valve section, as shown. The grasping elements are closed such that the native commissures are grasped and sealed by the grasping elements, as shown in FIG. 5D. In some embodiments, the grasping elements define two surfaces that are hingedly coupled to each other. For example, the grasping elements may include forceps, as shown. The grasping elements are closed by closing the surfaces about the hinge, with respect to one another.

In some embodiments, grasping elements 106a and 106b facilitate sealing of native commissures 8 and 10, thereby reducing retrograde blood flow via the commissures, relative to retrograde blood flow in the absence of the grasping elements. Further in some embodiments, the sealing of the native commissures facilitates anchoring of the central valve section to native valve 5.

Although not shown, for some embodiments, spacer 40 is used in addition to grasping elements 106a and 106b, in order to anchor central valve section 80 to native valve 5. For some embodiments, the grasping elements are used to anchor and/or provide sealing for spacer 40 (instead of, or in addition to, being used to anchor central valve section 80, as shown). For such embodiments, generally similar techniques are used to those described with respect to the use of the grasping elements for anchoring the central valve section, mutatis mutandis.

Figure 6A:
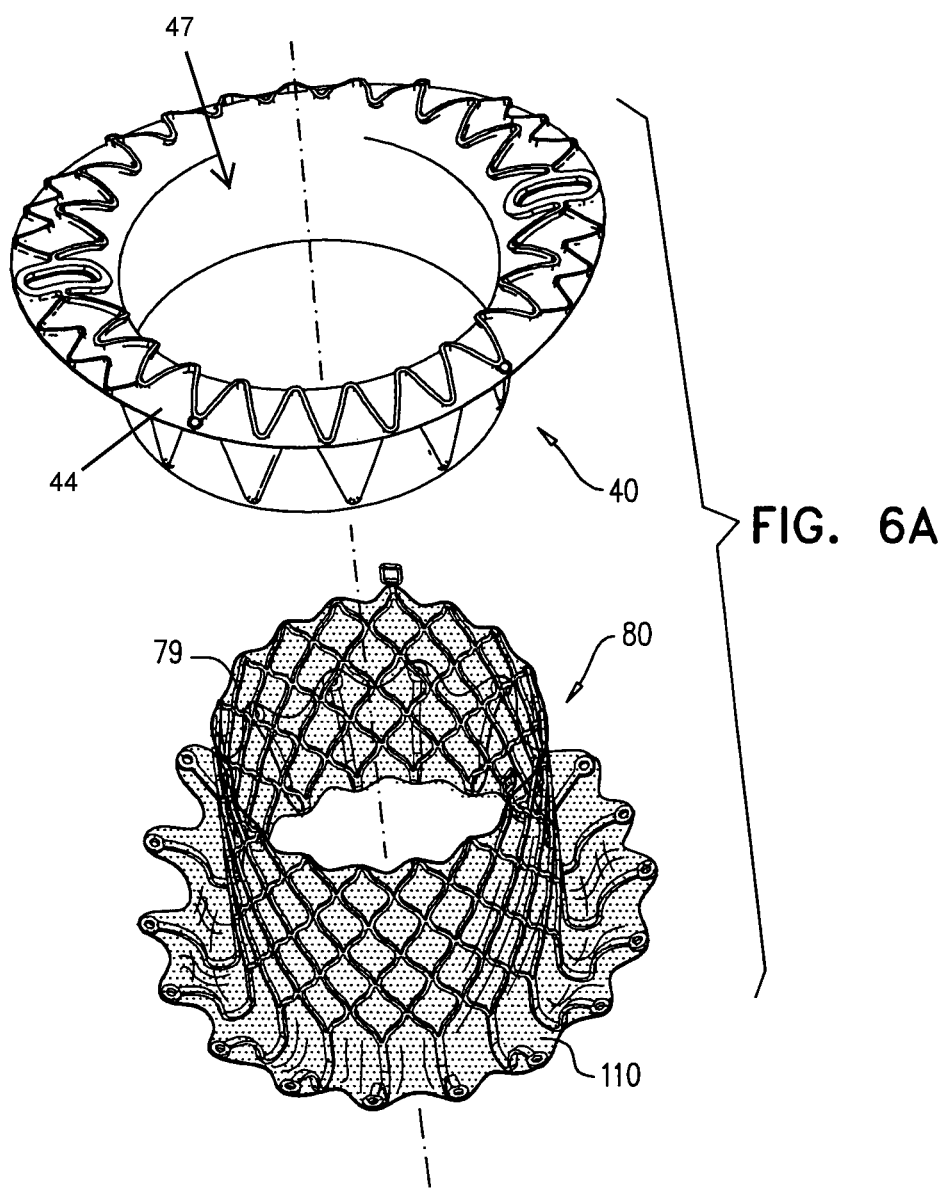
FIGS. 6A-B are schematic illustrations of a prosthetic valve that includes a sealing material, in accordance with some embodiments of the present disclosure.
Figure 6B:
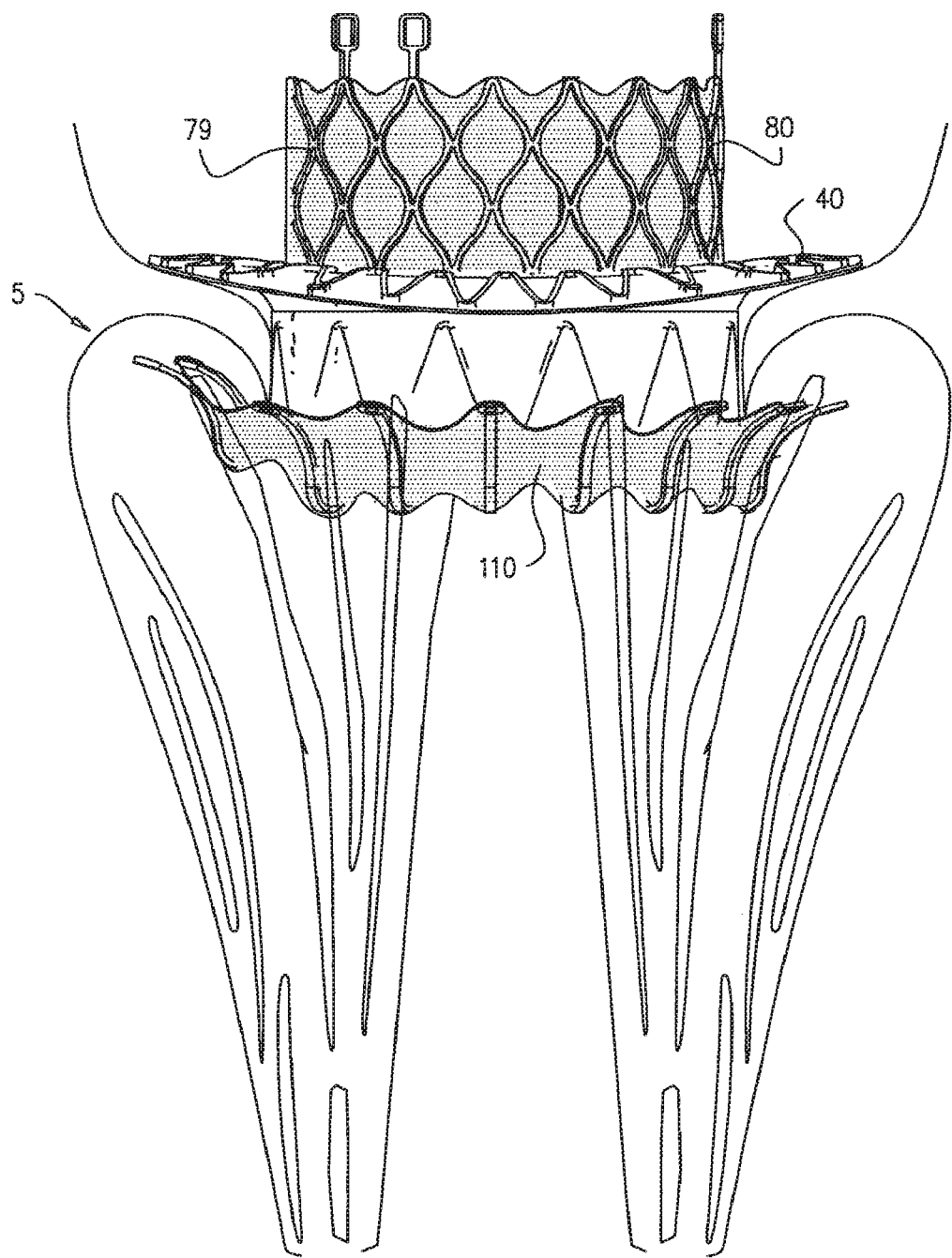

Reference is now made to FIGS. 6A-B, which are schematic illustrations of central valve section 80, the central valve section including a sealing material 110 on an outer surface of the central valve section, in accordance with some embodiments of the present disclosure. For some embodiments, central valve section 80 is used in conjunction with spacer 40, as described hereinabove. The techniques for implanting central valve section 80 as shown in FIGS. 6A-B are generally similar to those described hereinabove. In some embodiments, sealing material 110 seals the interface between the central valve section and native valve 5. The sealing material reduces retrograde blood flow from ventricle 6 into atrium 4, relative to retrograde blood flow in the absence of the sealing material. In some embodiments, the sealing material is composed of latex, dacron, and/or any other suitable biocompatible material. The sealing material is in some embodiments placed around at least a portion of expandable frame 79 of the central valve section so as to form a webbing between struts 79a of the expandable frame.

Reference is now made to FIGS. 7A-F, which are schematic illustrations of a guide wire delivery system, in accordance with some embodiments of the present disclosure. As described hereinabove (e.g., with reference to FIGS. 2C-F), for some embodiments, guide members 21a and 21b, function as spacer guide members, by spacer 40 being slid along guide members 21a and 21b. For some embodiments, only one guide member 21 is looped through commissures 8 and 10 in a manner in which the guide member defines a looped portion between commissures 8 and 10 (i.e., a portion of the guide member that is disposed in a ventricle 6 of heart 2), and first and second free ends, which are disposed and accessible at a site outside the body of the patient. For such embodiments, the guide member defines portions 21a and 21b.

For some embodiments, an anchor base 302 is advanced toward the vicinity of apex 304 of heart 2, via sheath 25, and is anchored to the vicinity of the apex, as shown in FIG. 7A. A guidewire 306 extends proximally from the anchor base 302. Guide member 21 passes through a guide member tube 320, the guide member tube being coupled to guidewire 306.

Guide member 21 is pushed distally. Guide member tube 320 is unable to advance distally over guidewire 306, due to the coupling of the guide member tube to the guidewire. Therefore, the pushing of guide member 21 distally, causes portions 21a and 21b to spread apart from one another and to be pushed against commissures 8 and 10 of native valve 5. Portions 21a and 21b are then used to guide spacer 40 to the commissures, as shown in FIGS. 7B-C, using generally similar techniques to those described hereinabove, except for the differences described hereinbelow.

Figure 7C:
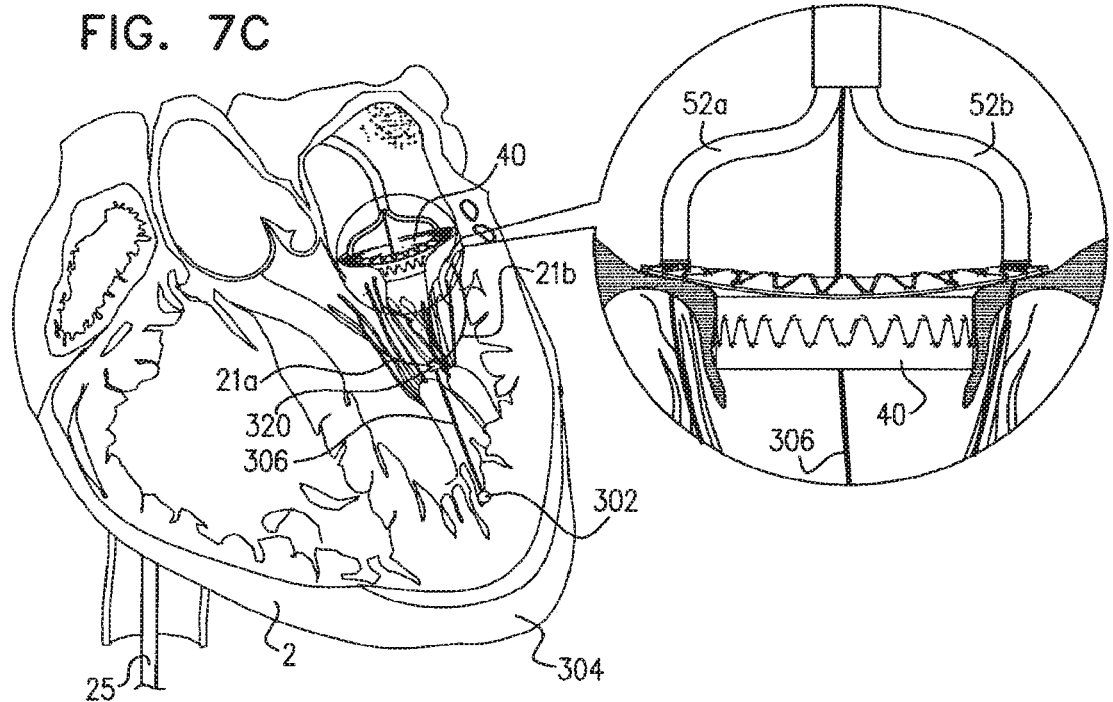

As shown in FIG. 7B, spacer 40 is slid over guide member portions 21a and 21b, by pushing elements 52a and 52b. Since the guide member portions are positioned at commissures 8 and 10, the guide member portions guide the distal ends of pushing elements 52a and 52b, such that the pushing elements push the spacer against the commissures, as shown in FIG. 7C.

Figure 7D:
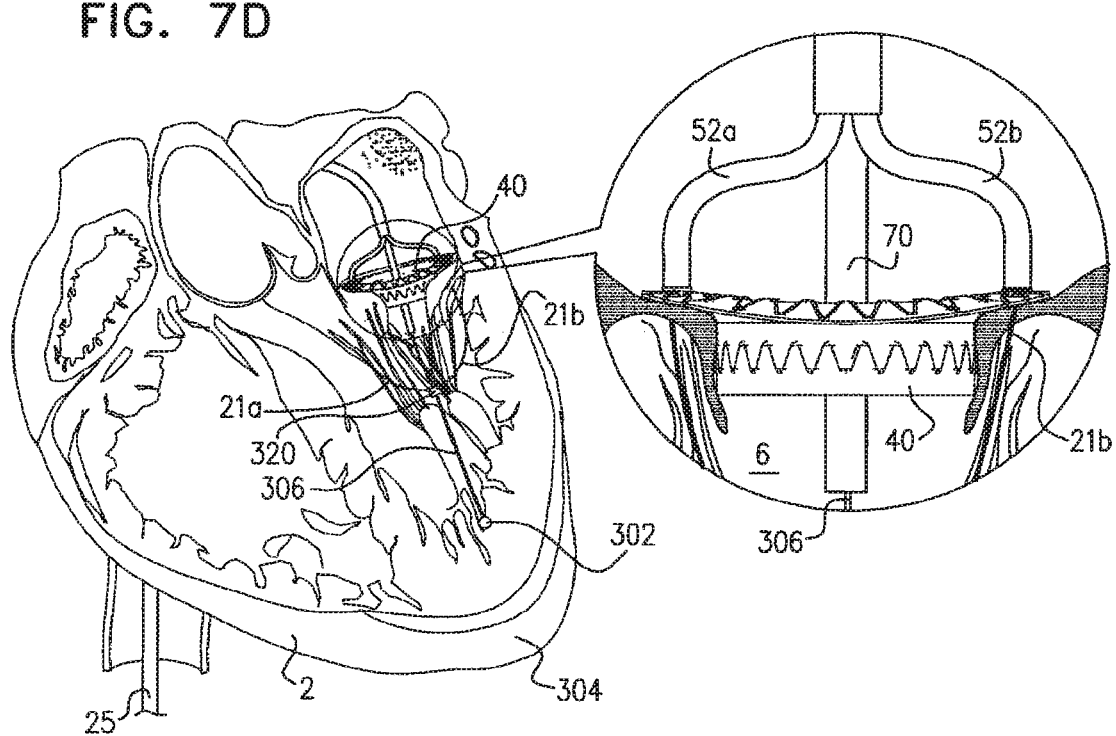
Figure 7E:
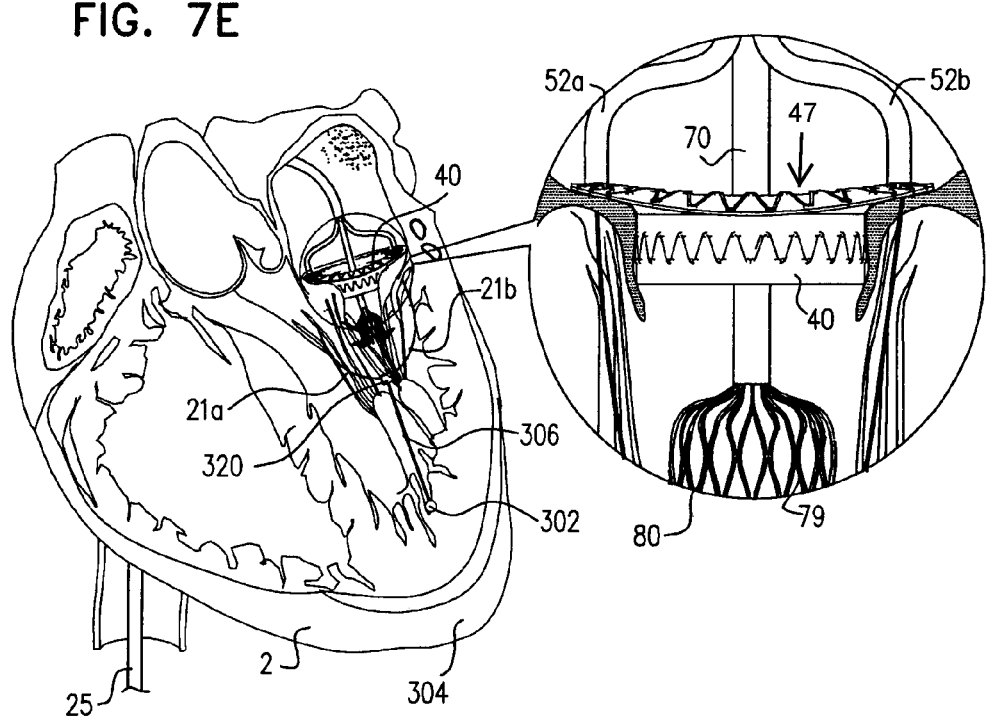

Subsequent to the placement of spacer 40 at the native valve, central valve section 80 is coupled to spacer 40. For some embodiments, pushing elements 52a and 52b continue to push the spacer against the native valve, during the coupling of the central valve section to the spacer. As described hereinabove, overtube 70 is advanced into ventricle 6, as shown in FIG. 7D. FIG. 7E shows central valve section having been partially deployed in the ventricle. Following the partial deployment of central valve section 80 in ventricle 6, overtube 70 is pulled proximally to pull central valve section 80 proximally such that cylindrical skirt 42 and/or disc-shaped wall 44 of spacer 40 surrounds a proximal portion of central valve section 80. Central valve section 80 may be configured to expand such that central valve section 80 is held in place with respect to spacer 40 responsively to radial forces acted upon spacer 40 by central valve section 80. During the pulling back of overtube 70, pushing elements 52a and 52b push spacer 40 against the central valve section, thereby providing a counter force against which overtube 70 is pulled back. For some embodiments, the pushing of the spacer against the commissures is such that it is not necessary to use anchors for anchoring the spacer to the native valve during the coupling of the central valve section to the spacer. Alternatively, in addition to the pushing elements providing a counter force against which the central valve section is pulled, anchors are used to anchor the spacer to the native valve during the coupling of the central valve section to the spacer.

As described hereinabove, central valve section 80 includes a plurality of distal protrusions 84. When central valve section 80 is pulled proximally, as described hereinabove, protrusions 84 ensnare and engage the native leaflets of the atrioventricular valve. By the ensnaring of the native leaflets, protrusions 84 sandwich the native valve between protrusions 84 and spacer 40. Such ensnaring helps further anchor central valve section 80 to the native atrioventricular valve.

For some embodiments, as described hereinabove, protrusions 84 are such as to (a) prevent proximal migration of the central valve section into the patient's atrium, while (b) allowing movement of the native leaflets with respect to the frame of the central valve section. For example, the protrusions may have the aforementioned functionalities by having lengths of less than 5 mm and/or by a total width of each set of protrusions corresponding to respective leaflets of the native valve being less than 5 mm. For example, the central valve section may include a single protrusion corresponding to each leaflet of the native valve, the width of each of the single protrusions being less than 1 mm. Thus, the central valve section may be stopped from proximally migrating into the atrium, by the protrusions preventing the distal end of the central valve section from migrating further proximally than edges of native leaflets of the valve. Furthermore, the protrusions may allow movement of the native leaflets with respect to the frame of the central valve section by not generally squeezing the native leaflets between the protrusions and the frame of the central valve section. For some embodiments, by allowing movement of the native leaflets with respect to the frame of the central valve section, sealing of the native leaflets against the outer surface of the frame of the central valve section is facilitated, in accordance with the techniques described hereinbelow with reference to FIG. 10.

Figure 7F:
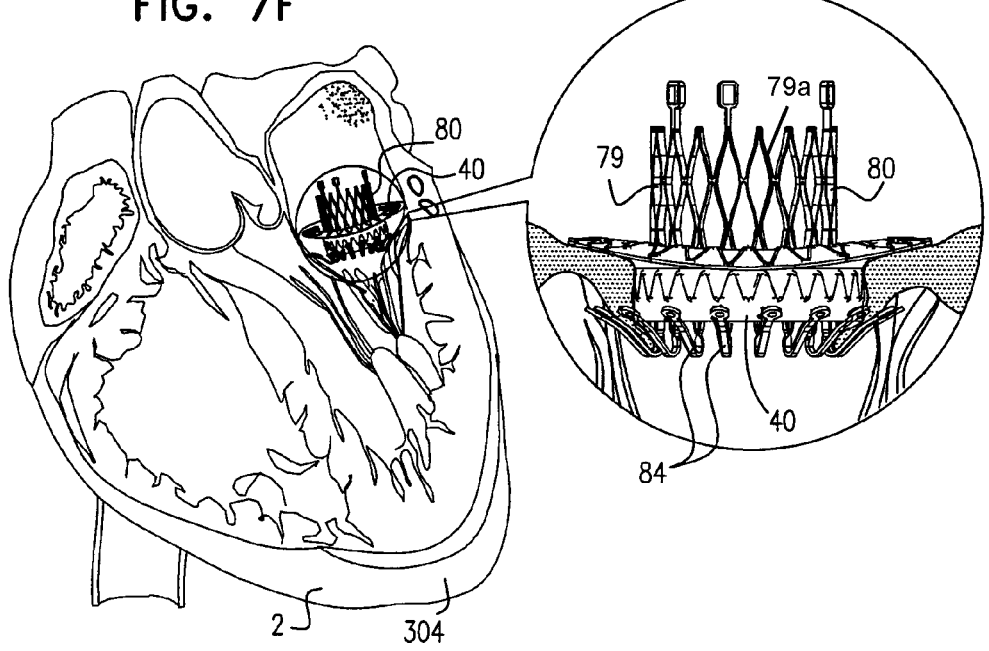

Subsequent to the placement of the central valve section at the native valve, sheath 25, overtube 70, pushing elements 52a and 52b, guide member 21, anchor base 302, and guidewire 306 are removed from the patient's body, as shown in FIG. 7F, which shows the central valve section in its deployed state. For some embodiments, in order to remove guide member 21 from the patient's body, guide member portions 21a and 21b are decoupled from guide member tube 320. For example, the guide member portions may be coupled to the guide member tube via threading, the guide member portions being decoupled from the guide member tube by unscrewing the guide member portions from the guide member tube.

Figure 8A:
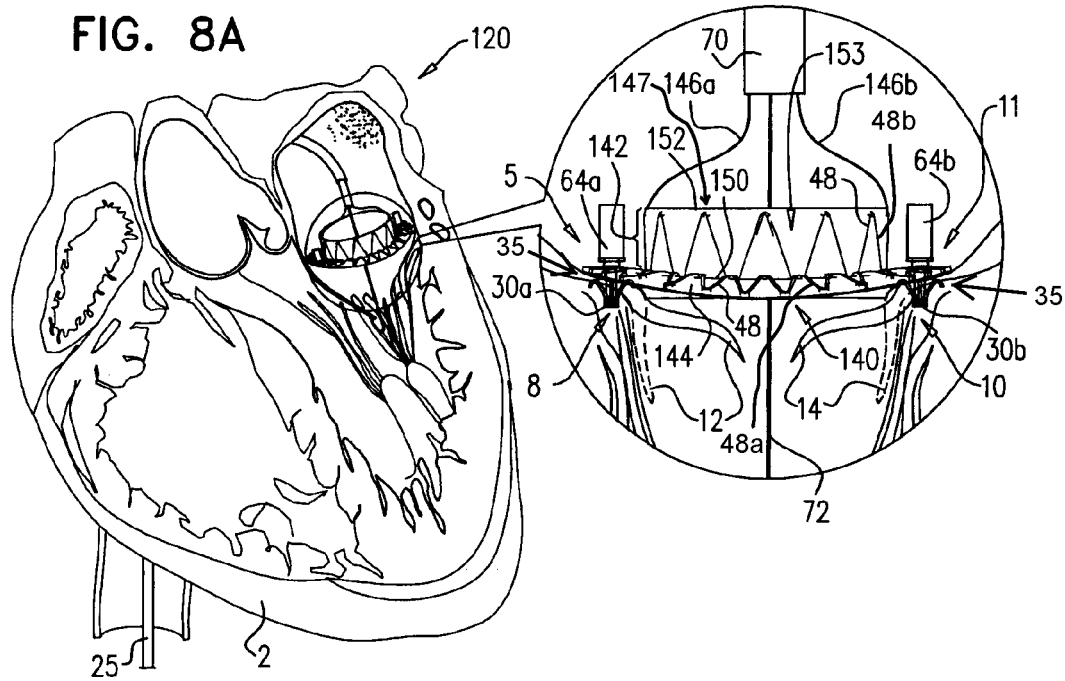
FIGS. 8A-C are schematic illustrations of a valve support that has a cylindrical element that is invertible, in accordance with some embodiments of the present disclosure.
Figure 8B:
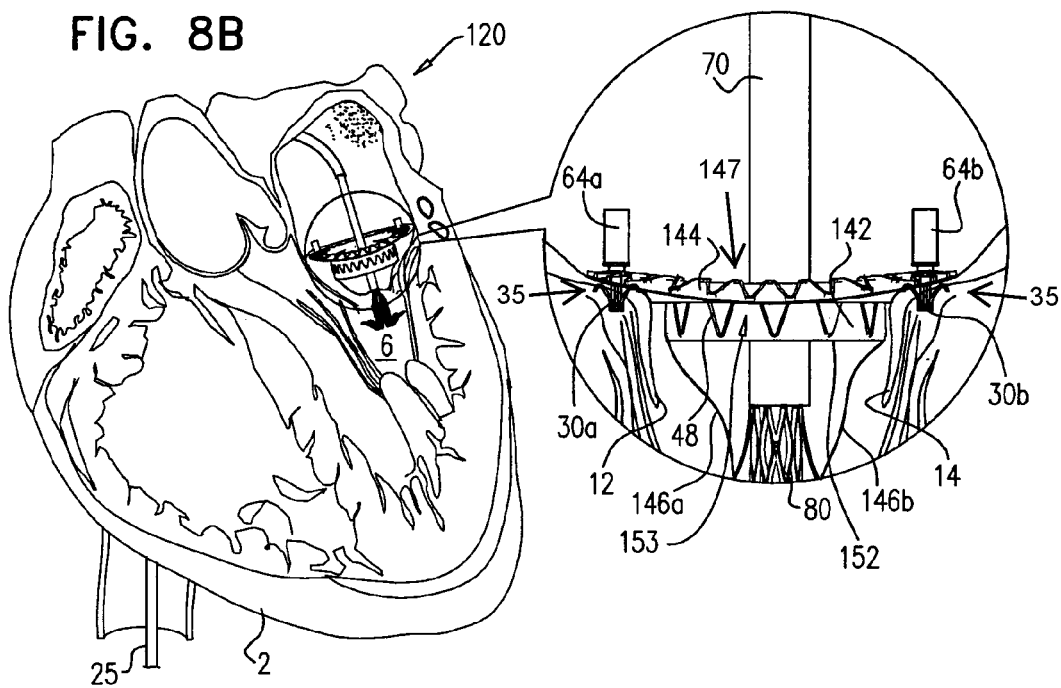
Figure 8C:
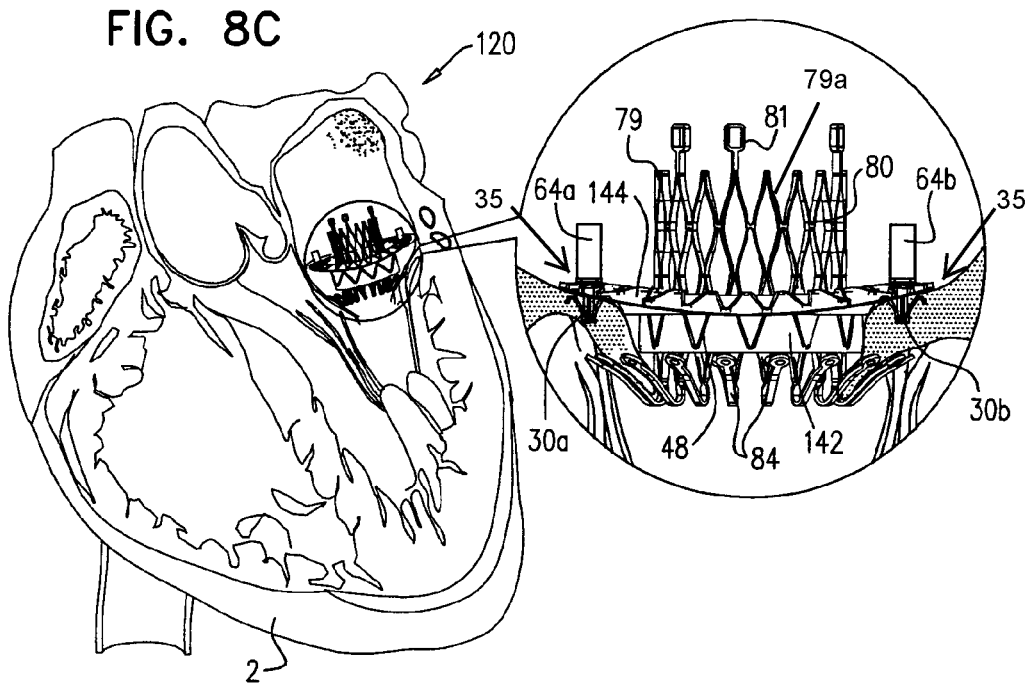

Reference is now made to FIGS. 8A-C which are schematic illustrations of a system 120 including an invertible spacer 140, in accordance with some embodiments of the present disclosure. Invertible spacer 140 is identical to spacer 40 described herein, with the exception that the cylindrical skirt 142 of the spacer 140 is invertible, as is described hereinbelow. Additionally, the method of advancing toward and implanting spacer 140 at annulus 11 is identical to the methods of advancing toward and implanting spacer 40 at annulus 11, as described hereinabove.

Spacer 140 includes a disc-shaped wall 144 (that is identical to disc-shaped wall 44 described hereinabove) and a cylindrical skirt 142. Cylindrical skirt 142 has a first end 150, a second end 152, and a cylindrical body 153 disposed between first and second ends 150 and 152. Cylindrical skirt 142 is attached to disc-shaped wall 144 at first end 150 of cylindrical skirt 142.

During and following implantation of spacer 140 at annulus 11, as shown in FIG. 8A, cylindrical skirt 142 is disposed above disc-shaped wall 144 in a manner in which second end 152 and cylindrical body 153 are disposed above disc-shaped wall 144 and within atrium 4. One or more elongate guide members 146a and 146b are reversibly coupled to cylindrical skirt 142 in a vicinity of second end 152. Elongate guide members 146a and 146b facilitate (a) advancement of central valve section 80 therealong and toward spacer 140, and (b) inversion of cylindrical skirt 142 toward ventricle 6 when at least a portion of central valve section 80 is deployed within ventricle 6 (as shown in FIG. 8B).

The configuration of spacer 140 as shown in FIG. 8A (i.e., the configuration in which cylindrical skirt 142 is disposed within atrium 4) eliminates the obstruction of native valve 5 and of leaflets 12 and 14 by any portion of spacer 140. In this manner, spacer 140 may be implanted at valve 5 while valve 5 resumes its native function and leaflets 12 and 14 resume their natural function (as shown by the phantom drawing of leaflets 12 and 14 in FIG. 8A which indicates their movement). This atrially inverted configuration of spacer 140 reduces and even eliminates the amount of time the patient is under cardiopulmonary bypass. Only once central valve section 80 is delivered and coupled to spacer 140 and cylindrical skirt 142 is thereby ventricularly-inverted, native leaflets 12 and 14 are pushed aside (FIG. 8B).

FIG. 8B shows the inversion of cylindrical skirt 142 by the partial positioning and deployment of central valve section 80 within ventricle 6. Elongate guide members 146a and 146b are reversibly coupled to central valve section 80 and extend within overtube 70. Following the full deployment of central valve section 80 and the coupling of central valve section 80 to spacer 140, elongate guide members 146a and 146b are decoupled from central valve section 80 and from cylindrical skirt 142. For example, a cutting tool may be used to decouple elongate members 146a and 146b from the spacer 140. Alternatively, elongate members 146a and 146b may be looped through the cylindrical skirt 142, such that both ends of each elongate member 146a and 146b remain outside of the patient's body. The operating physician decouples elongate members 146a and 146b from spacer 140 by releasing one end of each of elongate members 146a and 146b and pulling on the other end, until elongate members 146a and 146b are drawn from spacer 140 and removed from within the body of the patient.

FIG. 8O shows central valve section 80 coupled to spacer 140. Central valve section 80 is identical to the central valve section described hereinabove.

Reference is now made to FIGS. 9A-E, which are schematic illustrations of the advancement of an invertible spacer 300 toward a native atrioventricular valve of a patient, and inversion of the spacer, in accordance with some embodiments of the present disclosure. Spacer 300 is used to anchor central valve section 80 to native valve 5 in a generally similar manner to that described with reference to spacer 40.

Figure 9A:
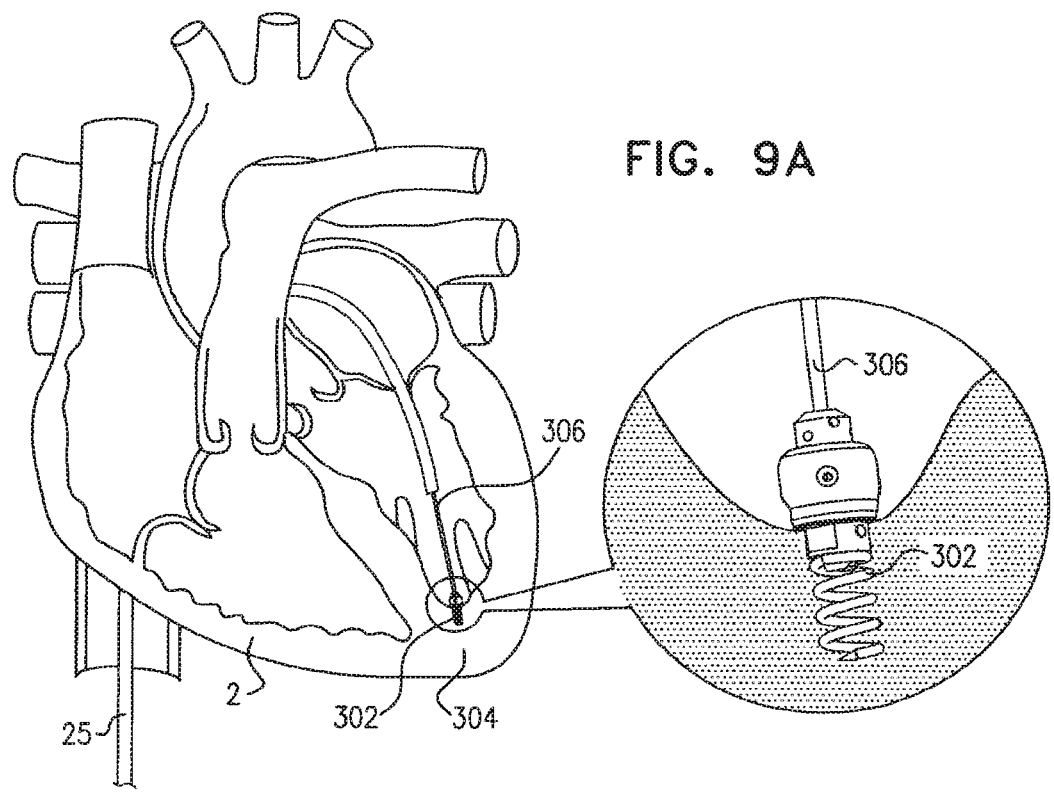
FIGS. 9A-D are schematic illustrations of the advancement of an invertible prosthetic valve support toward a native atrioventricular valve of a patient, in accordance with some embodiments of the present disclosure.
Figure 9B:
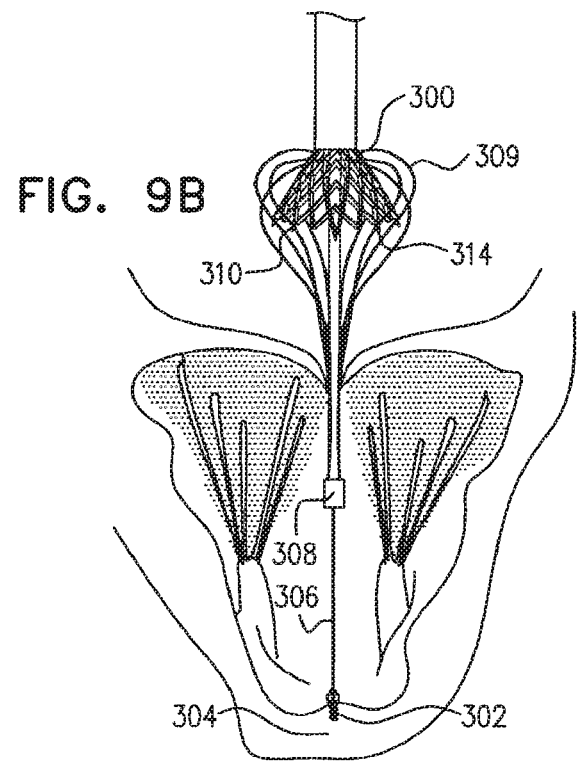
Figure 9C:
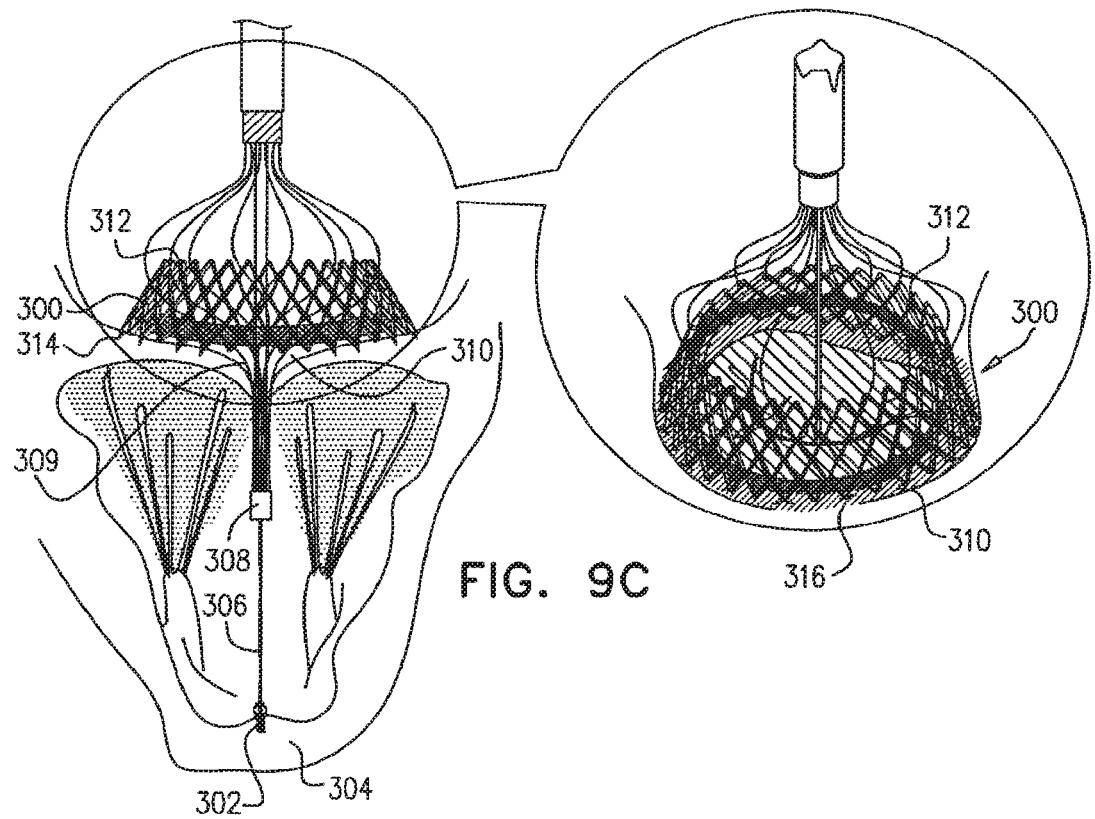
Figure 9D:
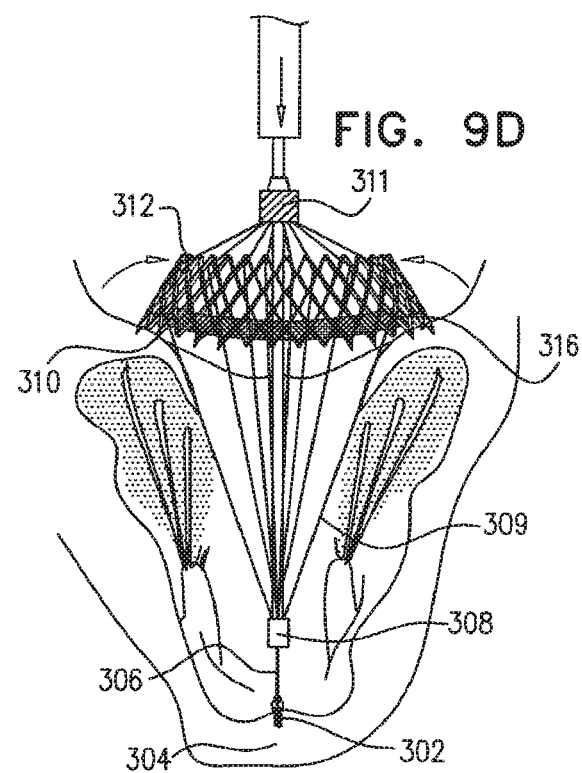
Figure 9E:
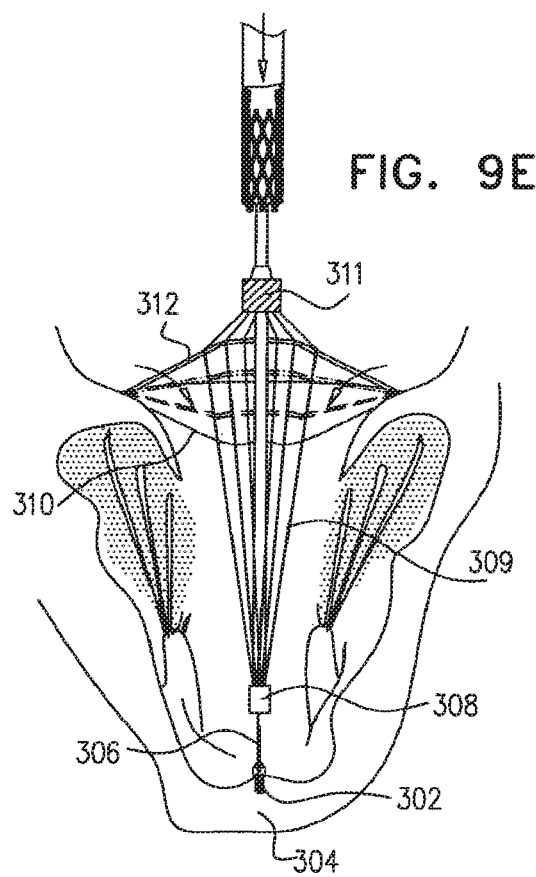
FIG. 9E is a schematic illustration of inversion of the invertible prosthetic valve support at the native valve, in accordance with some embodiments of the present disclosure.

During an exemplary procedure, anchor base 302 is advanced toward the vicinity of apex 304 of heart 2, via sheath 25, and is anchored to the vicinity of the apex, as shown in FIG. 8A. A guidewire 306 extends proximally from the anchor base. A distal tensioning element 308 (e.g., a plunger) is advanced over guidewire 306 into ventricle 6, and spacer 300 is advanced out of the distal end of sheath 25, as shown in FIG. 9B. A first end 310 of spacer 300 (which at this stage is the distal end of the spacer), includes barbs 314 (shown in FIG. 9B), or other anchoring elements for anchoring the first end of the spacer to tissue of native valve 5. Spacer 300 is pushed distally such that the barbs are pushed into the native valve tissue, thereby anchoring the first end of the spacer to the native valve, as shown in FIG. 9C. A plurality of wires 309 pass from distal tensioning element 308 to a proximal tensioning element 311 (shown in FIG. 9D), via a second end 312 of spacer 300 (which at this stage is the proximal end of the spacer). For some embodiments, a sealing element 316 is disposed circumferentially around a surface of the invertible spacer that is initially an inner surface of the invertible spacer (a shown in FIGS. 8A-D). For example, the sealing material may be latex, dacron, or another suitable biocompatible sealing material.

Figure 9F:
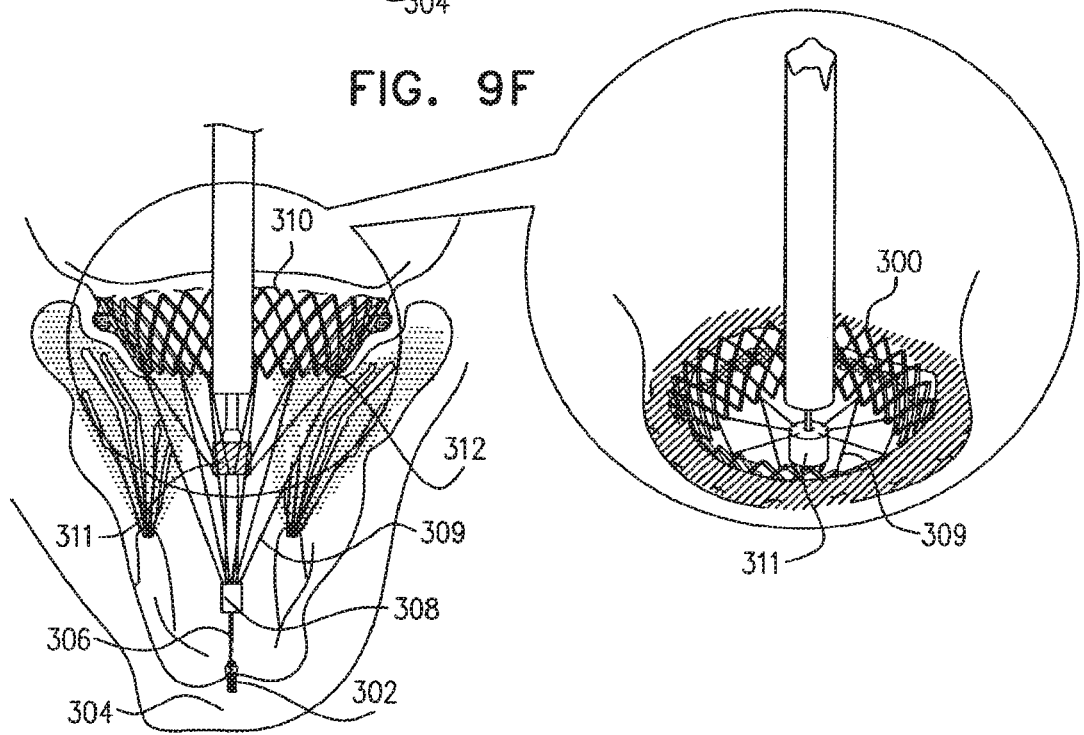
FIGS. 9F-H are schematic illustrations of the advancement of a prosthetic valve and the coupling of the prosthetic valve to the invertible valve support, in accordance with some embodiments of the present disclosure.

Subsequent to the anchoring of first end 310 of spacer 300 to native valve tissue (as shown in FIG. 9O), distal tensioning element 308 is further advanced distally into ventricle 6, and proximal tensioning element 311 is advanced toward the ventricle. As shown in the transition from FIG. 9D-F, as the proximal tensioning element passes through the spacer, wires 309 cause spacer 300 to invert, by pulling second end 312 of the spacer through first end 310 of the spacer. Subsequent to the inversion of the spacer, sealing material 316 is disposed circumferentially around the outside of the spacer, thereby providing a seal at the interface between spacer 300 and native valve 5.

Figure 9G:
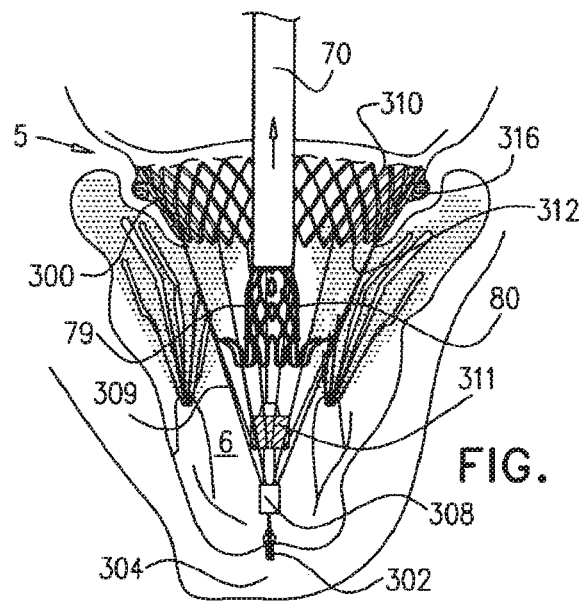
Figure 9H:
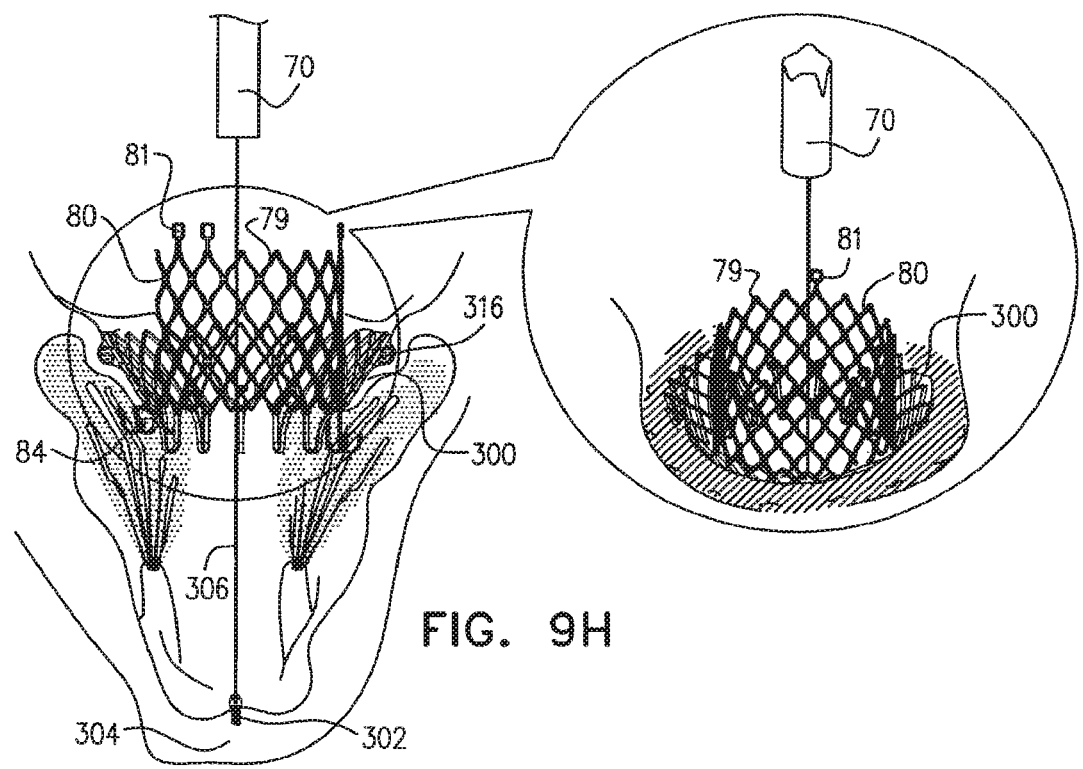

Reference is now made to FIGS. 9G-H, which are schematic illustrations of the deployment of central valve section 80 and the coupling of the central valve section to invertible spacer 300, in accordance with some embodiments of the present disclosure.

The deployment of central valve section 80 is generally similar to the techniques described hereinabove with reference to FIGS. 2H-J. The central valve section is partially deployed in ventricle 6, via overtube 70. Following the partial deployment of central valve section 80 in ventricle 6, overtube 70 is pulled proximally (as shown in FIG. 8G) to pull central valve section 80 proximally such that spacer 300 surrounds a proximal portion of central valve section 80, as shown in FIG. 8H. Central valve section 80 may be configured to expand such that central valve section 80 is held in place with respect to spacer 300 responsively to radial forces acted upon spacer 300 by central valve section 80.

As described hereinabove, for some embodiments, central valve section 80 includes a plurality of distal protrusions 84. When central valve section 80 is pulled proximally, protrusions 84 ensnare and engage the native leaflets of the atrioventricular valve. By the ensnaring of the native leaflets, protrusions 84 sandwich the native valve between protrusions 84 and spacer 300. Such ensnaring helps further anchor central valve section 80 to the native atrioventricular valve.

For some embodiments, as described hereinabove, protrusions 84 are such as to (a) prevent proximal migration of the central valve section into the patient's atrium, while (b) allowing movement of the native leaflets with respect to the frame of the central valve section. For example, the protrusions may have the aforementioned functionalities by having lengths of less than 5 mm, and/or by a total width of each set of protrusions corresponding to respective leaflets of the native valve being less than 5 mm. For example, the central valve section may include a single protrusion corresponding to each leaflet of the native valve, the width of each of the single protrusions being less than 1 mm. Thus, the central valve section may be stopped from proximally migrating into the atrium, by the protrusions preventing the distal end of the central valve section from migrating further proximally than edges of native leaflets of the valve. Furthermore, the protrusions may allow movement of the native leaflets with respect to the frame of the central valve section by not generally squeezing the native leaflets between the protrusions and the frame of the central valve section. For some embodiments, by allowing movement of the native leaflets with respect to the frame of the central valve section, sealing of the native leaflets against the outer surface of the frame of the central valve section is facilitated, in accordance with the techniques described hereinbelow h reference to FIG. 10.

Additionally, as shown in FIG. 9H, and as described hereinabove, central valve section 80 includes one or more coupling elements 81 (for example, a plurality of coupling elements, as shown) at the proximal end of central valve section 80. Overtube 70, which facilitates the advancement of central valve section 80, is reversibly coupled to central valve section 80, via coupling elements 81.

Subsequent to the coupling of central valve section 80 to spacer 300, overtube 70, distal and proximal tensioning elements 308 and 311, and wires 309 are removed from the patient's body, via sheath 25. In some embodiments, wires 309 are cut, in order to facilitate the removal of the wires from the patient's body. Guidewire 306 and anchor base 302 are removed from the patient's body by detaching the anchor base from apex 304, and withdrawing the anchor base and the guidewire, via sheath 25.

Reference is now made to FIG. 10, which is a schematic illustration of central valve section 80, for placing inside atrioventricular valve 5 of the patient, in accordance with some embodiments of the present disclosure. The expandable frame 79 of the central valve section has a diameter d, and a corresponding cross-sectional area. Native annulus 11, which is in some embodiments saddle-shaped, defines an area A, as shown. For some embodiments, area A, which is defined by the native annulus is measured, e.g., using a measuring ring. A central valve section is chosen to be placed in the annulus, the cross-sectional area of the central valve section being less than 90% (e.g., less than 80%, or less than 60%) of area A. For some embodiments, diameter d of the central valve section is less than 25 mm, e.g., less than 20 mm, and/or more than 15 mm, e.g., 15-25 mm. For some embodiments, placing a central valve section inside the native valve with the dimensions of the native valve annulus and the central valve section as described, facilitates sealing of the central valve section with respect to the native valve, by the native valve leaflets closing around the outer surface of the central valve section.

For some embodiments, a spacer 40 that includes disc-shaped wall 44 (e.g., as shown in FIGS. 14A-C) is chosen to be placed at the annulus, the disc-shaped wall defining an inner cross-sectional area that is less than 90% (e.g., less than 80%, or less than 60%) of area A. Central valve section 80 is deployed at the native valve by coupling the central valve section to the spacer at the location, responsively to radial forces acted upon the spacer by the expandable frame, by facilitating expansion of the expandable frame, as described herein. The cross-sectional area defined by the expandable frame of the central valve section, upon expansion of the expandable frame, is limited by the cross-sectional area defined by the disc-shaped wall of the spacer to less than 90% (e.g., less than 80%, or less than 60%) of area A. For some embodiments, placing a spacer at the annulus with the dimensions of the native valve annulus and spacer 40, as described, facilitates sealing of the central valve section with respect to the native valve, by the native valve leaflets closing around the outer surface of the central valve section.

In some embodiments, placing a central valve section inside the native valve with the dimensions of the native valve annulus, the central valve section 80, and/or spacer 40 as described in the above paragraphs, facilitates sealing of the central valve section with respect to the native valve. For some embodiments, the sealing is facilitated by the native leaflets being pushed against, and closing against, the outer surface of the frame of the central valve section during systole, in a similar manner to the manner in which native valve leaflets coapt during systole, in a healthy mitral valve. In some embodiments, as the diameter of the central valve section is increased, the length of the native leaflets that is pushed against the outer surface of the central valve section during systole is increased, thereby enhancing the sealing of the native leaflets with respect to the frame of the central valve section. However, beyond a given diameter, as the diameter of the central valve section is increased, the native valve leaflets are pushed apart at the commissures, thereby causing retrograde leakage of blood through the commissures. Therefore, in accordance with some embodiments of the present disclosure, central valve section 80, and/or spacer 40 are chosen such that the cross-sectional area of the central valve section when expanded inside the spacer is less than 90% (e.g., less than 80%, or less than 60%) of area A. Thus the spacer facilitates sealing of the central valve section with respect to the native valve, by the native valve leaflets closing around the outer surface of the central valve section, while not causing retrograde leakage of blood through the commissures.

For some embodiments, in order to facilitate the sealing of the native valve around the outer surface of the central valve section, a material is placed on the outer surface of the central valve section in order to provide a sealing interface between the central valve section and the native valve. For example, a smooth material that prevents tissue growth (e.g., polytetrafluoroethylene (PTFE), and/or pericardium) may be placed on the outer surface of the central valve section. Alternatively or additionally, a material that facilitates tissue growth (such as dacron) may be placed on the outer surface of the central valve section, in order to (a) act as a sealing interface between the native valve and the central valve section, and (b) facilitate tissue growth around the central valve section to facilitate anchoring and/or sealing of the central valve section.

Reference is now made to FIGS. 11A-D, which are schematic illustrations of central valve section 80, in accordance with some embodiments of the present disclosure. For some embodiments, protrusions 84 are disposed on the central valve section on portions 400 of the central valve section that are placed adjacent to the anterior and posterior leaflets of the native valve, and the central valve section does not include protrusions on portions 402 of the central valve section that are placed adjacent to the commissures of the native valve.

Figure 11D:
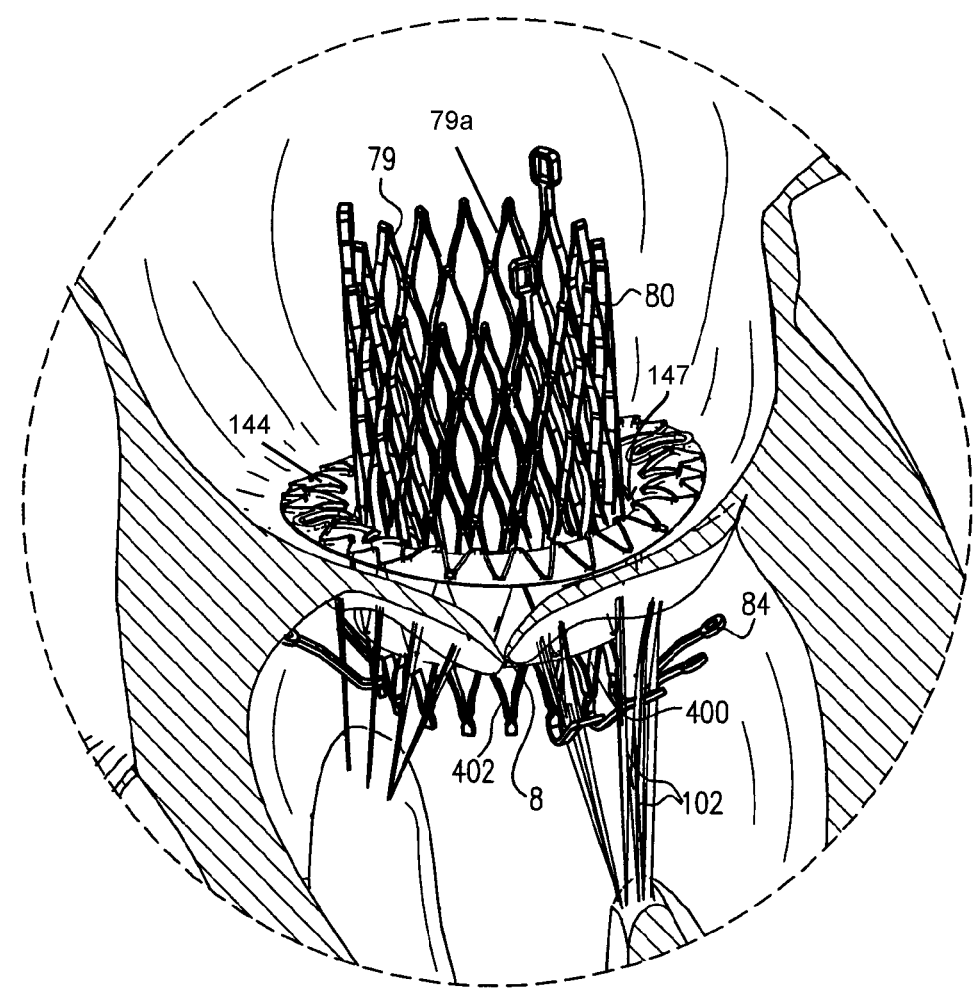

FIGS. 11B-D show bottom views (i.e., views of the distal ends) of respective configurations of central valve section 80 and protrusions 84. The protrusions converge from the proximal ends 404 of the protrusion to the distal ends 406 of the protrusions. The protrusions are configured such as to ensnare chordae tendineae, and to pull the chordae tendineae toward each other when the central valve section is pulled proximally, due to the convergence of the snares with respect to each other. FIG. 11D shows the central valve section deployed at native valve 5. As shown, the protrusions ensnare chordae tendineae 102 of the patient. The protrusions facilitate sealing and anchoring of the central valve section with respect to the native valve by pulling the chordae tendinae toward each other, as described. As described hereinabove, for some embodiments the central valve section does not define protrusions 84 on portions 402 that are placed next to the native commissures, e.g., commissure 8, shown in FIG. 11D.

For some embodiments, as described hereinabove, protrusions 84 are such as to (a) prevent proximal migration of the central valve section into the patient's atrium, while (b) allowing movement of the native leaflets with respect to the frame of the central valve section. For example, the protrusions may have the aforementioned functionalities by having lengths of less than 5 mm, and/or by a total width of each set of protrusions corresponding to respective leaflets of the native valve being less than 5 mm. For example, the central valve section may include a single protrusion corresponding to each leaflet of the native valve, the width of each of the single protrusions being less than 1 mm. Thus, the central valve section may be stopped from proximally migrating into the atrium, by the protrusions preventing the distal end of the central valve section from migrating further proximally than edges of native leaflets of the valve. Furthermore, the protrusions may allow movement of the native leaflets with respect to the frame of the central valve section by not generally squeezing the native leaflets between the protrusions and the frame of the central valve section. For some embodiments, by allowing movement of the native leaflets with respect to the frame of the central valve section, sealing of the native leaflets against the outer surface of the frame of the central valve section is facilitated, in accordance with the techniques described hereinabove with reference to FIG. 10.

For some embodiments, a first set of protrusions 84 from the distal end of central valve section 80 are disposed within a first circumferential arc with respect to a longitudinal axis of the central valve section, on a first side of the distal end of the central valve section, the first side of the distal end being configured to be placed adjacent to the anterior leaflet of the native valve. A second set of protrusions are disposed within a second circumferential arc with respect to a longitudinal axis of the central valve section, on a second side of the distal end of the central valve section, the second side of the distal end being configured to be placed adjacent to the posterior leaflet of the native valve.

The first and second sets of protrusions are disposed so as to provide first and second gaps therebetween at the distal end of the central valve section. In some embodiments, at least one of the gaps between the two sets of protrusions has a circumferential arc of at least 20 degrees (e.g., at least 60 degrees, or at least 100 degrees), and/or less than 180 degrees (e.g., less than 140 degrees), e.g., 60-180 degrees, or 100-140 degrees. Further in some embodiments, one or both of the first and second circumferential arcs defines an angle of at least 25 degrees (e.g., at least 45 degrees), and/or less than 90 degrees (e.g., less than 75 degrees), e.g., 25-90 degrees, or 45-75 degrees.

Valve section guide members (e.g., guide members 21a and 21b, and/or delivery lumen 27a and 27b, as described hereinabove) are delivered to commissures of the native valve, and guide the central valve section such that the first and second circumferential arc are aligned with respective leaflets of the native valve and such that the first and second gaps are aligned with respective commissures of the native valve.

Reference is now made to FIGS. 12A-C, which are schematic illustrations of central valve section 80, the central valve section defining distal protrusions 84 that are disposed sinusoidally around the circumference of the central valve section, in accordance with some embodiments of the present disclosure. For some embodiments the protrusions are shaped sinusoidally, in order to conform with the saddle-shape of native valve annulus 11, thereby facilitating the sandwiching of the native valve leaflets between the protrusions and spacer 40. As shown, the peaks of the sinusoid that is defined by the protrusions is disposed on portions 402 that are placed next to the native commissures and the troughs of the sinusoid is placed on portions of the central valve section that are placed in the vicinity of the centers of the anterior and posterior leaflets of the native valve. As shown in FIG. 12C, for some embodiments the distal end of the central valve section defines a sinusoidal shape.

Figure 13A:
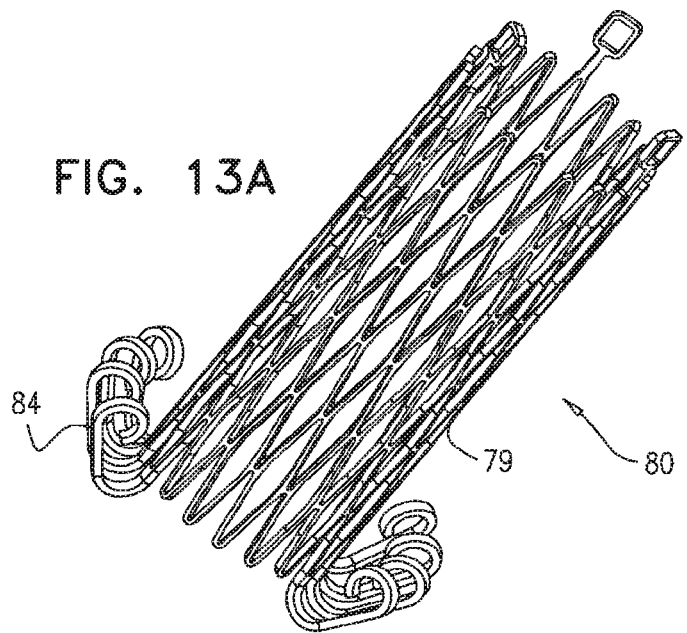
Figure 13B:
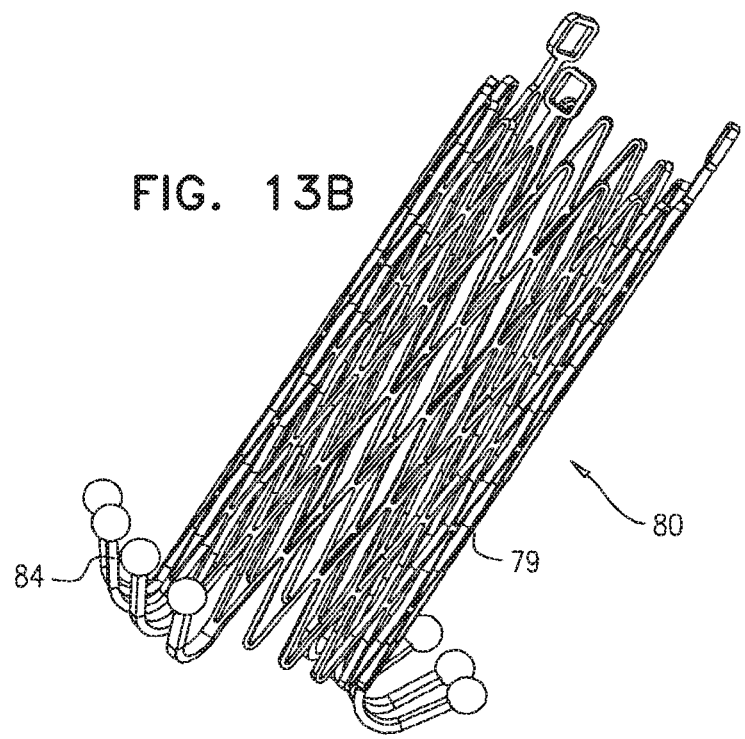

Reference is now made to FIGS. 13A-E, which are schematic illustrations of respective configurations of expandable frame 79 of central valve section 80, in accordance with some embodiments of the present disclosure. As described hereinabove, for some embodiments, central valve section 80 defines distal protrusions 84 that are configured to facilitate sandwiching of the native valve leaflets between the protrusions and spacer 40. For some embodiments, tips of the distal protrusions are shaped so as to prevent the tips from piercing, and/or otherwise damaging, tissue of the native leaflets. For example, the tips of the protrusions may be curved, as shown in FIG. 13A. Or, the distal tips of the protrusions may be shaped as balls, as shown in FIG. 13, and/or a different rounded shape. For some embodiments, the distal tip of each of the protrusions is joined to the distal tip of an adjacent protrusion by an arch 410, as shown in FIGS. 130 and 13D.

For some embodiments, the protrusions are configured to be distally-facing during the insertion of central valve section 80 into the subject's left ventricle. For example, the central valve section may be inserted through overtube 70 (shown in FIG. 7E, for example). The central valve section is crimped during the insertion of the central valve section through the overtube, and the protrusions are constrained in their distally-facing configurations by the overtube. The protrusions are preshaped such that in the resting state of the protrusions, the protrusions assume proximally-facing configurations, as shown in FIG. 13D, for example. Thus, upon emerging from overtube 70, the protrusions assume proximally-facing configurations. For some embodiments, when the protrusions assume the proximally-facing configurations, the protrusions are disposed at an angle theta (FIG. 13D) from expandable frame 79 of more than 40 degrees (e.g., more than 50 degrees), and/or less than 80 degrees (e.g., less than 70 degrees).

In some embodiments, protrusions 84 are coupled to frame 79 of central valve section 80 at joints 412. For some embodiments, joints 412 are thinner than portions of the protrusions and of the frame surrounding the joints, as shown in FIG. 13D. For some embodiments, the thinness of the joints with respect to the surrounding portions facilitates the crimping of the protrusions into distally-facing configuration during the insertion of the central valve section into the heart.

For some embodiments, barbs 416 extend from a proximal portion of expandable frame 79 of central valve section 80, as shown in FIG. 13E, For example, the barbs may be configured to anchor the central valve section to the native valve by piercing tissue of the native valve. Alternatively or additionally, the barbs may be configured to anchor the central valve section to the spacer 40, by becoming coupled to portions of the spacer. For some embodiments the barbs protrude from the top-central corner of respective cells of expandable frame 79. In some embodiments, when the central valve section is crimped, the barbs fit within gaps of respective cells of the expandable frame, and do not substantially increase the crimping profile of the central valve section, relative to a generally similar central valve section that does not include barbs.

For some embodiments, the barbs are not generally used for coupling central valve section 80 to spacer 40. Rather, the central valve section is coupled to the spacer by virtue of radial expansion of the central valve section against disc-shaped wall 44 of the spacer. Barbs 416 are used to prevent central valve section from migrating distally into the patient's left ventricle, and/or to prevent spacer 40 from migrating proximally into the subject's left atrium.

For some embodiments (not shown), barbs protrude from coupling elements 81 of central valve section 80, the barbs being generally similar in shape and function to that described with reference to barbs 416. For some embodiments (not shown), radially-inwardly facing barbs 45 protrude from disc-shaped wall 44 of spacer 40, as shown in FIG. 14D. As described with reference to barbs 416, the barbs that protrude from disc-shaped wall 44 may facilitate coupling of the central valve section to the spacer. Alternatively or additionally, the barbs that protrude from disc-shaped wall 44 are used to prevent central valve section from migrating distally into the patient's left ventricle, and/or to prevent spacer 40 from migrating proximally into the subject's left atrium.

For some embodiments, a proximal end of expandable frame 79 of central valve section 80 defines a larger cross-section area than more distal portions of the expandable frame. For example, the expandable frame may have a frustoconical shape, the walls of the expandable frame diverging from a distal end of the frame to a proximal end of the frame. Alternatively, the expandable frame may have a trumpet shape (i.e., the frame may be generally tubular, with a dilated proximal end). For some embodiments, the larger cross-sectional area of the proximal end of the frame prevents the central valve section from migrating distally into the patient's left ventricle, and/or prevents spacer 40 from migrating proximally into the subject's left atrium.

Reference is now made to FIGS. 14A-D, which are schematic illustrations of respective configurations of spacer 40, in accordance with some embodiments of the present disclosure. As described hereinabove, for some embodiments, the spacer includes a proximal disc-shaped wall 44 and a distal cylindrical skirt 42 (e.g., as shown in FIG. 2D). Alternatively, the spacer does not include a distal cylindrical element. For example, the spacer may only include disc-shaped wall 44. As described hereinabove, disc-shaped wall 44 is configured to be placed around native annulus 11 of the native valve, and to extend at least partially into atrium 4 such that disc-shaped wall 44 rests against the native annulus. Disc-shaped wall 44 is in some embodiments too large to pass through the annulus, and may, for example, have an outer diameter of between 30 and 60 mm.

FIGS. 14A-D show disc-shaped wall 44 of spacer 40 in respective configurations, in accordance with some embodiments of the present disclosure. For some embodiments, the disc-shaped wall is D-shaped, as shown in FIG. 14A. Alternatively or additionally, the disc-shaped wall has a generally round shape, as shown in FIGS. 14B-C. For some embodiments the disc-shaped wall is asymmetrical. For example, FIG. 14B shows a generally rounded disc-shaped wall that is wider on a first side 420 of the element than on a second side 422 of the element. In some embodiments, the wider side of the disc-shaped wall is placed on the anterior side of the native annulus. In accordance with some embodiments, the disc-shaped wall is symmetrical, asymmetrical, oval, round, defines a hole that is centered with respect to the disc-shaped wall, and/or defines a hole that is off-center with respect to the disc-shaped wall. For some embodiments, the stiffness of the disc-shaped wall varies around the circumference of the disc-shaped wall.

For some embodiments, disc-shaped wall 44 is asymmetrical, as shown in FIG. 14B. In some embodiments, the asymmetry of the disc-shaped wall is such that the center of the hole defined by the disc-shaped wall is disposed asymmetrically (i.e., off-center) with respect to the center of the disc-shaped wall, as defined by the outer perimeter of the disc-shaped wall. For some embodiments, the asymmetric disposition of the center of the hole defined by the disc-shaped wall is such that when the central valve section is placed inside the disc-shaped wall, the longitudinal axis of the central valve section is disposed asymmetrically (i.e., off-center) with respect to the center of the disc-shaped wall, as defined by the outer perimeter of the disc-shaped wall. In some embodiments, the disc-shaped wall is shaped such that, when the disc-shaped wall is placed on the patient's mitral annulus, and the central valve section is expanded inside the disc-shaped wall, the longitudinal axis of the central valve section is disposed in the vicinity of the location at which the patient's native leaflets coapt (this location being off-center with respect to the patient's native mitral annulus).

For some embodiments (not shown), radially-inwardly facing barbs 45 protrude from disc-shaped wall 44 of spacer 40, as shown in FIG. 14D. As described with reference to barbs 416 shown protruding from central valve section 80 in FIG. 13E, the barbs that protrude from disc-shaped wall 44 may facilitate coupling of the central valve section to the spacer. Alternatively or additionally, the barbs that protrude from disc-shaped wall 44 are used to prevent central valve section from migrating distally into the patient's left ventricle, and/or to prevent spacer 40 from migrating proximally into the subject's left atrium. For some embodiments, some or all of barbs 102 are curved. In some embodiments, the curved barbs curve away from the plane of disc-shaped wall 44, such that, when implanted, barbs 102 point into the patient's atrium.

In some embodiments, the disc-shaped wall includes support stent 48, the stent being covered at least in part with covering 49, e.g., fabric. In some embodiments, the upper surface of disc-shaped wall 44 is covered with fabric, for example, in order to provide a generally smooth surface for coming into contact with the patient's blood flow. Further in some embodiments, the lower surface of the disc-shaped wall (i.e., the side of the disc-shaped wall that is placed in contact with the native annulus) is not covered with fabric, for example, in order to reduce a crimped volume (or cross-sectional area) of the disc-shaped wall, relative to the volume of the disc-shaped wall if the lower surface of the disc-shaped wall were covered in fabric. In some embodiments, a thickness of the fabric layer is less than 0.2 mm, e.g., less than 0.1 mm, or less than 0.05 mm.

For some embodiments, the side of the disc-shaped wall that is placed in contact with the native annulus is covered with the fabric, the fabric being configured to facilitate coupling of the disc-shaped wall to the native annulus, by facilitating fibrosis at the interface between the disc-shaped wall and the native annulus. For some embodiments, the upper surface of the disc-shaped wall is not covered with fabric. For example, the upper surface may not be covered in fabric in order to reduce a crimped volume (or cross-sectional area) of the disc-shaped wall, relative to the volume of the disc-shaped wall if the upper surface of the disc-shaped wall were covered in fabric.

For some embodiments, disc-shaped wall 44 is not covered with fabric, and/or is not configured to form a seal against frame 79 of central valve section 80. For some embodiments, the disc-shaped wall is configured to allow leakage of blood between the disc-shaped wall and frame 79 of central valve section 80. For example, the disc-shaped wall may be configured to allow leakage of blood through the interface between the disc-shaped wall and the frame of the central valve section, in order to accommodate a flow of blood between the patient's atrium and the patient's ventricle that is greater than can be accommodated by blood flowing through the leaflets of the central valve section.

Reference is now made to FIGS. 15A-E, which are schematic illustrations of respective steps of a procedure for deploying a central valve section, in accordance with some embodiments of the present disclosure. As described hereinabove and hereinbelow (for example, with reference to FIGS. 2A-K, 7A-F, 8A-C, 9A-H, and 16A-G), for some procedures, spacer 40 is placed on the valve annulus and, subsequently, central valve section 80 is inserted into the subject's left ventricle through the spacer. Alternatively, any of the procedures described herein (for example, procedures described with reference to FIGS. 2A-K, 7A-F, 8A-C, 9A-H, and 16A-G) may be performed by first placing the central valve section inside the subject's left ventricle, and, subsequently, deploying the spacer at the annulus. For example, FIGS. 15A-E show a procedure in which the central valve section is placed inside the subject's left ventricle, and, subsequently, the spacer is deployed at the annulus.

Figure 15A:
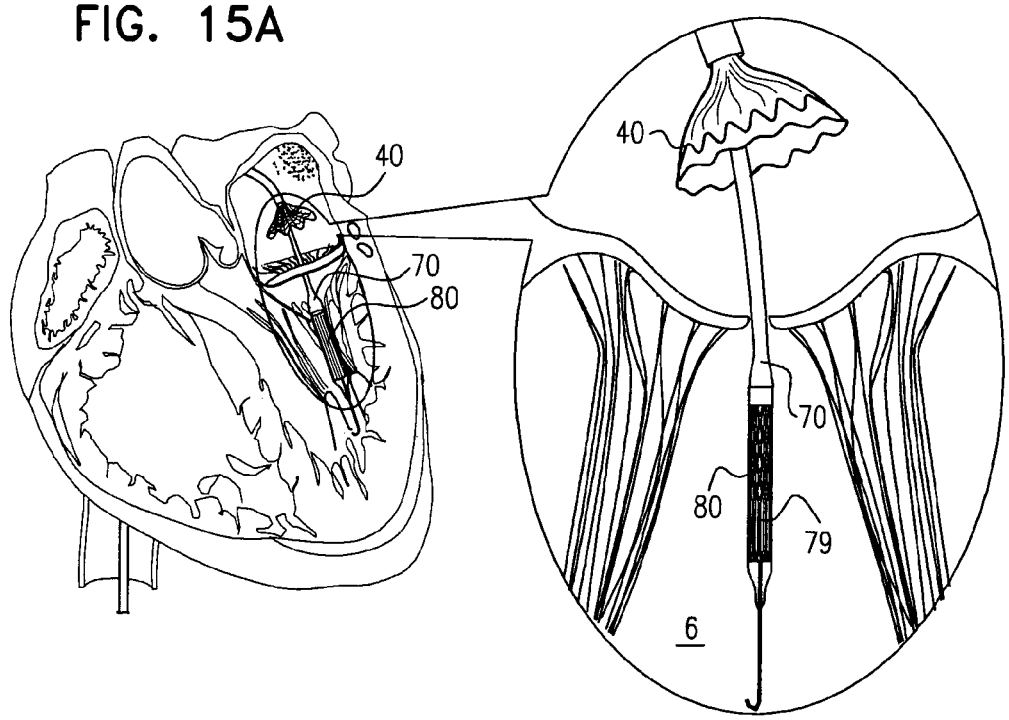
FIGS. 15A-E are schematic illustrations of respective steps of a procedure for deploying a prosthetic valve, in accordance with some embodiments of the present disclosure.
Figure 15B:
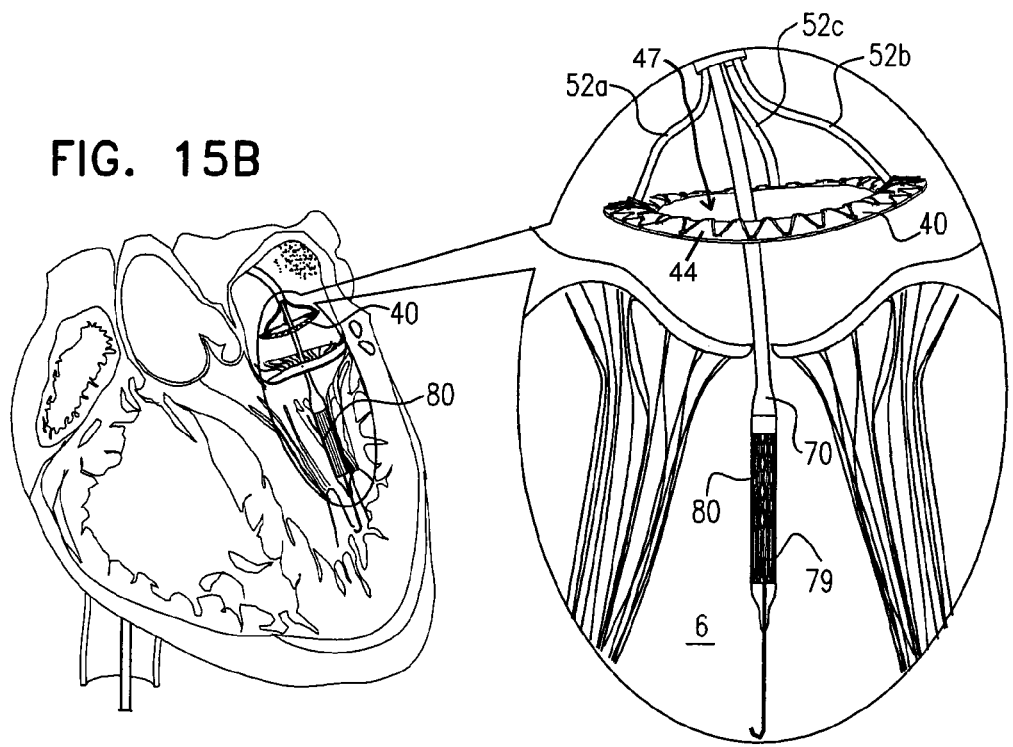

As shown in FIG. 15A, for some embodiments, central valve section 80 is placed in the subject's ventricle, before spacer 40 is placed at the native valve. The central valve section is in some embodiments placed in the left ventricle in an undeployed state, via overtube 70. Subsequently, the spacer is placed at the native valve using pushing elements, as shown in FIG. 15B. For some embodiments, three pushing elements 52a, 52b, and 52c are used to push the spacer against the native valve, as shown in FIG. 15B.

Figure 15C:
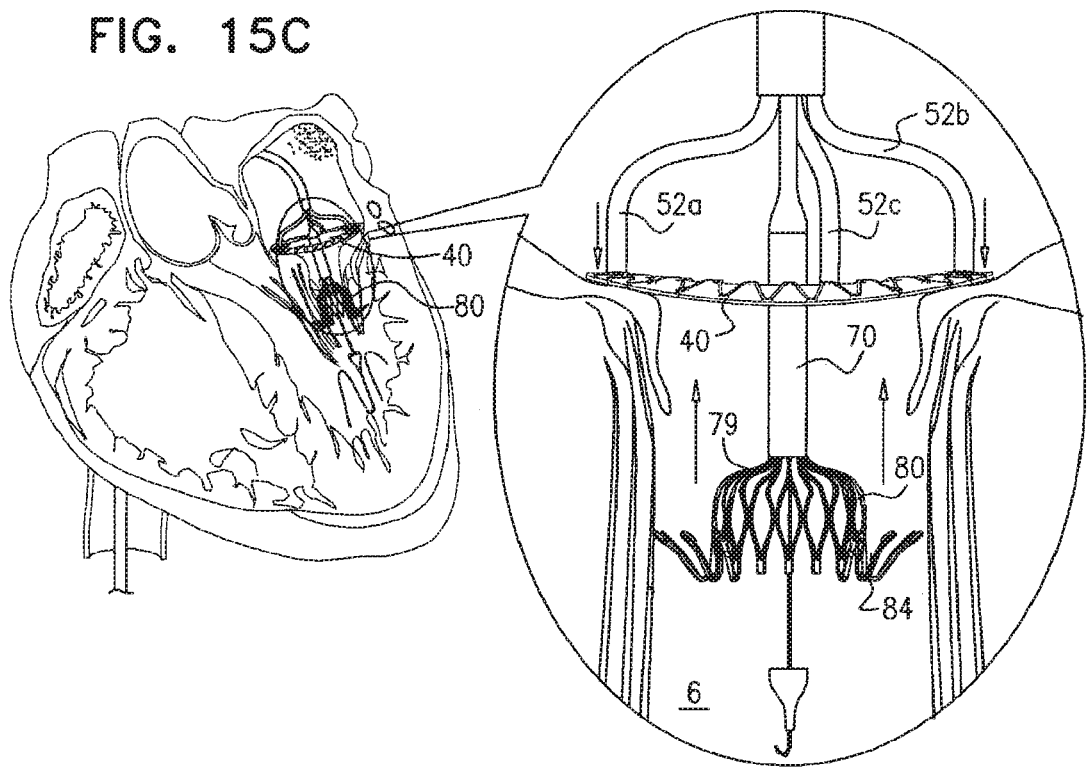

Subsequent to the placement of spacer 40 at the native valve, central valve section 80 is coupled to spacer 40. For some embodiments, pushing elements 52a, 52b, and 52c continue to push the spacer against the native valve, during the coupling of the central valve section to the spacer. FIG. 15C shows central valve section having been partially deployed in the ventricle.

Figure 15D:
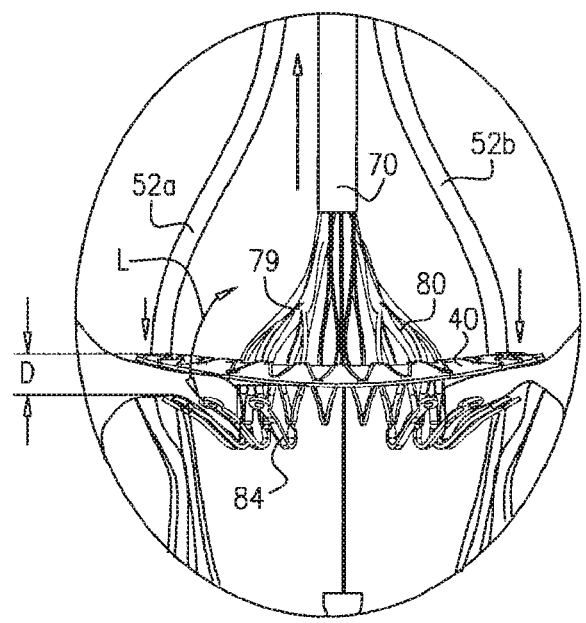

Following the partial deployment of central valve section 80 in ventricle 6, overtube 70 is pulled proximally to pull central valve section 80 proximally such that disc-shaped wall 44 of spacer 40 surrounds a proximal portion of central valve section 80, as shown in FIG. 15D. Central valve section 80 may be configured to expand such that central valve section 80 is held in place with respect to spacer 40 responsively to radial forces acted upon spacer 40 by central valve section 80. During the pulling back of overtube 70, pushing elements 52 *a*, 52 *b*, and 52 *c* push spacer 40 against the central valve section, thereby providing a counter force against which overtube 70 is pulled back. For some embodiments, the pushing of the spacer against the commissures is such that it is not necessary to use anchors for anchoring the spacer to the native valve during the coupling of the central valve section to the spacer. Alternatively, in addition to the pushing elements providing a counter force against which the central valve section is pulled, anchors are used to anchor the spacer to the native valve during the coupling of the central valve section to the spacer.

As described hereinabove, central valve section 80 includes a plurality of distal protrusions 84. When central valve section 80 is pulled proximally, as described hereinabove, protrusions 84 ensnare and engage the native leaflets of the atrioventricular valve. By the ensnaring of the native leaflets, protrusions 84 sandwich the native valve between protrusions 84 and spacer 40. Such ensnaring helps further anchor central valve section 80 to the native atrioventricular valve.

It is noted with reference to FIG. 15D that, in some embodiments, disc-shaped wall 44 of spacer 40 defines an inner cross-sectional area thereof. As described hereinabove, central valve section 80 includes expandable frame 79, and prosthetic leaflets 82. The expandable frame of the central valve section is configured such that when the frame is in a non-constrained state thereof, the cross-sectional area of the frame, along at least a given portion L (shown in FIG. 15D) of the length of the frame, is greater than the inner cross-sectional area defined by the disc-shaped wall of the spacer. In some embodiments, during a central valve section deployment procedure, a location anywhere along portion L at which to couple the expandable central valve section to the spacer is selected. In response thereto, the location along the portion of the expandable frame is aligned with the disc-shaped wall of the spacer. The expandable central valve section is then coupled to the spacer at the location, responsively to radial forces acted upon the spacer by the expandable frame, by facilitating expansion of the expandable frame, when the location along the portion is aligned with the disc-shaped wall of the spacer.

As described hereinabove, for some embodiments, expandable frame 79 of central valve section 80 has a frustoconical shape. For some embodiments, the central valve section is coupled to spacer 40 responsively to radial forces acted upon the spacer by the expandable frame, when a given location along portion L is aligned with disc-shaped wall 44 of the spacer. For some embodiments, the portion immediately proximal to the given location along portion L has a greater cross-sectional area than the frame at the given location, due to the frustoconical shape of the expandable frame. In some embodiments, the greater cross-sectional area of the portion immediately proximal to the given location along portion L relative to the cross-sectional area of the frame at the given location, reduces distal migration of the central valve section toward the subject's left ventricle.

For some embodiments, the location along portion L at which to couple central valve section 80 to spacer 40 is selected, based upon a distance D between protrusions 84 and disc-shaped wall 44 that would result from coupling the central valve section to the disc-shaped wall at that location. For example, the location along portion L at which to couple central valve section 80 to spacer 40 may be selected, such that distance D is such as to anchor the central valve section to the patient's native valve by squeezing the patient's native valve leaflets between the protrusions and the disc-shaped wall, and/or by ensnaring the patient's chordae tendinae between the protrusions and the disc-shaped wall. Alternatively or additionally, the location along portion L at which to couple central valve section 80 to spacer 40 may be selected, such that distance D is such that protrusions 84 (a) prevent proximal migration of the central valve section into the patient's atrium, while (b) allowing movement of the native leaflets with respect to the frame of the central valve section. In some embodiments, the location along portion L is selected such that distance is such that the central valve section may be stopped from proximally migrating into the atrium, by the protrusions preventing the distal end of the central valve section from migrating further proximally than edges of native leaflets of the valve, while the protrusions allow movement of the native leaflets with respect to the frame of the central valve section by not generally squeezing the native leaflets between the protrusions and the frame of the central valve section. For some embodiments, by allowing movement of the native leaflets with respect to the frame of the central valve section sealing of the native leaflets against the outer surface of the frame of the central valve section is facilitated, in accordance with the techniques described hereinabove with reference to FIG. 10.

Figure 15E:
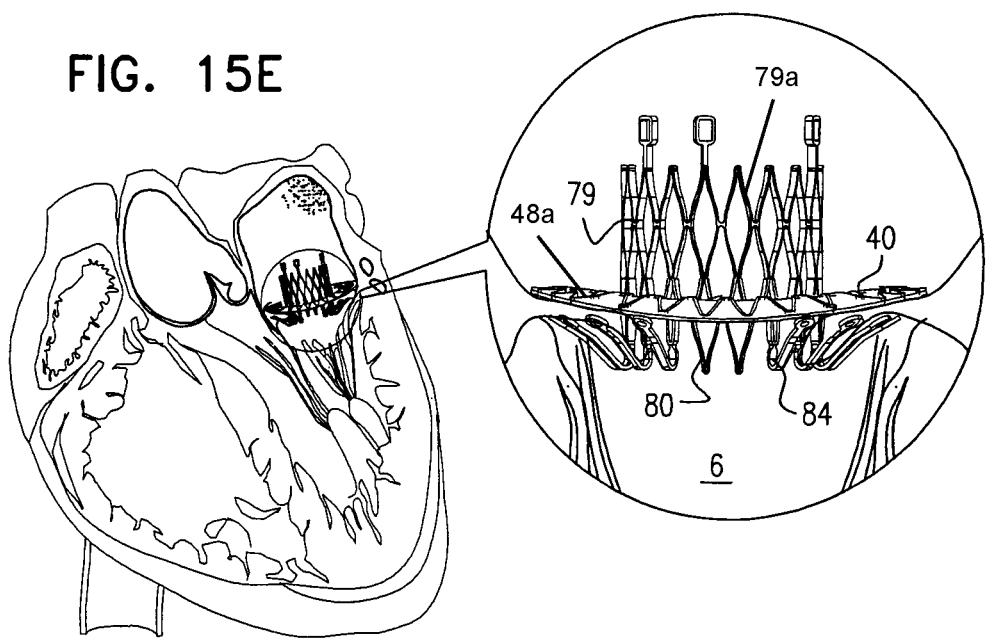

Subsequent to the placement of the central valve section at the native valve, overtube 70, and pushing elements 52a, 52b, and 52c are removed from the patient's body, as shown in FIG. 15E, which shows the central valve section in its deployed state.

Reference is now made to FIGS. 16A-G, which are schematic illustrations of respective steps of an alternative procedure for deploying central valve section 80, in accordance with some embodiments of the present disclosure. As described hereinabove, with reference to FIGS. 7A-F, for some embodiments, a looped guide member 21 is looped through commissures 8 and 10 in a manner in which the guide member defines a looped portion between commissures 8 and 10. For some embodiments, the looped guide member has steering functionality. The steering functionality of the looped guide member is used to guide the guide member to the commissures, and/or to guide other portions of the apparatus to the native valve and/or to ventricle 6. The looped guide member is in some embodiments advanced toward ventricle 6 over guidewire 306, e.g., as described hereinabove with reference to FIG. 7A.

Figure 16A:
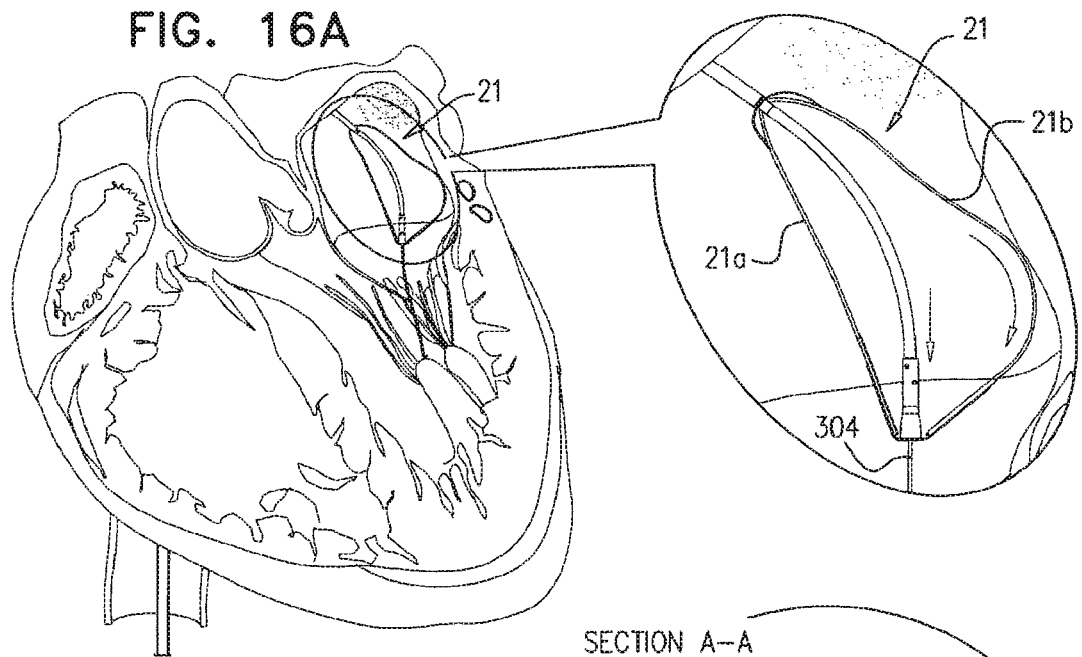

In some embodiments, as shown in FIG. 16A, portions 21a and 21b of the looped guide member are independently manipulable. The portions of the looped guide member are manipulated (e.g., expanded and contracted) so as to guide the looped guide member to the subject's native valve, by pushing against inner surfaces of the subject's heart, as shown in FIG. 16A.

Figure 16B:
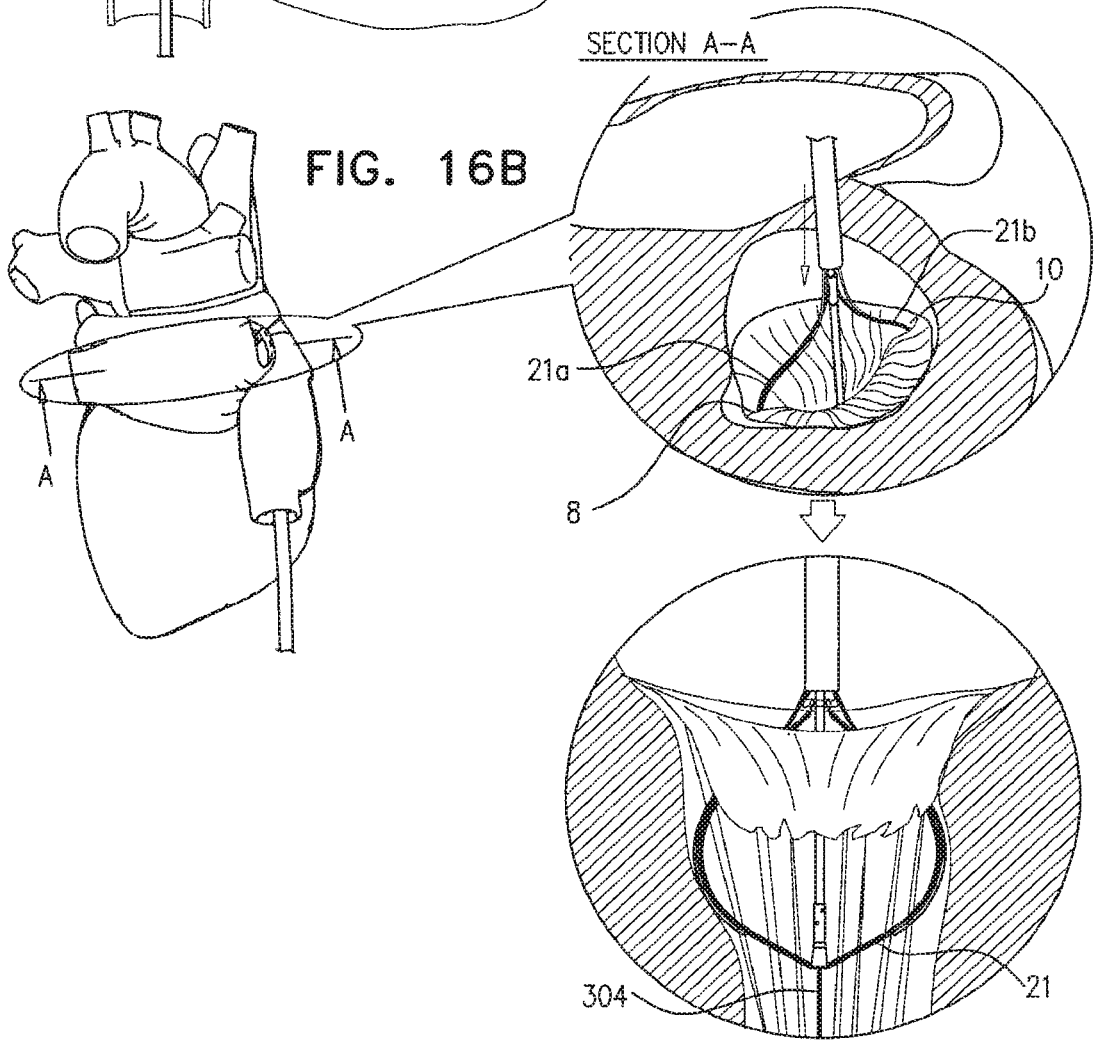

FIG. 16B shows the looped guide member looped through commissures 8 and 10 of the subject's native valve. When the looped guide member is disposed at the native valve, the guide member is used to guide and to anchor spacer 40, as described hereinbelow.

As shown in FIG. 16C, for some embodiments, looped guide member 21 is coupled to spacer 40 via coupling wires 500 and coupling mechanisms 502. For example, as shown, the coupling mechanism may include an anchor. A suture 504, or a different looped element, protrudes from the bottom surface of disc-shaped wall 44 of spacer 40 and is anchored by the anchor. Thus, when looped guide member 21 is pushed distally into ventricle 6, the spacer is pulled against the annulus of the native valve by coupling wires 500 pulling on the spacer.

In some embodiments, coupling mechanisms 502, which are used to couple looped guide member 21 to spacer 40 are detachable coupling mechanisms. For example, as shown, the coupling mechanism may include an anchor that defines an opening 506 through which suture 504 is inserted. The opening is closed by a closing member 508, such as a rod, or a wire. In order to detach the guide member from the spacer, closing member 508 is opened (e.g., by being pulled proximally) such that suture 504 is released through opening 506.

Figure 16D:
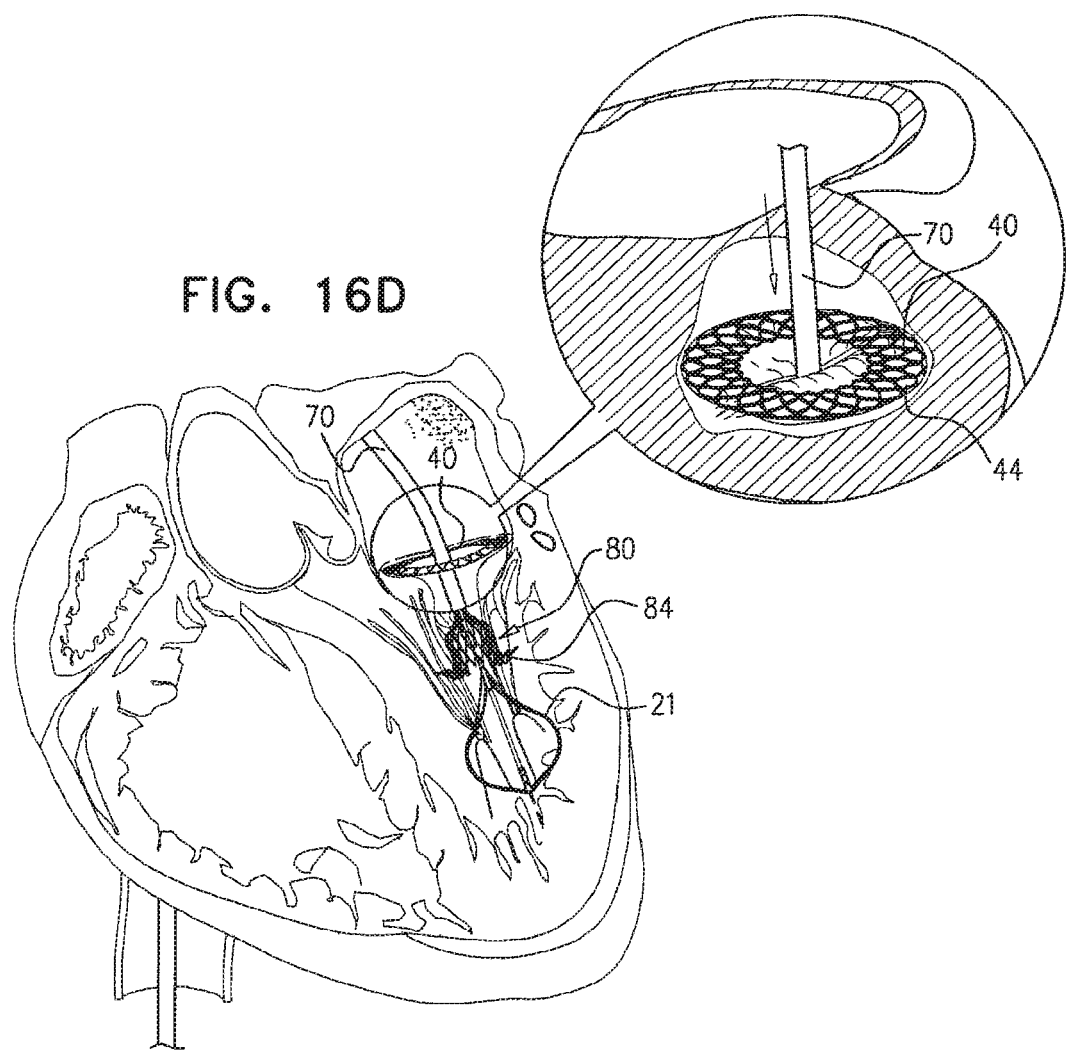
Figure 16E:
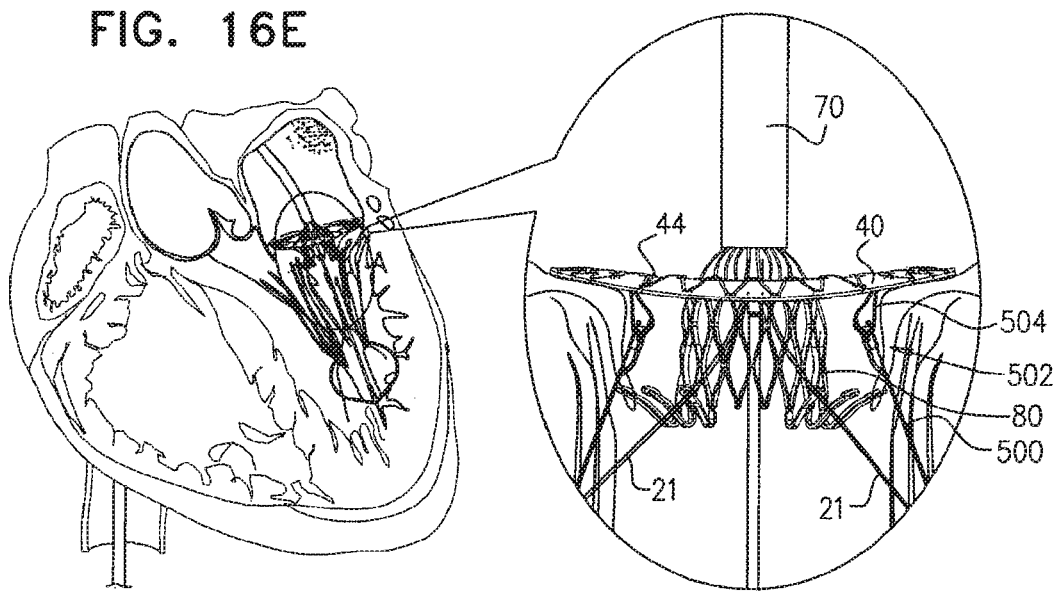
Figure 16F:
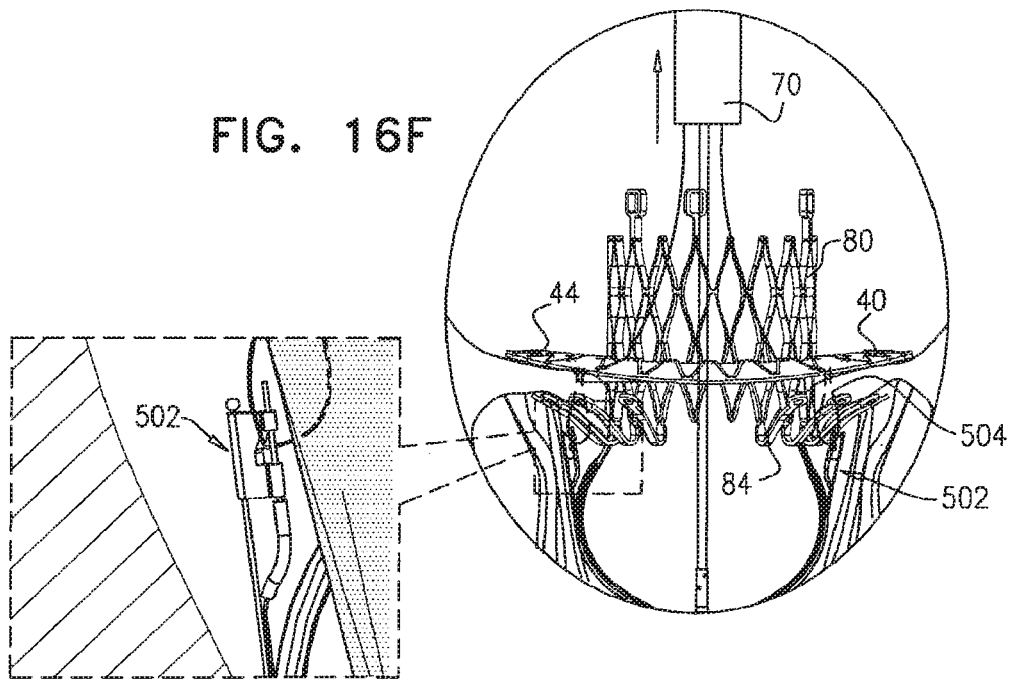

Subsequent to the placement of spacer 40 at the native valve, central valve section 80 is placed in ventricle 6, by advancing overtube 70 into the ventricle, as shown in FIG. 16D. FIG. 16E shows central valve section having been partially deployed in the ventricle. Following the partial deployment of central valve section 80 in ventricle 6, overtube 70 is pulled proximally to pull central valve section 80 proximally such that disc-shaped wall 44 of spacer 40 surrounds a proximal portion of central valve section 80, as shown in FIGS. 16E-F. Central valve section 80 may be configured to expand such that central valve section 80 is held in place with respect to spacer 40 responsively to radial forces acted upon spacer 40 by central valve section 80.

During the pulling back of overtube 70, looped guide member 21 is pushed distally, thereby pulling spacer 40 against the native annulus and providing a counter force against which overtube 70 is pulled back. For some embodiments, pulling of the spacer against the native annulus is such that it is not necessary to use anchors for anchoring the spacer to the native valve during the coupling of the central valve section to the spacer. Alternatively, in addition to the pulling of the spacer against the native annulus providing a counter force against which the central valve section is pulled, anchors are used to anchor the spacer to the native valve during the coupling of the central valve section to the central valve section.

Figure 16G:
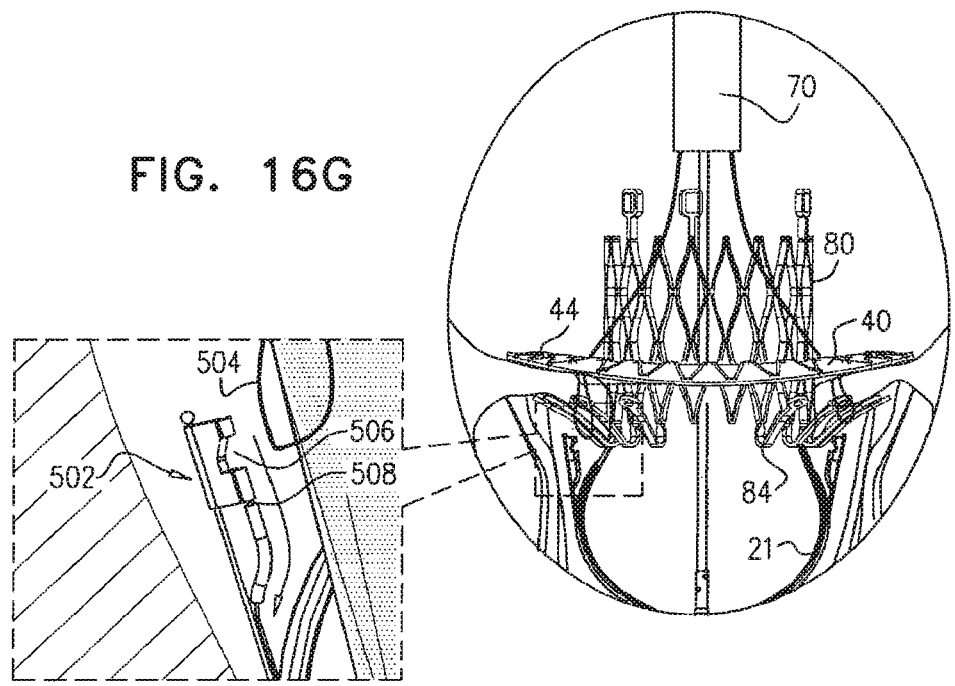
Figure 16H:
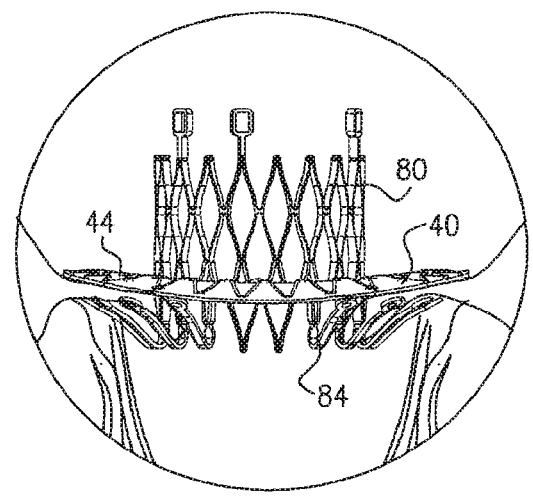

FIG. 16G shows central valve section 80 and spacer 40 coupled to the native valve. At this stage, coupling mechanism 502 is in some embodiments detached from the spacer. For example, as shown, closing member 508 is pulled, such that opening 506 is opened, and suture 504 is released through the opening. Subsequently, looped guide member 21, and overtube 70 are removed from the subject's body, as shown in FIG. 16H, which shows the central valve section in its deployed state.

As described with reference to FIGS. 16A-H, for some embodiments, central valve section 80 is coupled to a native valve, by (a) placing spacer 40 on an atrial side of the native annulus, (b) placing the central valve section inside the ventricle, and then, simultaneously, (c) pulling the central valve section toward the atrium, and pulling the spacer toward the ventricle.

Figure 17A:
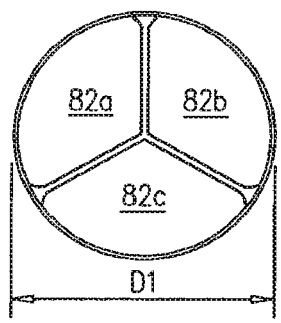
FIGS. 17A-C are schematic illustrations of leaflets of a prosthetic valve, in accordance with some embodiments of the present disclosure.
Figure 17B:
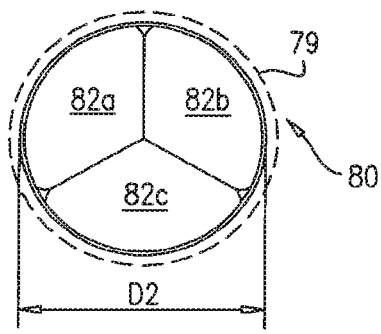
Figure 17C:
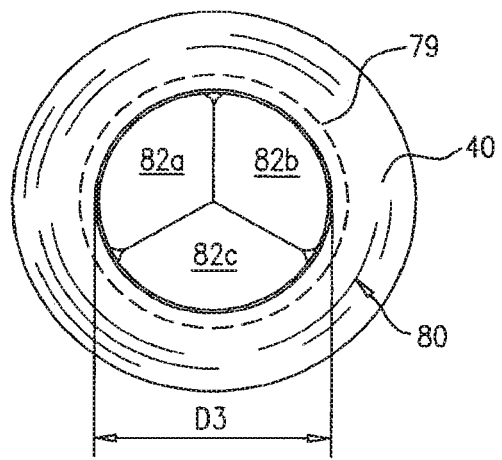

Reference is now made to FIGS. 17A-C, which are schematic illustrations of leaflets 82 of central valve section 80, in accordance with some embodiments of the present disclosure. FIG. 17A shows the leaflets before the leaflets are sutured to expandable frame 79 of the central valve section. As shown, in this state, the leaflets have a diameter D1, and the leaflets are not fully closed. FIG. 17B shows the leaflets when the leaflets have been sutured to expandable frame 79 of the central valve section. The expandable frame constrains the leaflets, such that the leaflets define a diameter D2, which is smaller than diameter D1, thereby closing the leaflets. FIG. 17C shows the leaflets subsequent to the deployment of central valve section 80 inside spacer 40, the spacer constraining the expansion of the central valve section. Due to the spacer constraining the central valve section, the valve leaflets are constrained so as define a diameter D3, which is smaller than diameter D2.

In some embodiments, valve leaflets 82 are selected to be used in central valve section 80, the leaflets being sized such that both at diameter D2 (when the leaflets are constrained by expandable frame 79 but are not constrained by spacer 40) and at diameter D3 (when the leaflets are constrained by both expandable frame 79 and spacer 40), the valve leaflets fully coapt.

Figure 18A:
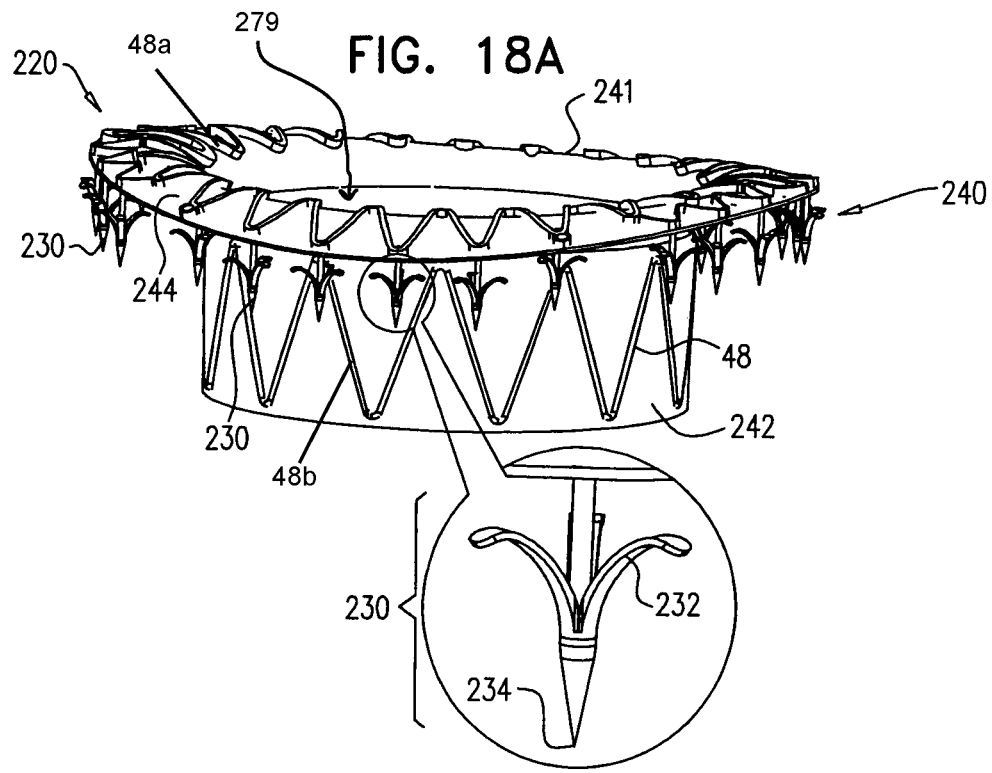
FIGS. 18A-B are schematic illustrations of a valve support coupled to a plurality of tissue anchors, in accordance with some embodiments of the present disclosure.
Figure 18B:
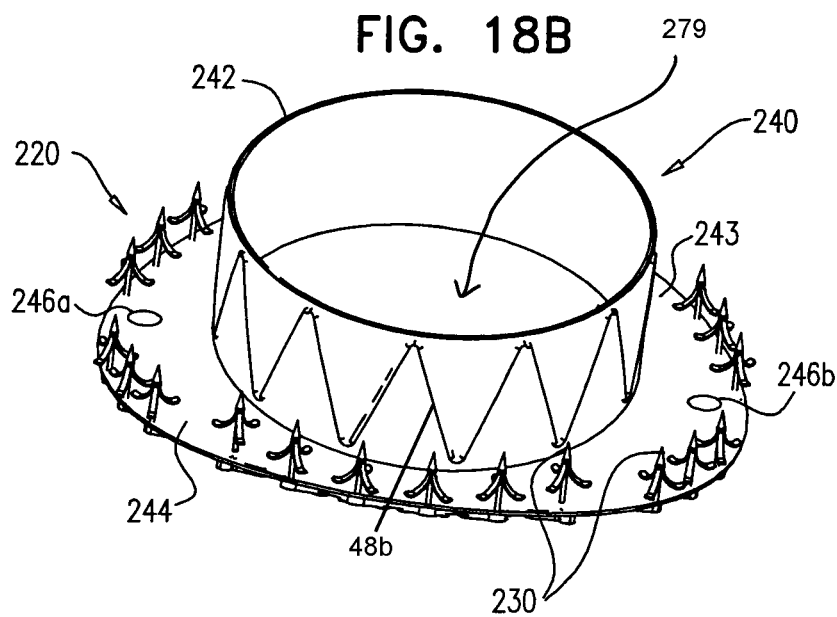

Reference is now made to FIGS. 18A-B which are schematic illustrations of a system 220 including a spacer 240 including a disc-shaped wall 244 and a cylindrical skirt 242 and one or more (e.g., a plurality, as shown, of) tissue anchor bases 230, in accordance with some embodiments of the present disclosure. Disc-shaped wall 244 has an upper surface 241 and a lower surface 243. Tissue anchor bases 230 are coupled to lower surface 234 of the disc-shaped wall. Tissue anchor bases 230 are shaped so as to define a pointed distal tip 234 and one or more (e.g., three, as shown) radially-expandable leaves 232. Leaves 232 include a flexible metal, e.g., nitinol or stainless steel, and have a tendency to expand radially. Tissue anchor bases 230 facilitate coupling of spacer 240 to annulus 11 of native valve 5, such as the mitral valve or the tricuspid valve. Tissue anchor bases 230 are in some embodiments distributed approximately evenly around lower surface 243 of disc-shaped wall 244. For some embodiments, one or more tissue anchor bases 230 are disposed at a location of disc-shaped wall that is configured to be positioned adjacently to commissures 8 and 10 of valve 5.

Reference is now made to FIGS. 19A-D which are schematic illustrations of spacer 240 being implanted at valve 5 and the subsequent coupling of central valve section 80 to spacer 240. Spacer 240 is advanced toward native valve 5 by pushing elements 52a and 52b, as described hereinabove with respect to spacer 40 with reference to FIGS. 2D-F. In response to the pushing force to spacer 240 by pushing elements 52a and 52b, tissue anchor bases 230 are pushed into tissue of annulus 11 of valve 5. The pushing force by elements 52a and 52b is sufficient to implant each one of the plurality of tissue anchor bases that are distributed around lower surface 243 of disc-shaped wall 244.

FIG. 19A shows initial penetration of tissue of annulus 11 by pointed distal tip 234 of anchor base 230. In FIG. 19B, the initial force of the tissue on leaves 232 pushes inwardly leaves 232. Finally, in FIG. 19C, leaves 232 expand within tissue of annulus 11 to assume a flower shape and a larger surface area to restrict proximal motion of anchor base 230 and thereby anchor spacer 240 in tissue of annulus 11. As shown in FIGS. 19A-C, the cylindrical element of spacer 240 pushes aside native leaflets 12 and 14 of valve 5.

In FIG. 19D, central valve section 80 is coupled to spacer 240, in a manner as described hereinabove.

It is noted that, in general, central valve section 80 is self-expandable. When the central valve section is deployed (i.e., when the central valve section self-expands) inside the subject's heart, the expansion of the central valve section is in some embodiments constrained by spacer 40. Further in some embodiments, the expansion of the central valve section is not constrained by the native annulus.

For some embodiments, by constraining the expansion of the central valve section with the spacer, the deployed cross-sectional area of the central valve section may be fixed at a given area, by using a spacer that defines a hole having the given cross-sectional area. As described hereinabove with reference to FIG. 10, for some embodiments, the area defined by the native annulus is measured, and the cross-sectional area of the central valve section that is to be deployed in the valve is selected based upon the measured area of the native annulus. Alternatively or additionally, spacer 40 is selected based upon the measured area of the native annulus.

For example, a spacer may be selected such that the spacer constrains the expansion of the central valve section, when the cross-sectional area of the central valve section is less than 90% (e.g., less than 80%, or less than 60%) of the area defined by the native annulus. As described hereinabove, for some embodiments, placing a central valve section inside the native valve with the dimensions of the native valve annulus and the central valve section being as described, facilitates sealing of the central valve section with respect to the native valve, by the native valve leaflets closing around the outer surface of the central valve section.

For some embodiments, the expansion of central valve section 80 against spacer 40 couples the central valve section to the spacer, and/or couples the central valve section and the spacer to the native mitral valve. In some embodiments, the expansion of the central valve section against the spacer couples the central valve section to the spacer, and sandwiching of the native valve leaflets between protrusions from the distal end of the central valve section and the spacer couples the central valve section and the spacer to the native valve.

Reference is now made to FIGS. 1A-D, 2A-K, 3A-D, 4A-C, 5A-D, 6A-B, 7A-F, 8A-C, 9A-H, 10, 11A-D, and 12A-C. It is to be noted that spacer 40 may be invertible as described hereinabove with respect to spacer 140 and spacer 300, with reference to FIGS. 8A-C, and 9A-H. It is to be further noted that spacer 140 and spacer 300 may be used in conjunction with one or more of the elements for facilitating sealing of the native valve with respect to a spacer or a central valve section that is described with reference to FIGS. 3A-D, 4A-C, 5A-D, and 6A-B. For example, spacer 140 and spacer 300 may be used with sealing balloon 90, commissural anchors 100*a* and 100*b*, grasping elements 106*a* and 106*b*, and/or sealing material 110. It is still further noted that spacer 140 and spacer 300 may be implanted using a guide member that defines a looped portion between commissures 8 and 10, as described with reference to FIGS. 7A-F. It is further noted that any of the embodiments described herein can be used in conjunction with central valve sections having configurations as described with reference to FIGS. 10-12C.

The systems described herein are advanced toward valve 5 in a transcatheter procedure, as shown. It is to be noted, however, that the systems described herein may be advanced using any suitable procedure, e.g., minimally-invasively (e.g., via a transeptal, a transatrial, a transapical, and/or a transaortic approach), or using an open-heart procedure. It is to be further noted that spacers and prosthetic valves herein may be used to replace native mitral valves or native tricuspid valves.

Figure 20A:
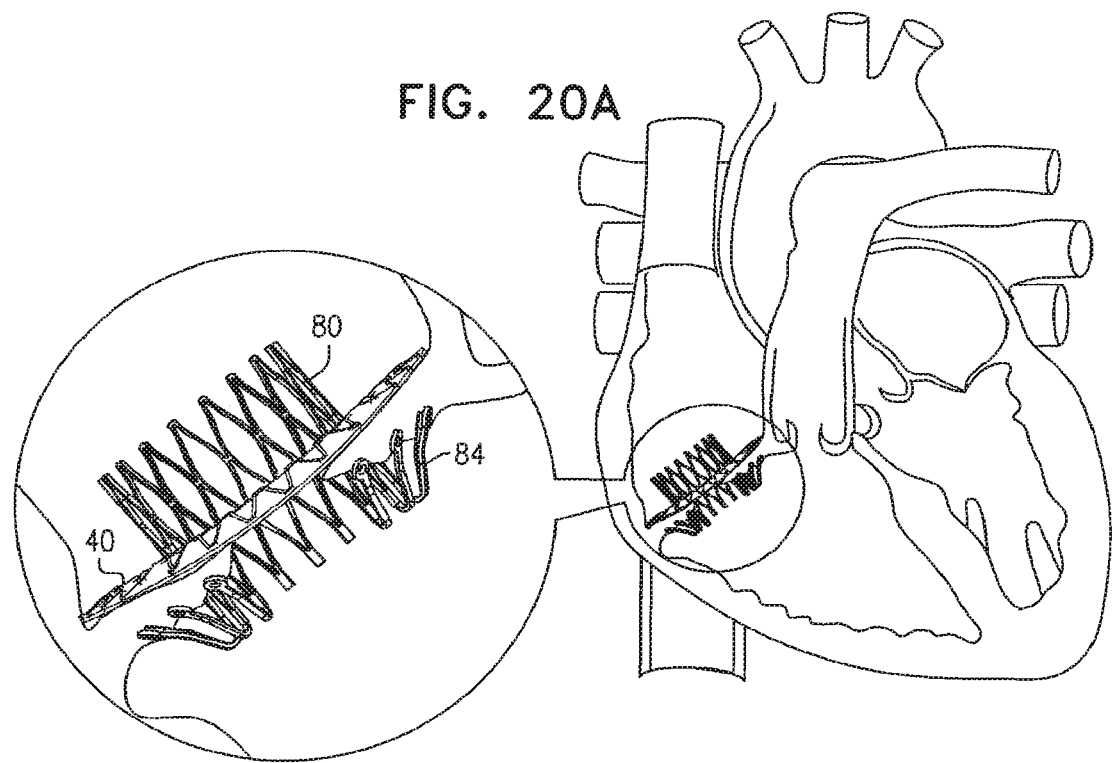
FIGS. 20A-B are schematic illustrations of a prosthetic valve and a prosthetic valve support deployed, respectively, at a tricuspid valve, and at an aortic valve, in accordance with some embodiments of the present disclosure.
Figure 20B:
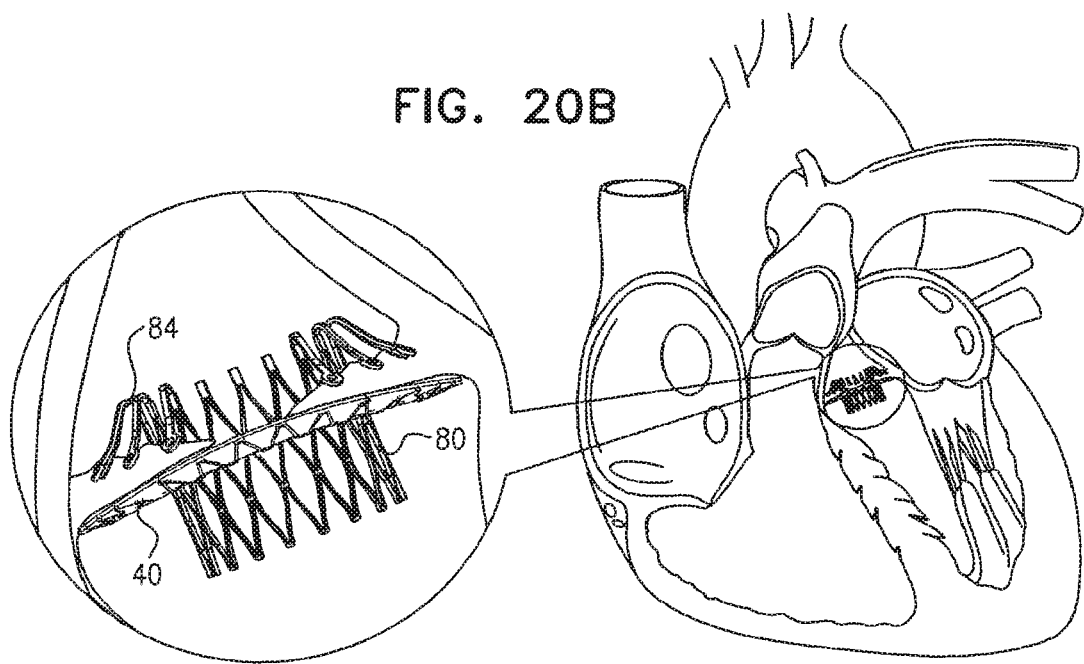

Reference is now made to FIGS. 20A-B, which are schematic illustrations of spacer 40 and central valve section 80 coupled respectively to a tricuspid valve, and to an aortic valve, in accordance with some embodiments of the present disclosure. For some embodiments, spacer 40 and central valve section 80 are deployed at a tricuspid valve and/or at an aortic valve using generally similar techniques to those described herein with reference to the deployment of the spacer and the central valve section at the mitral valve, mutatis mutandis.

It will be appreciated by persons skilled in the art that the present disclosure is not limited to what has been particularly shown and described hereinabove. Rather, the scope of the present disclosure includes both combinations and subcombinations of the various features described hereinabove, as well as variations and modifications thereof that are not in the prior art, which would occur to persons skilled in the art upon reading the foregoing description.

The invention claimed is:

1. A prosthetic heart valve, comprising:
    an annular spacer configured for deployment within a native heart valve, the annular spacer comprising:
        a cylindrical skirt having an upstream end and a downstream end opposite from the upstream end, wherein a spacer opening extends through the cylindrical skirt between the upstream and downstream ends, and
        a disc-shaped wall arranged about the upstream end of the cylindrical skirt, the disc-shaped wall being configured to obstruct blood flow, wherein the disc-shaped wall comprises:
            a support stent having a plurality of struts, and
            at least one opening configured to slide along a delivery mechanism, wherein a first portion of the support stent situated around the at least one opening has a different strut arrangement than a second portion of the support stent; and
    a central valve section having a central lumen configured to support a valve prosthesis therein, wherein the central valve section is configured for disposal within the spacer opening of the annular spacer and includes at least one anchoring protrusion configured to extend radially outward from a downstream end of the central valve section,
    wherein the central valve section is configured for deployment into the heart separately from the annular spacer, and
    wherein the at least one anchoring protrusion of the central valve section is configured to extend through the downstream end of the spacer opening to prevent the central valve section from moving axially relative to the annular spacer.

2. The prosthetic heart valve of claim 1,
    wherein the annular spacer is configured for engaging with an annulus of the native heart valve, and
    wherein the spacer opening is sized to be smaller than the annulus of the native heart valve.

3. The prosthetic heart valve of claim 1, wherein the central valve section is configured for implantation after implantation of the annular spacer.

4. The prosthetic heart valve of claim 1, wherein the annular spacer is configured to secure the central valve section relative to an annulus of the native heart valve.

5. The prosthetic heart valve of claim 1,
    wherein the cylindrical skirt is configured to extend at least partially into a ventricle of the heart, and
    wherein the disc-shaped wall is configured to contact an atrial side of the native heart valve.

6. The prosthetic heart valve of claim 1, wherein an outer diameter of the disc-shaped wall is configured to be larger than an outer diameter of an upstream end of the central valve section.

7. The prosthetic heart valve of claim 1, wherein the cylindrical skirt comprises:
    a second support stent having a second plurality of struts; and
    a covering that covers at least a portion of the second support stent along the downstream end of the cylindrical skirt.

8. The prosthetic heart valve of claim 1, wherein the central valve section includes:
    a flexible wire frame having a second plurality of struts; and
    a plurality of anchoring protrusions, wherein each anchoring protrusion includes:
        a proximal end secured to at least one strut of the flexible wire frame, and
        a distal end opposite from the proximal end.

9. The prosthetic heart valve of claim 8, wherein the anchoring protrusions are configured such that when the central valve section is disposed within the spacer opening of the annular spacer, a circumference defined by the distal ends of the anchoring protrusions has a larger diameter than an outer diameter of the downstream end of the cylindrical skirt.

10. The prosthetic heart valve of claim 8, wherein the distal ends of the anchoring protrusions are configured to be the radially-outermost portions of the central valve section, relative to a center of the central valve section.

11. The prosthetic heart valve of claim 1, wherein the at least one anchoring protrusion is configured to extend radially outward beyond an outer diameter of the downstream end of the cylindrical skirt when the central valve section is disposed within the spacer opening of the annular spacer.

12. The prosthetic heart valve of claim 1, wherein the central valve section has a greater axial length than the annular spacer.

13. A prosthetic heart valve, comprising:
an annular spacer configured for deployment within a native heart valve, the annular spacer comprising:
a cylindrical skirt having an upstream end and a downstream end opposite from the upstream end, wherein a spacer opening extends through the cylindrical skirt between the upstream and downstream ends, and
a disc-shaped wall arranged about the upstream end of the cylindrical skirt, wherein the disc-shaped wall is configured to obstruct blood flow;
a central valve section having a central lumen configured to support a valve prosthesis therein, wherein the central valve section is configured for disposal within the spacer opening of the annular spacer and includes at least one anchoring protrusion configured to extend radially outward from a downstream end of the central valve section; and
at least one tissue anchor configured to extend through an opening of the disc-shaped wall to secure the disc-shaped wall to tissue of the native heart valve,
wherein the central valve section is configured for deployment into the heart separately from the annular spacer,
wherein the at least one anchoring protrusion of the central valve section is configured to extend through the downstream end of the spacer opening to prevent the central valve section from moving axially relative to the annular spacer, and
wherein the at least one tissue anchor is configured for deployment into the heart separately from the annular spacer and includes a plurality of leaves configured to splay outward upon implantation of the at least one tissue anchor.

14. The prosthetic heart valve of claim 13, wherein the at least one tissue anchor is configured to engage ventricular tissue of the native heart valve.

15. The prosthetic heart valve of claim 13, wherein the at least one tissue anchor is configured to be secured to the disc-shaped wall via a male-female locking arrangement.

16. A prosthetic heart valve, comprising:
an annular spacer configured for deployment within a native heart valve, the annular spacer comprising:
a cylindrical skirt having an upstream end and a downstream end opposite from the upstream end, wherein a spacer opening extends through the cylindrical skirt between the upstream and downstream ends, and
a disc-shaped wall arranged about the upstream end of the cylindrical skirt, wherein the disc-shaped wall is configured to obstruct blood flow; and
a central valve section having a central lumen configured to support a valve prosthesis therein, wherein the central valve section is configured for disposal within the spacer opening of the annular spacer and includes at least one anchoring protrusion configured to extend radially outward from a downstream end of the central valve section,
wherein the central valve section is configured for deployment into the heart separately from the annular spacer,
wherein the at least one anchoring protrusion of the central valve section is configured to extend through the downstream end of the spacer opening to prevent the central valve section from moving axially relative to the annular spacer, and
wherein the cylindrical skirt is configured to be inverted such that a first end of the cylindrical skirt is situated upstream of the disc-shaped wall after deployment of the annular spacer within the native heart valve, the first end of the cylindrical skirt being the downstream end of the cylindrical skirt when the cylindrical skirt is in a non-inverted configuration.

17. The prosthetic heart valve of claim 16, wherein the central valve section is configured to reposition the first end of the inverted cylindrical skirt such that the cylindrical skirt is moved into the non-inverted configuration.

18. The prosthetic heart valve of claim 16, configured such that native leaflets of the heart are not obstructed by the prosthetic heart valve until the central valve section is implanted and the cylindrical skirt is moved into the non-inverted configuration.

19. A prosthetic heart valve, comprising:
an annular spacer configured for deployment within a native heart valve, the annular spacer comprising:
a cylindrical skirt having an upstream end and a downstream end opposite from the upstream end, wherein a spacer opening extends through the cylindrical skirt between the upstream and downstream ends, and
a disc-shaped wall arranged about the upstream end of the cylindrical skirt, wherein the disc-shaped wall is configured to obstruct blood flow; and
a central valve section having a central lumen configured to support a valve prosthesis therein, wherein the central valve section is configured for disposal within the spacer opening of the annular spacer and includes at least one anchoring protrusion configured to extend radially outward from a downstream end of the central valve section,
wherein the central valve section is configured for deployment into the heart separately from the annular spacer,
wherein the at least one anchoring protrusion of the central valve section is configured to extend through the downstream end of the spacer opening to prevent the central valve section from moving axially relative to the annular spacer,
wherein the at least one anchoring protrusion is configured to extend radially outward beyond an outer diameter of the downstream end of the cylindrical skirt when the central valve section is disposed within the spacer opening of the annular spacer, and
wherein the at least one anchoring protrusion is configured to engage native leaflets of the heart and to compress the native leaflets of the heart against the annular spacer.

* * * * *